US008058284B2

(12) United States Patent
Scarborough et al.

(10) Patent No.: US 8,058,284 B2
(45) Date of Patent: Nov. 15, 2011

(54) [4-(6-HALO-7-SUBSTITUTED-2,4-DIOXO-1,4-DIHYDRO-2H-QUINAZOLIN-3-YL)-PHENYL]-5-CHLORO-THIOPHEN-2-YL-SULFONYLUREAS AND FORMS AND METHODS RELATED THERETO

(75) Inventors: Robert Scarborough, Half Moon Bay, CA (US); Carroll Anna Scarborough, legal representative, Half Moon Bay, CA (US); Wolin Huang, Foster City, CA (US); Mukund Mehrotra, South San Francisco, CA (US); Xiaoming Zhang, Sunnyvale, CA (US); Hilary Cannon, Hertfordshire (GB); Craig M. Grant, Burwell (GB)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 1353 days.

(21) Appl. No.: 11/556,490

(22) Filed: Nov. 3, 2006

(65) Prior Publication Data
US 2007/0123547 A1 May 31, 2007

Related U.S. Application Data

(60) Provisional application No. 60/733,650, filed on Nov. 3, 2005.

(51) Int. Cl.
A61K 31/517 (2006.01)
C07D 409/12 (2006.01)
(52) U.S. Cl. .................. 514/266.24; 544/285
(58) Field of Classification Search ............. 514/266.24; 544/284
See application file for complete search history.

(56) References Cited

U.S. PATENT DOCUMENTS

| 3,847,925 | A | 11/1974 | Beregi et al. | |
|---|---|---|---|---|
| 4,542,139 | A | 9/1985 | Hitzel et al. | |
| 4,720,450 | A | 1/1988 | Ellis | |
| 5,475,025 | A | 12/1995 | Tjoeng et al. | |
| 6,160,000 | A | 12/2000 | Adams et al. | |
| 6,413,724 | B1 | 7/2002 | Gordeev et al. | |
| 6,689,786 | B2 | 2/2004 | Scarborough et al. | |
| 6,824,790 | B2 | 11/2004 | Yatvin | |
| 6,906,063 | B2 | 6/2005 | Scarborough et al. | |
| 6,951,937 | B2 | 10/2005 | Kanter et al. | |
| 7,022,731 | B2 | 4/2006 | Scarborough et al. | |
| 7,056,926 | B2 | 6/2006 | Scarborough et al. | |
| 7,358,257 | B2 * | 4/2008 | Scarborough et al. ..... | 514/266.3 |
| 2002/0025961 | A1 | 2/2002 | Scarbrough et al. | |
| 2002/0077486 | A1 | 6/2002 | Scarborough | |
| 2003/0162774 | A1 | 8/2003 | Scarbrough et al. | |
| 2004/0147576 | A1 | 7/2004 | Scarbrough et al. | |
| 2004/0242658 | A1 | 12/2004 | Reddy et al. | |
| 2005/0107357 | A1 | 5/2005 | Scarbrough et al. | |
| 2005/0228029 | A1 | 10/2005 | Scarbrough et al. | |
| 2009/0042916 | A1 * | 2/2009 | Sharp et al. ............... | 514/266.24 |
| 2009/0048216 | A1 * | 2/2009 | Gretler et al. ................. | 514/159 |
| 2009/0156620 | A1 * | 6/2009 | Sharp et al. ............... | 514/266.24 |

FOREIGN PATENT DOCUMENTS

| DE | 845 042 | 7/1952 |
|---|---|---|
| EP | 1 257 550 B1 | 11/2005 |
| EP | 1 412 364 B1 | 9/2006 |
| JP | 08-081442 A | 3/1996 |
| JP | 10-502630 A | 3/1998 |
| JP | 10-195323 A | 7/1998 |
| JP | 2000-204081 A | 7/2000 |
| JP | 2003-522177 A | 7/2003 |
| WO | WO 94/19341 A1 | 9/1994 |
| WO | WO 94/21602 A1 | 9/1994 |
| WO | WO 96/02508 A1 | 2/1996 |
| WO | WO 99/36425 A1 | 7/1999 |
| WO | WO 01/57037 A1 | 8/2001 |
| WO | WO 03/011872 A1 | 2/2003 |
| WO | WO 2007/056167 A3 | 5/2007 |

OTHER PUBLICATIONS

Fredholm, Bertil B., "Towards a revised nomenclature for P1 and P2 receptors," *TIPS*, 1997, vol. 18, pp. 79-82.
Hechler, Beatrice, et al., "The P2Y Receptor Is Necessary for Adenosine 5'-Diphosphate-Induced Platelet Aggregation," *Blood*, 1998, vol. 92, No. 1, pp. 152-159.
Hollopeter, Gunther, et al., "Identification of the platelet ADP receptor targeted by antithrombotic drugs," *Nature*, 2001, vol. 409, pp. 202-207.
Hunt, Cecilia, et al., "3-Substituted Thieno[2,3-b][1,4]thiazine-6-sulfonamides. A Novel Class of Topically Active Carbonic Anhydrase Inhibitors," *J. Med. Chem*, 1994, vol. 37, pp. 240-247.
Jantzen, H.M, et al., "Evidence for Two Distinct G-Protein-coupled ADP Receptors Mediating Platelet Activation," *Thrombosis and Haemostasis*, 1999, vol. 81, No. 1, pp. 111-117.
King, Brian F, et al., "Metabotropic receptors for ATP and UTP: exploring the correspondence between native and recombinant nucleotide receptors," *TIPS*, 1998, vol. 19, pp. 506-514.
Kunapuli, Satya P., "Multiple P2 receptor subtypes on platelets: a new interpretation of their function," *TIPS*, 1998, vol. 19, pp. 381-394.
Kunapuli, Satya P, et al., "P2 receptor subtypes in the cardiovascular system," *J. Biochem*, 1998, vol. 336, pp. 513-523.

(Continued)

*Primary Examiner* — Emily Bernhardt
(74) *Attorney, Agent, or Firm* — Kilpatrick Townsend and Stockton LLP

(57) ABSTRACT

The present invention provides novel sulfonylurea compounds of formula (I) and pharmaceutically acceptable derivatives and polymorph and amorphous forms thereof. The compounds in their various forms are effective platelet ADP receptor inhibitors and may be used in various pharmaceutical compositions, and are particularly effective for the prevention and/or treatment of cardiovascular diseases, particularly those diseases related to thrombosis. The invention also provides a method for preparing such compounds and forms and for preventing or treating thrombosis and thrombosis related conditions in a mammal comprising the step of administering a therapeutically effective amount of a compound of formula (I) or a pharmaceutically acceptable salt or forms thereof.

49 Claims, 20 Drawing Sheets

OTHER PUBLICATIONS

Mills, D.C.B, "ADP Receptors on Platelets," *Thrombosis and Haemostasis*, 1996, vol. 76, No. 6, pp. 835-856.

Plotnikova, et al., "Arenesulfonamides, LXXX. Aroylarenesulfonamides," Database CA Online Chemical Abstracts Service, Columbus, OH, US, retrieved from STN Database Accession No. 82 139564 XP002215531, abstract & Vopr. Khim, Khim. Tekhnol. (1974), vol. 33, pp. 20-25.

Hatzelmann, A., "Mode of action of the new selective leukotriene synthesis inhibitor BAY X 1005{(R)-2-[4-(quinolin-2-yl-methoxy)phenyl]-2-cyclopentyl acetic acid} and structurally related compounds," *Biochemical Pharmacology*, 1993, vol. 45, No. 1, pp. 101-111.

Holland, G.F., "Preparation of Some Additional Sulfonylureas," *Journal of Organic Chemistry*, May 1961, vol. 26, pp. 1662-1665.

Lacan, F., "Synthesis, structural characterization and thromboxane A2 receptor antagonistic activity of 3-substiuted 2-[(aryslulfonyl)imino]-2, 3-dihydrothiaozyl derivatives," *European Journal of Medicinal Chemistry*, 1999, vol. 34, No. 4, pp. 311-328.

Supplementary European Search Report mailed on Apr. 29, 2009, for EP Application No. 06827506.4, 3 pages.

Stack, D., "Electron Withdrawing and Electron Donating Groups," 2010, 2 pages.

Stack, D., "EWD-EDG Worksheet," 2010, located at <http://myweb.unomaha.edu/~dstack/2250/Problems/EWG_EDG.doc>, 4 pages.

Vippagunta, S.R. et al., "Crystalline solids," *Advanced Drug Delivery Reviews*, 2001, vol. 48, pp. 3-26.

\* cited by examiner

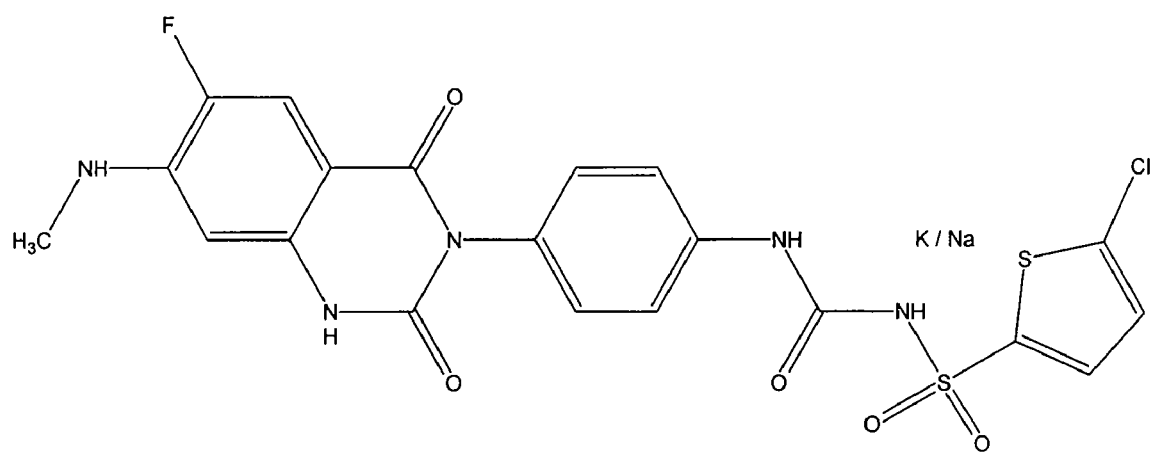
Figure 1 Structures of selected and preferred compounds of the invention.

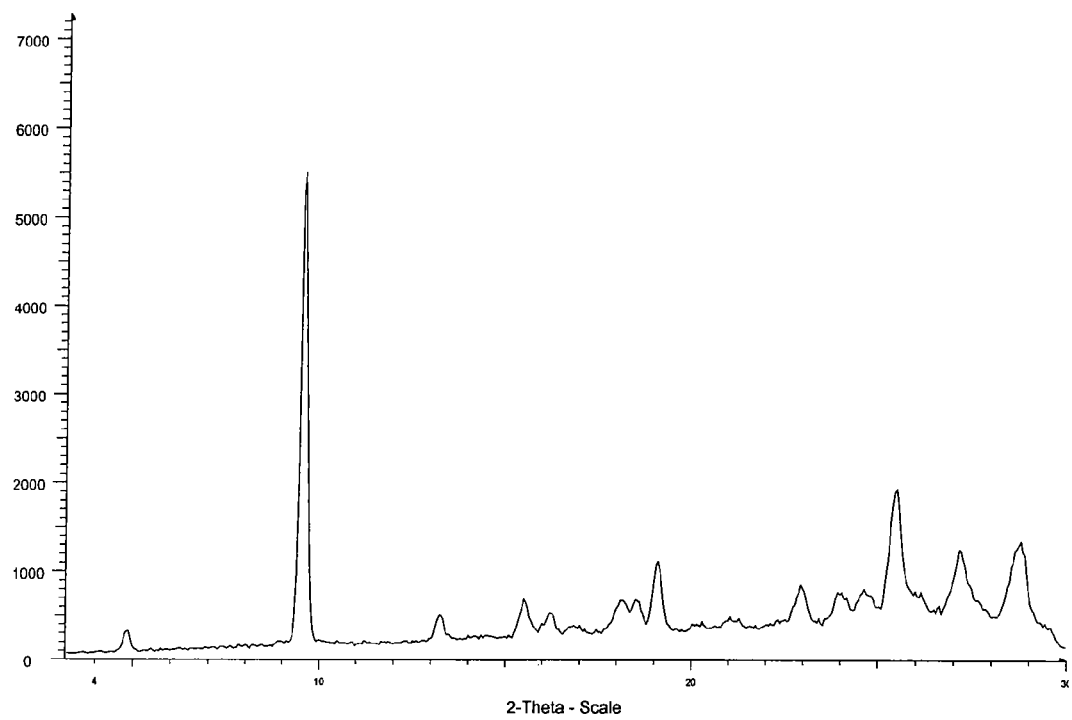
Figure 2a XRPD of [4-(6-fluoro-7-methylamino-2,4-dioxo-1,4-dihydro-2H-quinazolin-3-yl)-phenyl]-5-chloro-thiophen-2-yl-sulfonylurea potassium saltdihydrate (Form A)

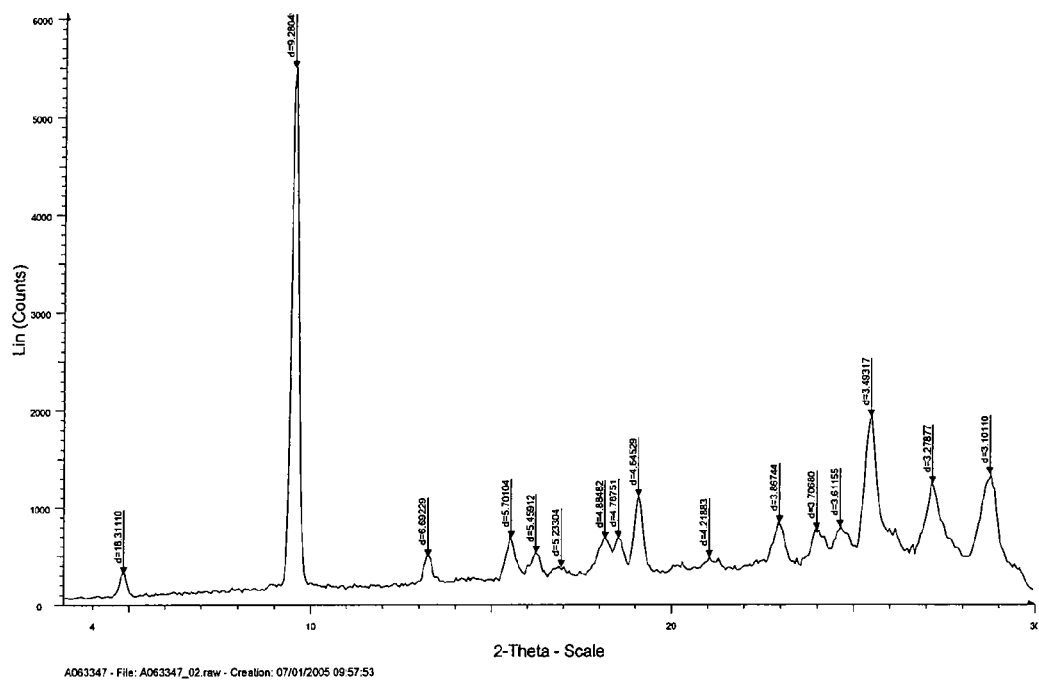
Figure 2b XRPD of [4-(6-fluoro-7-methylamino-2,4-dioxo-1,4-dihydro-2H-quinazolin-3-yl)-phenyl]-5-chloro-thiophen-2-yl-sulfonylurea potassium saltdihydrate (Form A) showing peak information

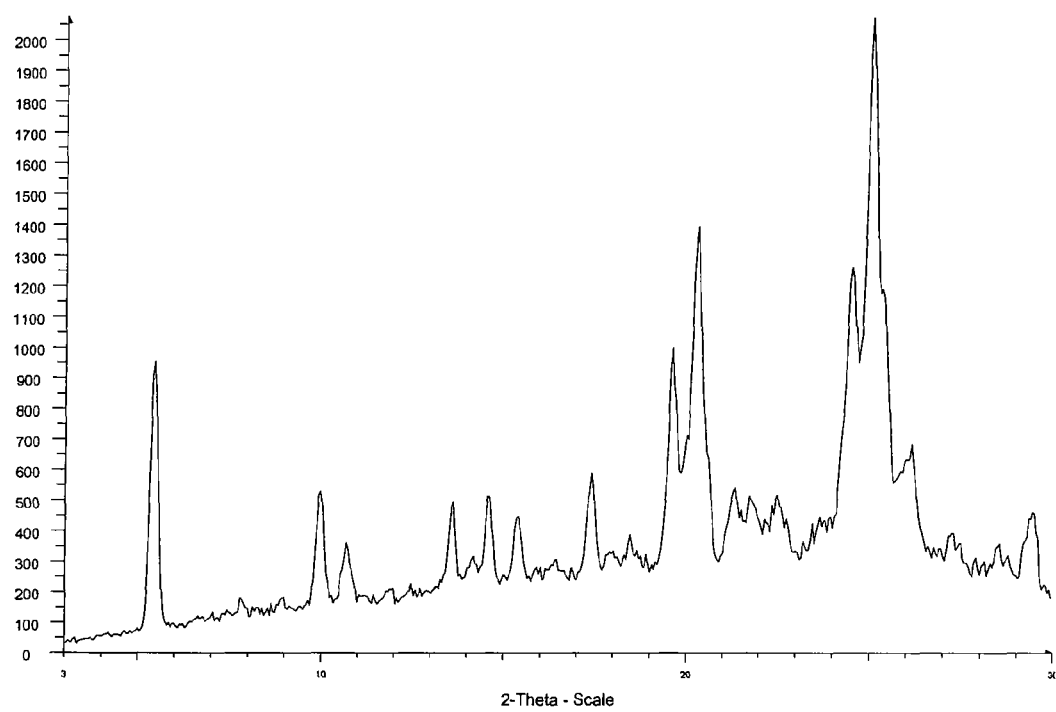
Figure 3a XRPD of [4-(6-fluoro-7-methylamino-2,4-dioxo-1,4-dihydro-2H-quinazolin-3-yl)-phenyl]-5-chloro-thiophen-2-yl-sulfonylurea potassium salt (Form B)

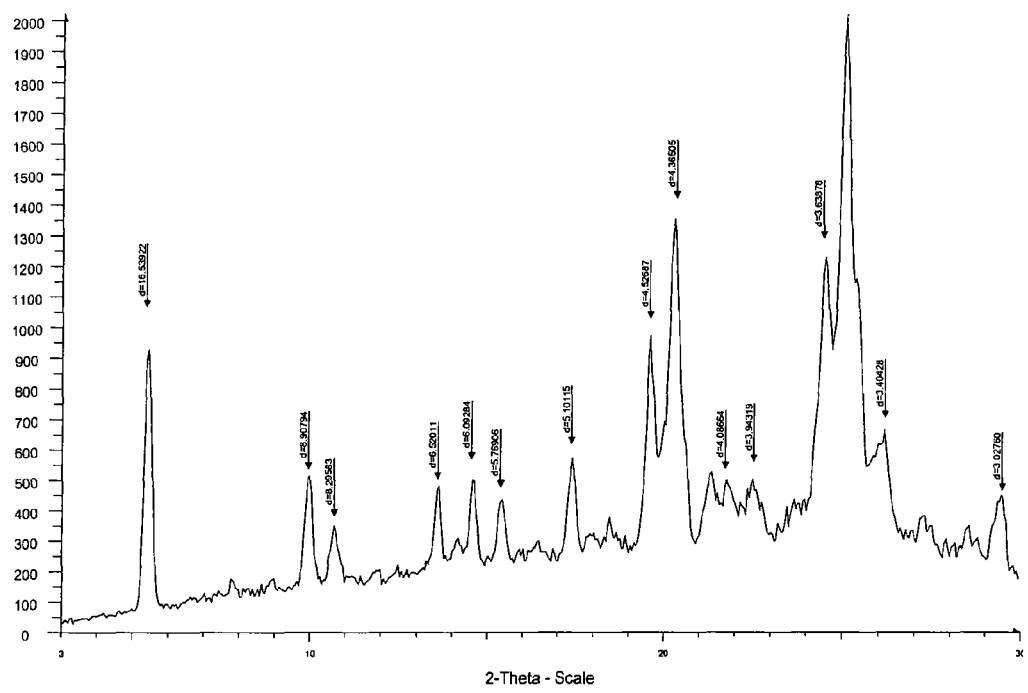
Figure 3b XRPD of [4-(6-fluoro-7-methylamino-2,4-dioxo-1,4-dihydro-2H-quinazolin-3-yl)-phenyl]-5-chloro-thiophen-2-yl-sulfonylurea potassium salt(Form B) showing peak information

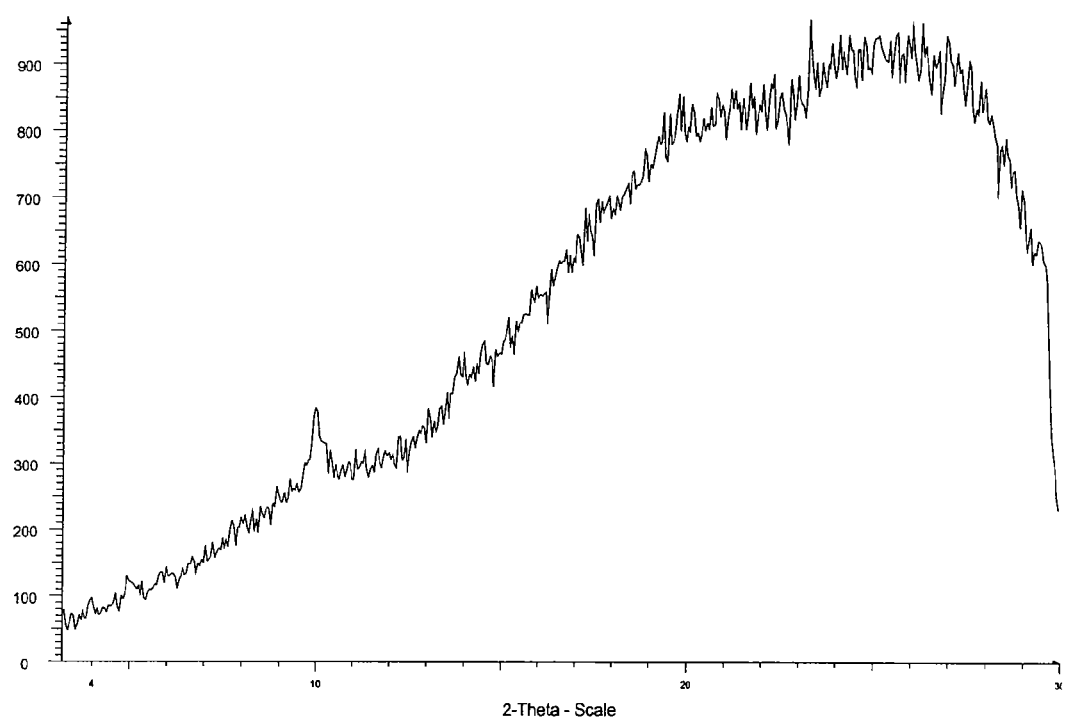
Figure 4 XRPD of [4-(6-fluoro-7-methylamino-2,4-dioxo-1,4-dihydro-2H-quinazolin-3-yl)-phenyl]-5-chloro-thiophen-2-yl-sulfonylurea sodium salt

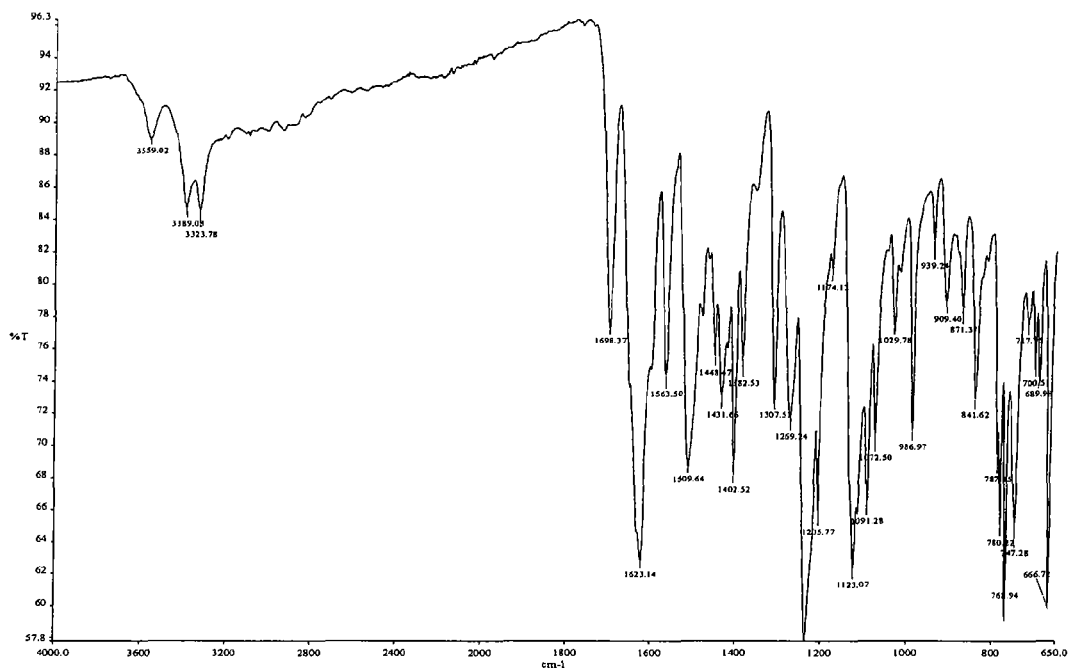
Figure 5 FT-IR of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate (Form A)

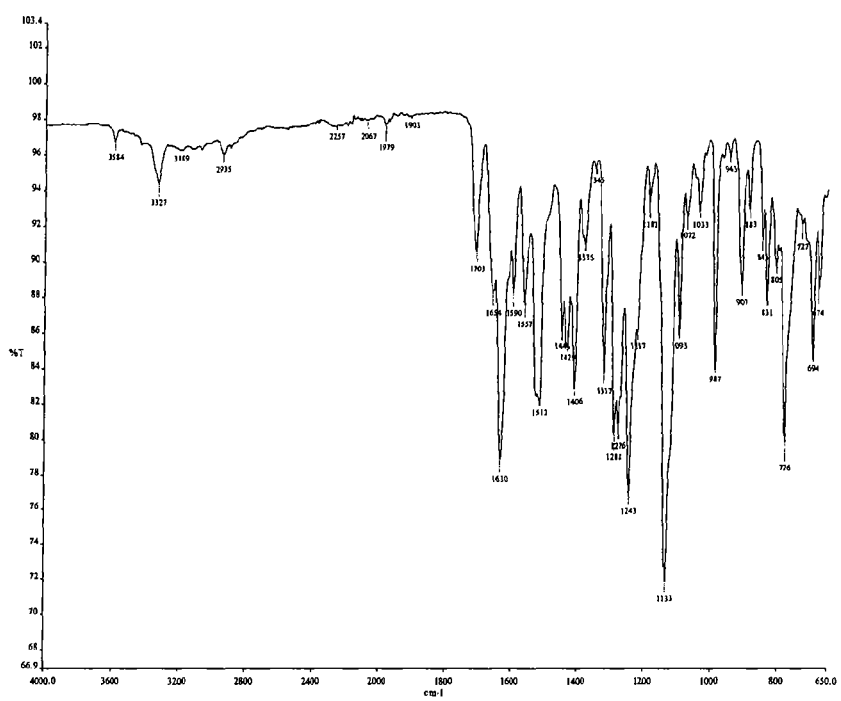
Figure 6 FT-IR of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate (Form B)

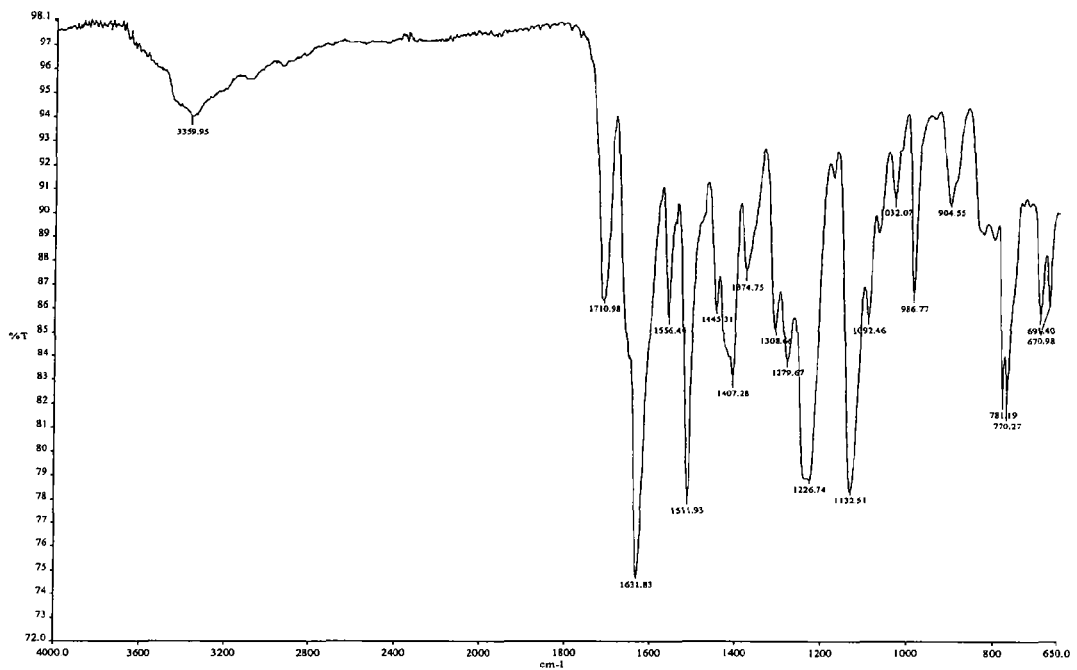
Figure 7 FT-IR of [4-(6-fluoro-7-methylamino-2,4-dioxo-1,4-dihydro-2H-quinazolin-3-yl)-phenyl]-5-chloro-thiophen-2-yl-sulfonylurea sodium salt

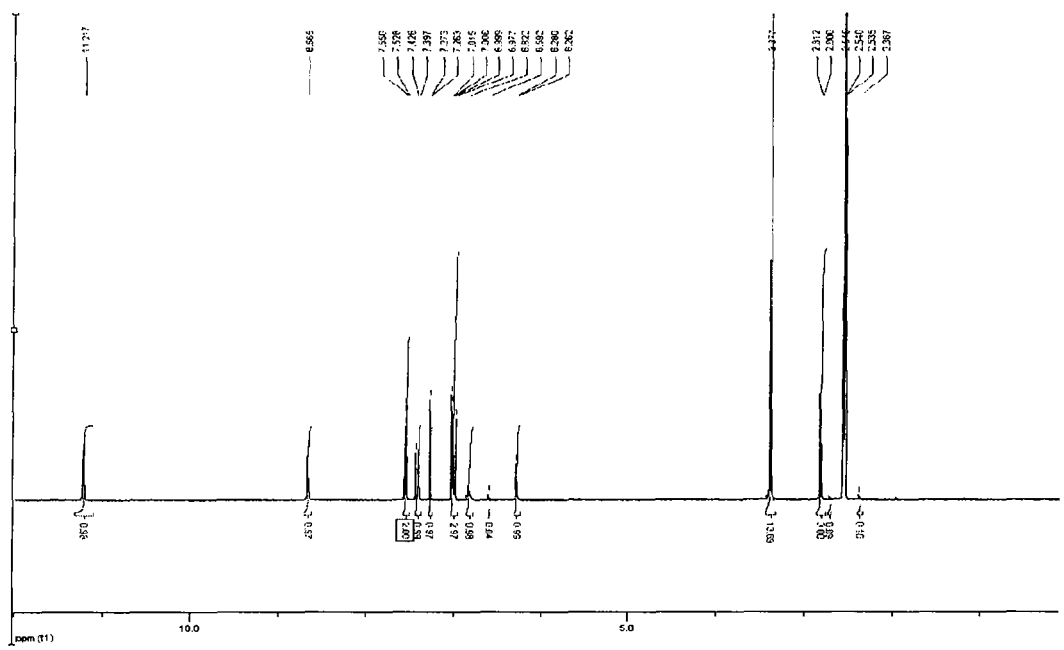
Figure 8 ¹H NMR of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate (Form A)

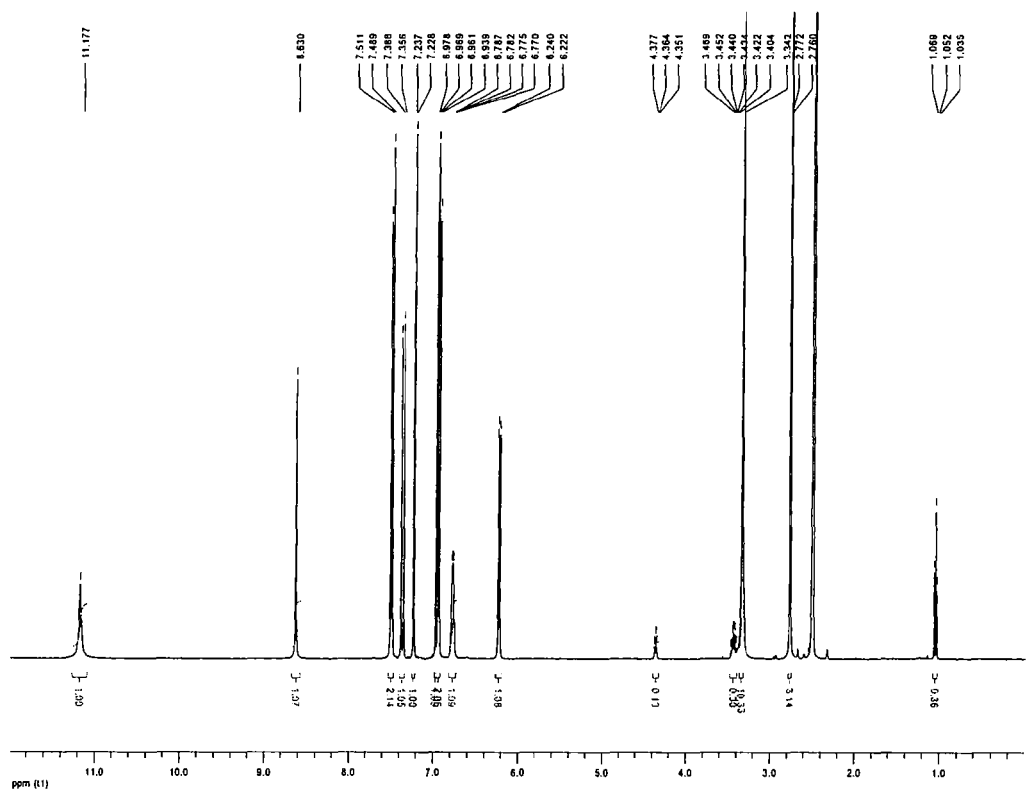
Figure 9 $^1$H NMR of [4-(6-fluoro-7-methylamino-2,4-dioxo-1,4-dihydro-2H-quinazolin-3-yl)-phenyl]-5-chloro-thiophen-2-yl-sulfonylurea potassium salt (Form B)

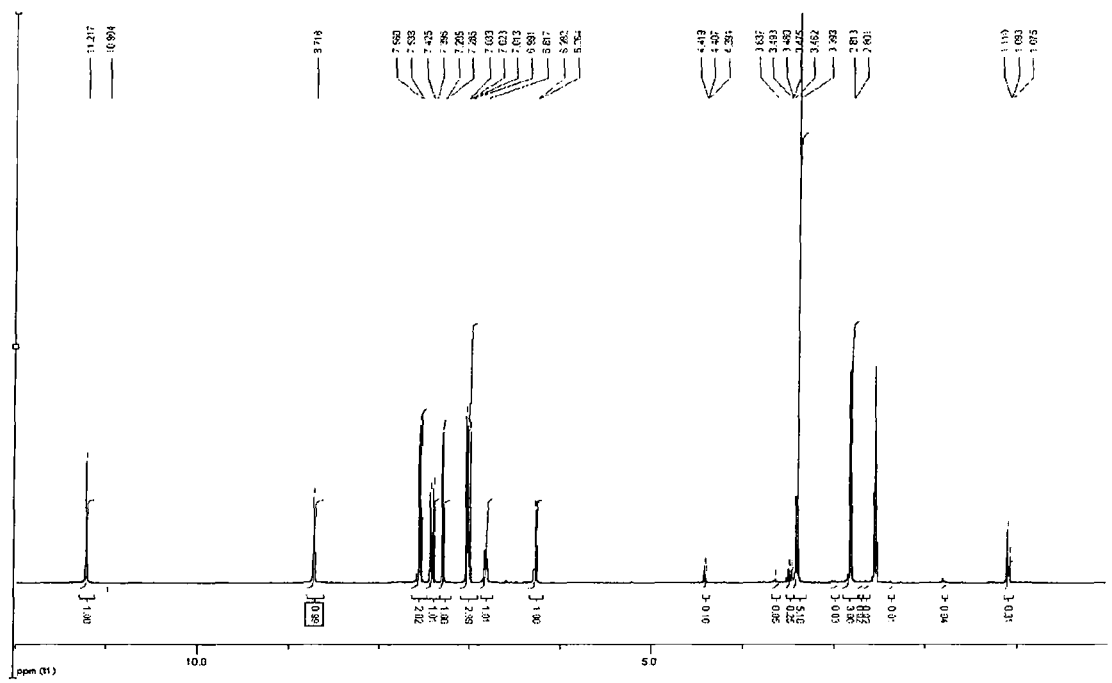
Figure 10 $^1$H NMR of [4-(6-fluoro-7-methylamino-2,4-dioxo-1,4-dihydro-2H-quinazolin-3-yl)-phenyl]-5-chloro-thiophen-2-yl-sulfonylurea sodium salt
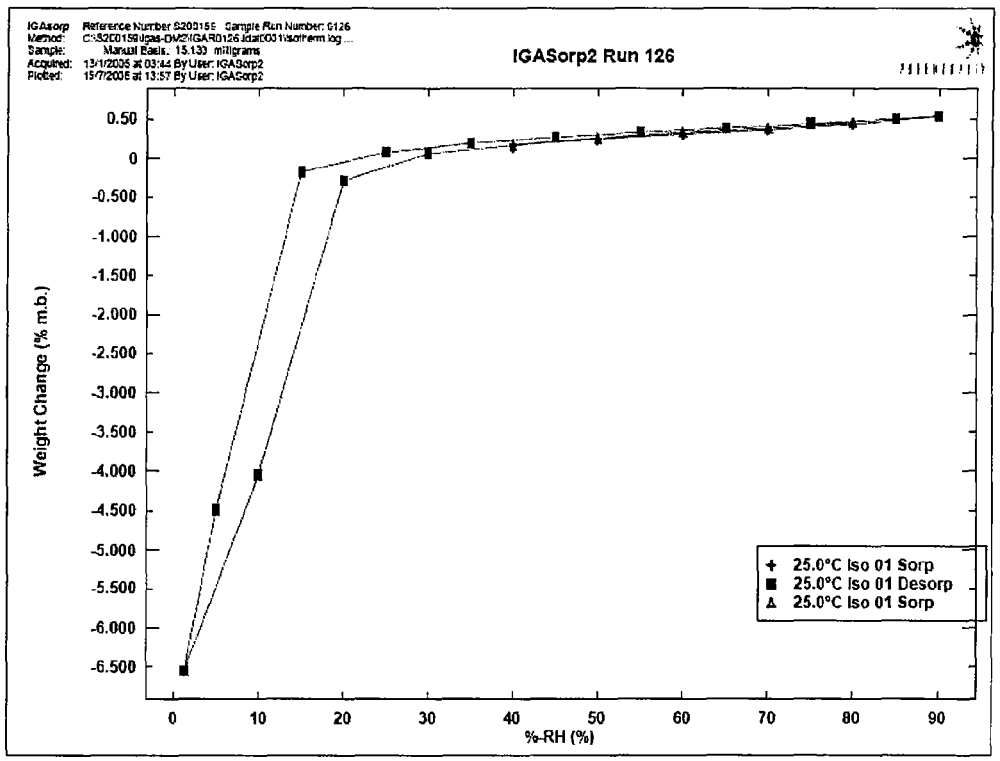
Figure 11 GVS of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate (Form A)

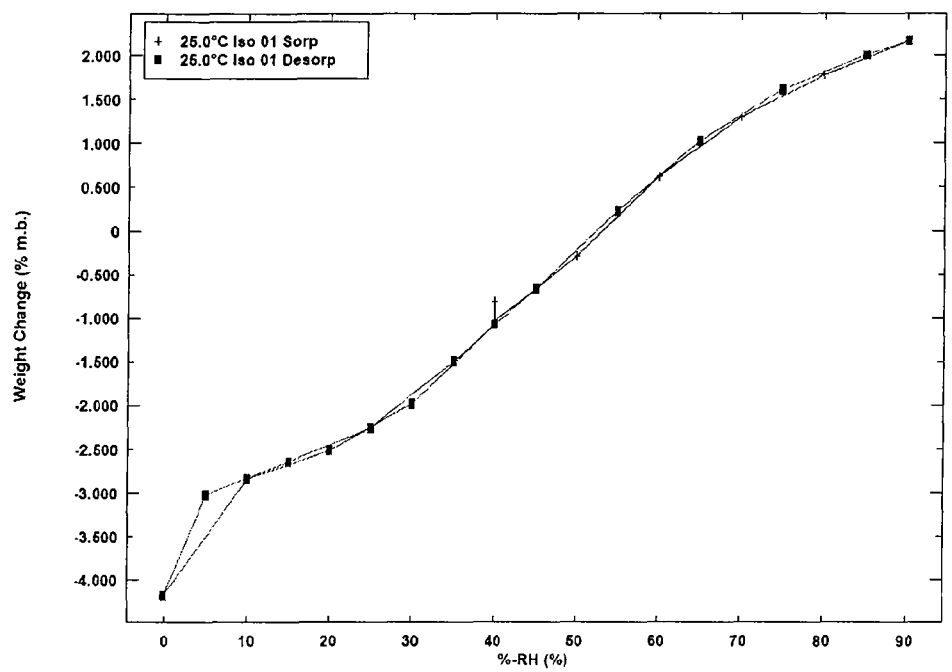
Figure 12a GVS of [4-(6-fluoro-7-methylamino-2,4-dioxo-1,4-dihydro-2H-quinazolin-3-yl)-phenyl]-5-chloro-thiophen-2-yl-sulfonylurea potassium salt (Form B)

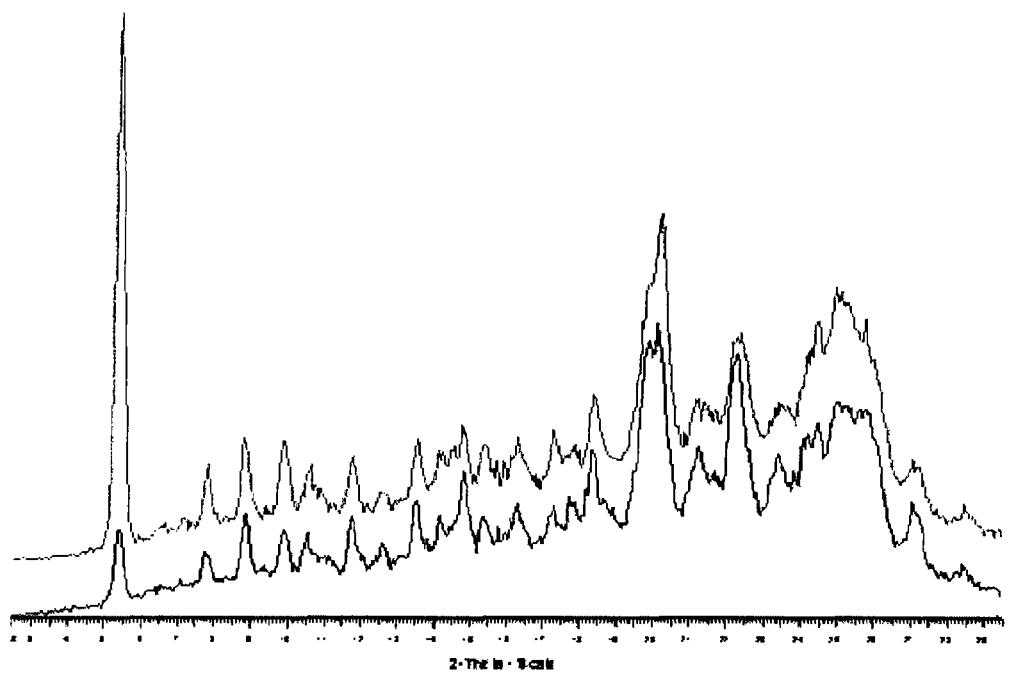
Figure 12b Phase change over the course of the GVS experiment of [4-(6-fluoro-7-methylamino-2,4-dioxo-1,4-dihydro-2H-quinazolin-3-yl)-phenyl]-5-chloro-thiophen-2-yl-sulfonylurea potassium salt (Form B)

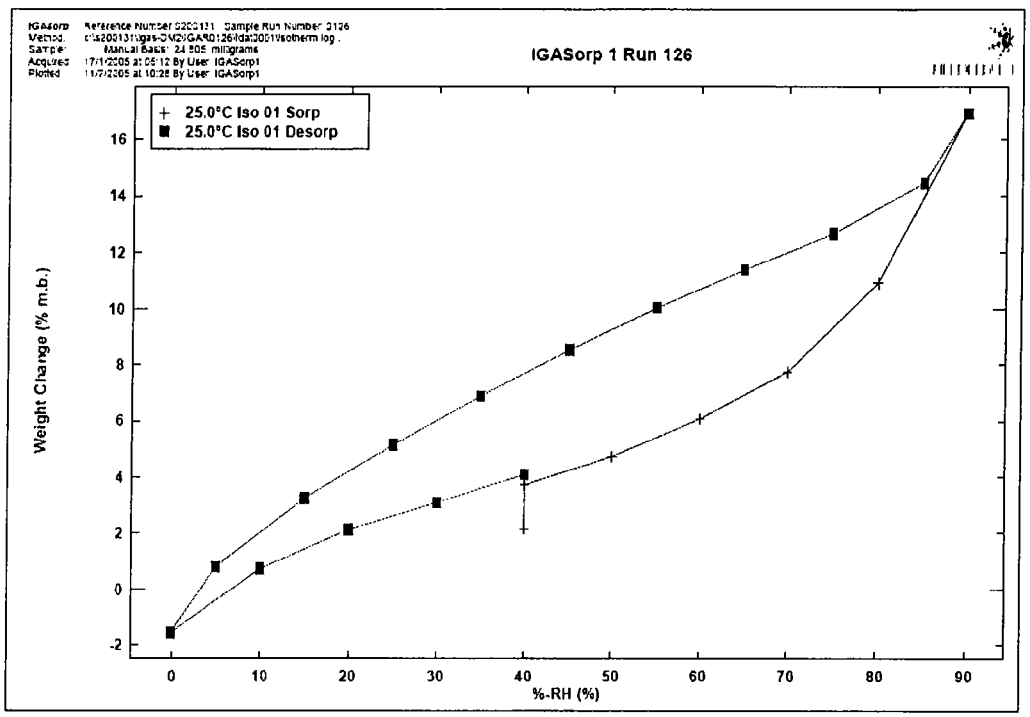
Figure 13 GVS of [4-(6-fluoro-7-methylamino-2,4-dioxo-1,4-dihydro-2H-quinazolin-3-yl)-phenyl]-5-chloro-thiophen-2-yl-sulfonylurea sodium salt

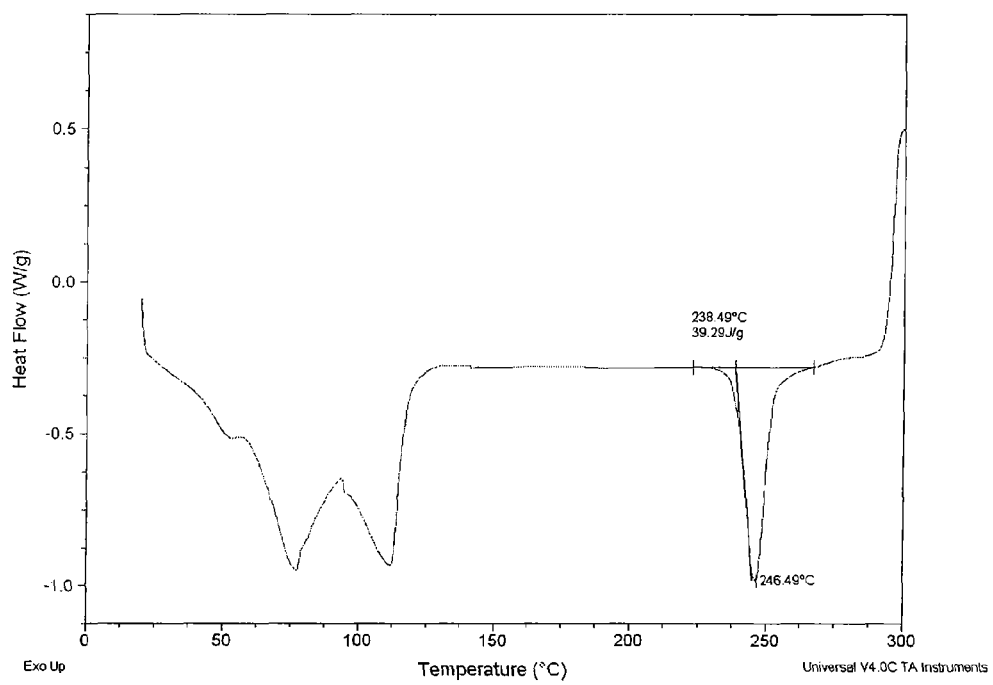
Figure 14 DSC data of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate (Form A)

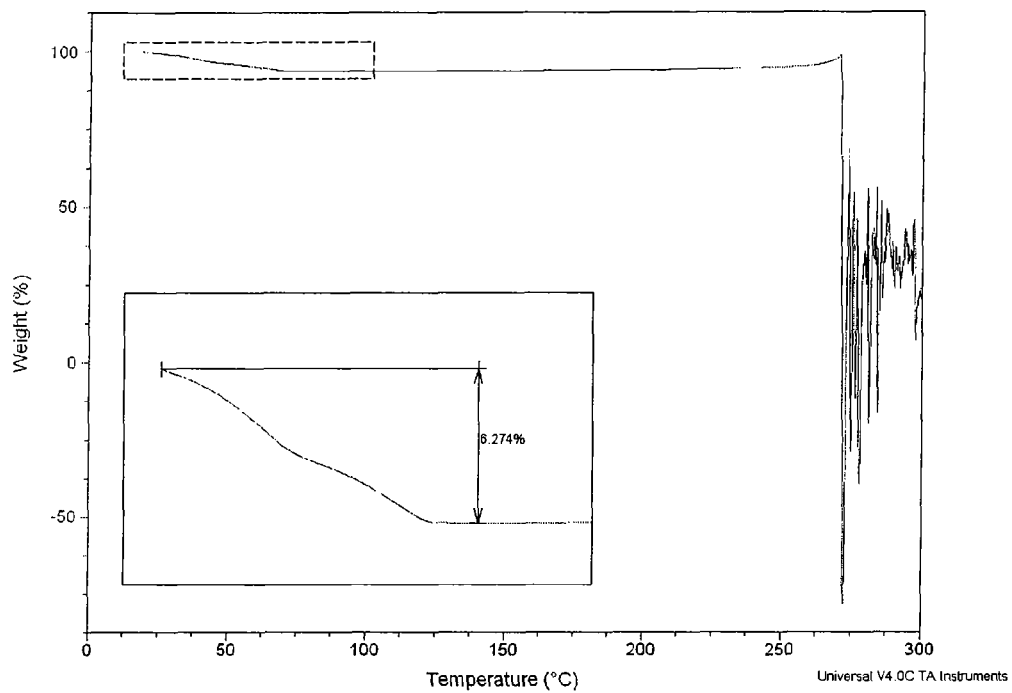
Figure 15 TGA data of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate (Form A)
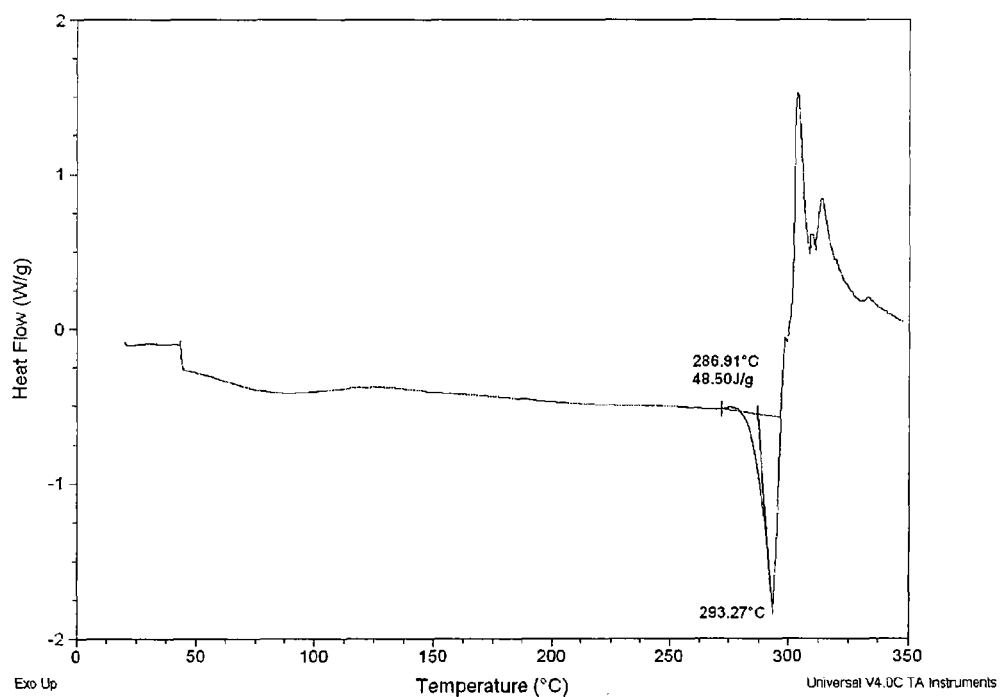
Figure 16 DSC data of [4-(6-fluoro-7-methylamino-2,4-dioxo-1,4-dihydro-2H-quinazolin-3-yl)-phenyl]-5-chloro-thiophen-2-yl-sulfonylurea potassium salt (Form B)

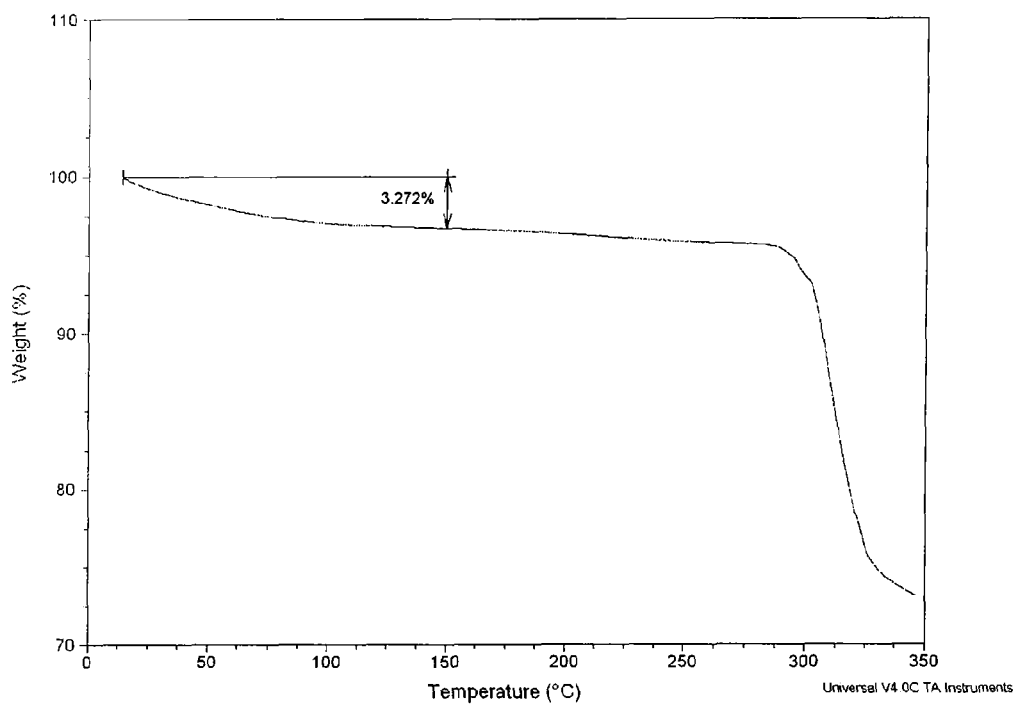
Figure 17 TGA data of [4-(6-fluoro-7-methylamino-2,4-dioxo-1,4-dihydro-2H-quinazolin-3-yl)-phenyl]-5-chloro-thiophen-2-yl-sulfonylurea potassium salt (Form B)

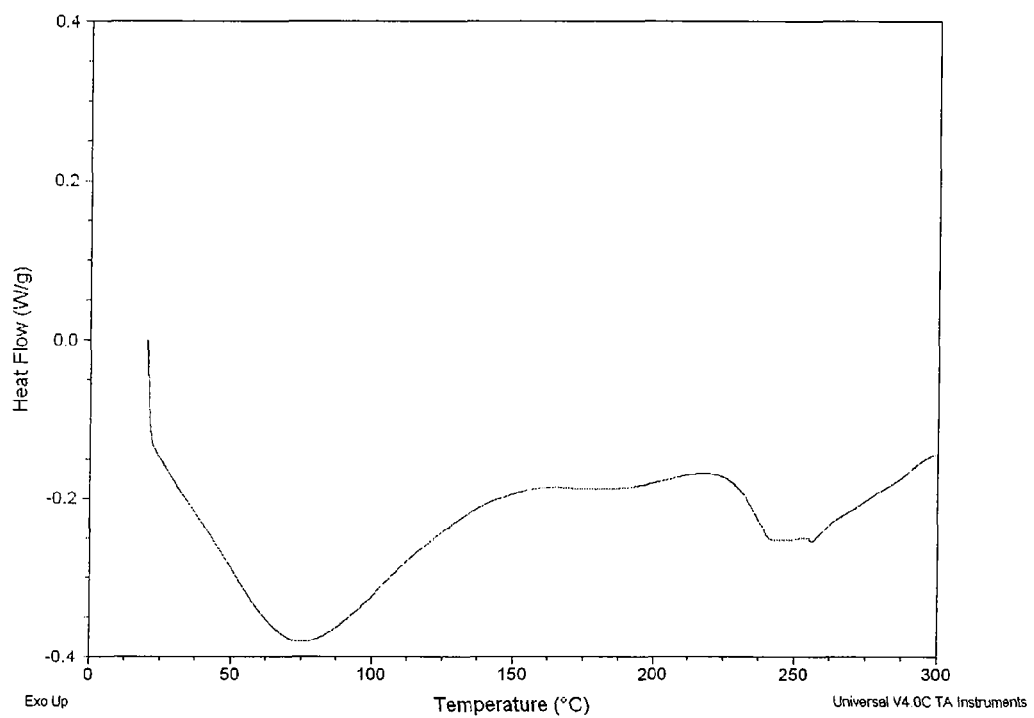
Figure 18 DSC data of [4-(6-fluoro-7-methylamino-2,4-dioxo-1,4-dihydro-2H-quinazolin-3-yl)-phenyl]-5-chloro-thiophen-2-yl-sulfonylurea sodium salt

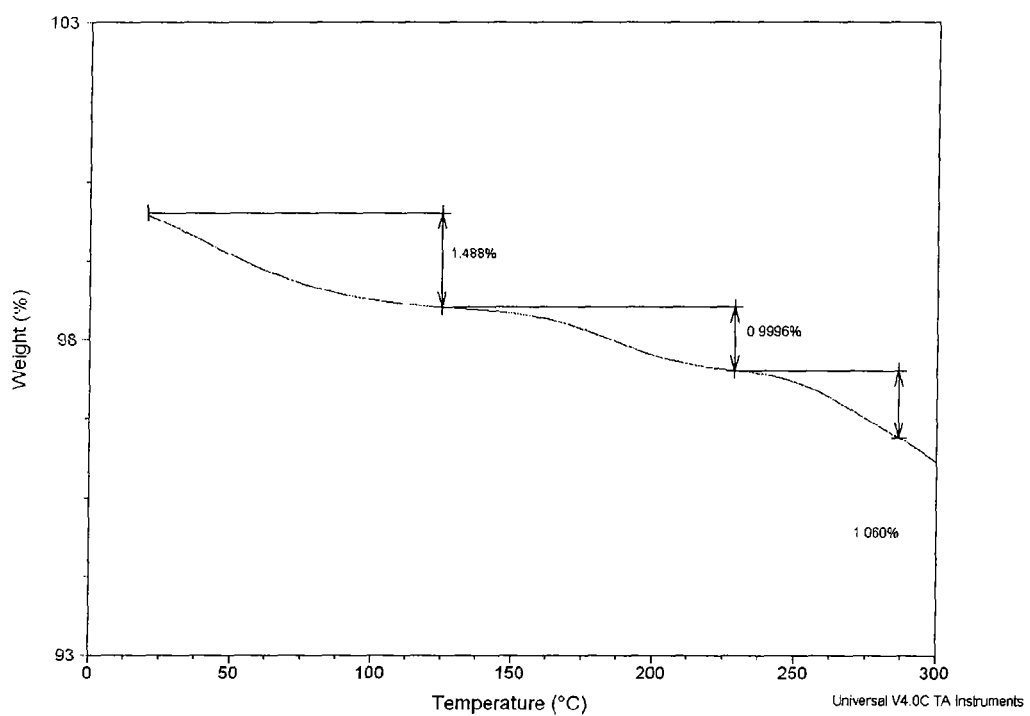
Figure 19 TGA data of [4-(6-fluoro-7-methylamino-2,4-dioxo-1,4-dihydro-2H-quinazolin-3-yl)-phenyl]-5-chloro-thiophen-2-yl-sulfonylurea sodium salt

[4-(6-HALO-7-SUBSTITUTED-2,4-DIOXO-1,4-DIHYDRO-2H-QUINAZOLIN-3-YL)-PHENYL]-5-CHLORO-THIOPHEN-2-YL-SULFONYLUREAS AND FORMS AND METHODS RELATED THERETO

CROSS-REFERENCES TO RELATED APPLICATIONS

This application claims the benefit of U.S. Patent Application No. 60/733,650, filed Nov. 3, 2005, the content of which are incorporated herein by reference.

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and prostheses, and hypercoagulable states related to genetic predisposition or cancers. It is generally thought that platelet aggregates play a critical role in these events. Blood platelets, which normally circulate freely in the vasculature, become activated and aggregate to form a thrombus from disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) *Thromb. Hemost.* 76:835-856). Therefore, platelet ADP receptors are members of the family of P2 receptors activated by purine and/or pyrimidine nucleotides (King, B. F., Townsend-Nicholson, A. & Burnstock, G. (1998) *Trends Pharmacol. Sci.* 19:506-514).

Recent pharmacological data using selective antagonists suggests that ADP-dependent platelet aggregation requires activation of at least two ADP receptors (Kunapuli, S. P. (1998), *Trends Pharmacol Sci.* 19:391-394; Kunapuli, S. P. & Daniel, J. L. (1998) *Biochem. J.* 336:513-523; Jantzen, H. M. et al. (1999) *Thromb. Hemost.* 81:111-117). One receptor appears to be identical to the cloned $P2Y_1$ receptor, mediates phospholipase C activation and intracellular calcium mobilization and is required for platelet shape change. The second platelet ADP receptor important for aggregation mediates inhibition of adenylyl cyclase. Based on its pharmacological and signaling properties this receptor has been provisionally termed $P2Y_{ADP}$ (Fredholm, B. B. et al. (1997) *TIPS* 18:79-82), $P2T_{AC}$ (Kunapuli, S. P. (1998), *Trends Pharmacol. Sci.* 19:391-394) or P2Ycyc (Hechier, B. et al. (1998) *Blood* 92, 152-159). More recently, molecular cloning of this receptor (Hollopeter, G. et al. (2001) *Nature* 409: 202-207) has revealed that it is a new member of the G-protein coupled family and is the target of the thienopyridine drugs ticlopidine and clopidogrel. The nomenclature given to this receptor is $P2Y_{12}$.

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) *Circulation* 100:1667-1667). Some purine derivatives of the endogenous antagonist ATP, e.g., AR-C (formerly FPL or ARL) 67085MX and AR-C69931Mx, are selective platelet ADP receptor antagonists which inhibit ADP-dependent platelet aggregation and are effective in animal thrombosis models (Humphries et al. (1995), *Trends Pharmacol. Sci.* 16, 179; Ingall, A. H. et al. (1999) *J. Med. Chem.* 42, 213-230). Novel triazolo [4,5-d]pyrimidine compounds have been disclosed as $P_{2T}$-antagonists (WO 99/05144). Tricyclic compounds as platelet ADP receptor inhibitors have also been disclosed in WO 99/36425. The target of these antithrombotic compounds appears to be $P_2Y_{12}$, the platelet ADP receptor mediating inhibition of adenylyl cyclase.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

In addition, while biological activity is a sine non qua for an effective drug, the compound must be capable of large scale manufacturing and the physical properties of the compound can markedly impact the effectiveness and cost of a formulated active ingredient. Salts of acidic and basic compounds can alter or improve the physical properties of a parent compound. These salt forming agents, however, must be identified empirically by the pharmaceutical chemist since there is no reliable method to predict the influence of a salt species on the behavior of a parent compound in dosage forms. Effective screening techniques, which potentially could simplify the selection process, are unfortunately absent (G. W. Radebaugh and L. J. Ravin Preformulation. In, *Remington: The Science and Practice of Pharmacy*; A. R. Gennaro Ed.; Mack Publishing Co. Easton, Pa., 1995; pp 1456-1457).

Amorphous and different crystalline solid/polymorphic forms of salts are frequently encountered among pharmaceutically useful compounds. Polymorphism is the ability of any element or compound to crystallize as more than one distinct crystalline species. Physical properties including solubility, melting point/endotherm maximum, density, hardness, crystalline shape and stability can be quite different for different forms of the same chemical compound.

Crystalline solid and amorphous forms may be characterized by scattering techniques, e.g., x-ray diffraction powder pattern, by spectroscopic methods, e.g., infra-red, solid state $^{13}C$ and $^{19}F$ nuclear magnetic resonance spectroscopy and by thermal techniques, e.g. differential scanning calorimetry or differential thermal analysis. Although the intensities of peaks in the x-ray powder diffraction patterns of different batches of a compound may vary slightly, the peaks and the peak locations are characteristic for a specific crystalline solid or amorphous form. Additionally, infrared, Raman and thermal methods have been used to analyze and characterize crystalline and solid amorphous forms. Solid and amorphous forms may be characterized by data from the X-ray powder diffraction pattern determined in accordance with procedures which are known in the art (see J. Haleblian, *J. Pharm. Sci.* 1975 64:1269-1288, and J. Haleblain and W. McCrone, *J. Pharm. Sci.* 1969 58:911-929). Although the intensities of peaks in the x-ray powder diffraction patterns of different batches of the compounds may vary slightly, the peaks and the peak locations are characteristic for a specific crystalline solid form.

The problem which must be solved is to identify a suitable salt and form which (i) possesses adequate chemical stability during the manufacturing process, (ii) is efficiently prepared, purified and recovered, (ii) provides acceptable solubility in pharmaceutically acceptable solvents, (iii) is amenable to manipulation (e.g. flowability and particle size) and formulation with negligible decomposition or change of the physical and chemical characteristics of the compound, (iv) exhibits acceptable chemical stability in the formulation. In addition, salts and forms containing a high molar percent of the active ingredient are highly desirable since they minimize the quantity of material which must be formulated and administered to produce a therapeutically effective dose. These often conflicting requirements make identification suitable salts a challenging and important problem which must be solved by the skilled pharmaceutical scientist before drug development can proceed in earnest.

Therefore, there is a need for compounds and salts and amorphous and crystalline solid forms of these compounds of the invention and an efficient process for producing the compounds, salts and crystalline solid forms of the compounds of the invention. Solutions to the above difficulties and deficiencies are needed before compounds become effective for routine treatment of thrombosis.

Polyaryl compounds generally are highly crystalline, poorly water soluble and hydrophobic, resulting in difficulties in the preparation of pharmaceutical formulations and problems associated with bioavailability. Accordingly, efforts were made to discover other forms of compounds of the invention and to investigate the properties thereof. There were discovered crystalline solid forms of salts of compounds of the invention. The present invention fulfills the above needs by providing polymorphs and methods for treating and preventing thrombosis, while presenting a better adverse effect profile.

SUMMARY OF THE INVENTION

In one aspect, the present invention provides compounds having the formula (I):

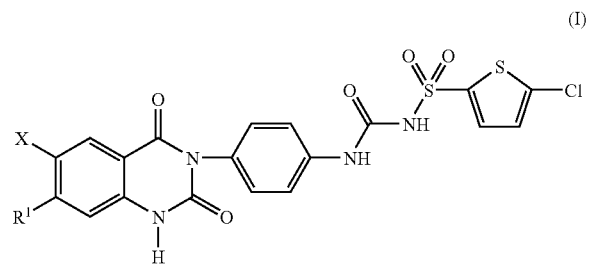

(I)

wherein:
R$^1$ is selected from the group consisting of H, halogen, —OH, —C$_{1-10}$-alkyl and C$_{1-6}$-alkylamino; and
X is selected from the group consisting of: F and I.

The invention also covers all pharmaceutically acceptable derivatives of the compounds of formula (I).

In another aspect, the invention provides crystalline solid and amorphous forms of the potassium and sodium salts of [4-(6-fluoro-7-methylamino-2,4-dioxo-1,4-dihydro-2H-quinazolin-3-yl)-phenyl]-5-chloro-thiophen-2-yl-sulfonylurea.

In another aspect, the invention provides pharmaceutical compositions for preventing or treating thrombosis and thrombosis related conditions in a mammal. The compositions contain a therapeutically effective amount of one or more compounds of formula (I) or a pharmaceutically acceptable salt thereof and a pharmaceutically acceptable carrier or excipient. The invention further provides a method for preventing or treating thrombosis and thrombosis related conditions in a mammal by administering a therapeutically effective amount of a compound of formula (I) or a pharmaceutically acceptable salt thereof.

In still another aspect, the present invention provides methods for preparing compounds of formula (I), their crystalline solid and amorphous forms and pharmaceutical compositions for preventing or treating thrombosis and thrombosis related conditions in a mammal.

BRIEF DESCRIPTION OF THE DRAWINGS

FIG. 1 provides structure of [4-(6-fluoro-7-methylamino-2,4-dioxo-1,4-dihydro-2H-quinazolin-3-yl)-phenyl]-5-chloro-thiophen-2-yl-sulfonylurea potassium and/or sodium salt.

FIG. 2a shows an X-ray powder diffraction (XRPD) of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate. FIG. 2b shows an XRPD of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate showing peak information.

FIG. 3a shows an XRPD of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt. FIG. 3b shows an XRPD of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt showing peak information.

FIG. 4 shows an XRPD of the amorphous form of [4-(6-fluoro-7-methylamino-2,4-dioxo-1,4-dihydro-2H-quinazolin-3-yl)-phenyl]-5-chloro-thiophen-2-yl-sulfonylurea sodium salt.

FIG. 5 shows a Fourier-transformed infrared spectra (FT-IR) of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate.

FIG. 6 shows a Fourier-transformed infrared spectra (FT-IR) of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate.

FIG. 7 shows the FT-IR of an amorphous form of [4-(6-fluoro-7-methylamino-2,4-dioxo-1,4-dihydro-2H-quinazolin-3-yl)-phenyl]-5-chloro-thiophen-2-yl-sulfonylurea sodium salt.

FIG. 8 shows the $^1$H-NMR of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate.

FIG. 9 shows the ¹H-NMR of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt.

FIG. 10 shows the ¹H-NMR of amorphous form of [4-(6-fluoro-7-methylamino-2,4-dioxo-1,4-dihydro-2H-quinazolin-3-yl)-phenyl]-5-chloro-thiophen-2-yl-sulfonylurea sodium salt.

FIG. 11 provides the gravimetric vapour sorption (GVS) data of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate.

FIG. 12a provides the gravimetric vapour sorption (GVS) data of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate. The sample was recovered after the completion of the GVS experiment and re-examined by XRPD. The results (FIG. 12b) show that no phase change has occurred over the course of the GVS experiment. The change in intensity of the peak at ca. 5.4°2θ, is a preferred orientation effect.

FIG. 13 provides the gravimetric vapour sorption (GVS) data of amorphous form of [4-(6-fluoro-7-methylamino-2,4-dioxo-1,4-dihydro-2H-quinazolin-3-yl)-phenyl]-5-chloro-thiophen-2-yl-sulfonylurea sodium salt.

FIG. 14 provides the differential scanning calorimetry (DSC) data of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate.

FIG. 15 provides the TGA data of crystalline solid form A of [4-(6-fluoro-7-methylamino-2,4-dioxo-1,4-dihydro-2H-quinazolin-3-yl)-phenyl]-5-chloro-thiophen-2-yl-sulfonylurea potassium salt dihydrate.

FIG. 16 provides the DSC data of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt.

FIG. 17 provides the TGA data of crystalline solid form B of [4-(6-fluoro-7-methylamino-2,4-dioxo-1,4-dihydro-2H-quinazolin-3-yl)-phenyl]-5-chloro-thiophen-2-yl-sulfonylurea potassium salt.

FIG. 18 provides the DSC data of amorphous form of [4-(6-fluoro-7-methylamino-2,4-dioxo-1,4-dihydro-2H-quinazolin-3-yl)-phenyl]-5-chloro-thiophen-2-yl-sulfonylurea sodium salt.

FIG. 19 provides the TGA data of amorphous form of [4-(6-fluoro-7-methylamino-2,4-dioxo-1,4-dihydro-2H-quinazolin-3-yl)-phenyl]-5-chloro-thiophen-2-yl-sulfonylurea sodium salt.

DETAILED DESCRIPTION OF THE INVENTION

The present invention involves sulfonylurea compounds and their derivatives and crystalline solid and amorphous forms thereof, and their preparation. The potassium salt of [4-(6-fluoro-7-methylamino-2,4-dioxo-1,4-dihydro-2H-quinazolin-3-yl)-phenyl]-5-chloro-thiophen-2-yl-sulfonylurea has excellent crystallinity, stability and purity. The compounds of the present invention are useful for the treatment and prevention of undesired thrombosis and thrombosis related conditions in mammals.

I. Definitions

In accordance with the present invention and as used herein, the following terms are defined with the following meanings, unless explicitly stated otherwise.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "about" as used herein means variation one might see in measurements taken among different instruments, samples, and sample preparations. Such variation may include, for instance, colligative properties for thermal measurements. Typical variation among different x-ray diffractometers and sample preparations for crystalline solid forms is on the order of 0.2°2θ. Typical variation for Raman and IR spectrometers is on the order of twice the resolution of the spectrometer. The resolution of the spectrometer used was about 2 cm⁻¹.

The term "solvate" as used herein means a compound of the invention or a salt, thereof, that further includes a stoichiometric or non-stoichiometric amount of a solvent bound by non-covalent intermolecular forces in an amount of greater than about 0.3% when prepared according to the invention.

The term "hydrate" as used herein means a compound of the invention or a salt thereof, that further includes a stoichiometric or non-stoichiometric amount of water bound by non-covalent intermolecular forces. Hydrates are formed by the combination of one or more molecules of water with one of the substances in which the water retains its molecular state as $H_2O$, such combination being able to form one or more hydrate.

The term "anhydrous" as used herein means a compound of the invention or a salt thereof that contains less than about 3% by weight water or solvent when prepared according to the invention.

The term "drying" as used herein means a method of removing solvent and/or water from a compound of the invention which, unless otherwise specified, may be done at atmospheric pressure or under reduced pressure and with or without heating until the level of solvent and/or water contained reached an acceptable level.

The term "polymorphs" as used herein means crystal structures in which a compound can crystallize in different crystal packing arrangements, all of which have the same elemental composition. Different crystal forms usually have different X-ray diffraction patterns, infrared spectra, melting points/endotherm maximums, density hardness, crystal shape, optical and electrical properties, stability and solubility. Recrystallization solvent, rate of crystallization, storage temperature, and other factors may cause one crystal form to dominate.

The term "solid form" as used herein means crystal structures in which compounds can crystallize in different packing arrangements. Solid forms include polymorphs, hydrates, and solvates as those terms are used in this invention. Different solid forms, including different polymorphs, of the same compound exhibit different x-ray powder diffraction patterns and different spectra including infra-red, Raman, and solid-state NMR. Their optical, electrical, stability, and solubility properties may also differ.

The term "characterize" as used herein means to select data from an analytical measurement such as X-ray powder diffraction, infra-red spectroscopy, Raman spectroscopy, and/or solid-state NMR to distinguish one solid form of a compound from other solid forms of a compound.

The term "mammal" includes, without limitation, humans, domestic animals (e.g., dogs or cats), farm animals (cows, horses, or pigs), monkeys, rabbits, mice, and laboratory animals.

The term "alkyl" refers to saturated aliphatic groups including straight-chain, branched-chain and cyclic groups having the number of carbon atoms specified, or if no number is specified, having up to about 12 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. For brevity, the term $C_{1-6}$alkylamino is meant to include straight chain, branched or cyclic alkyl groups or combinations thereof, such as methyl, ethyl, 2-methylpropyl, cyclobutyl and cyclopropylmethyl.

The term "$C_1$-$C_6$ alkylamino" or "$C_{1-6}$ alkylamino" as used herein refers to an amino moiety attached to the remainder of the molecule whereby the nitrogen is substituted with one or two $C_{1-6}$ alkyl substituents, as defined above.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "pharmaceutically acceptable derivatives" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include those derived from inorganic bases such as sodium, potassium, lithium, ammonium, calcium, magnesium, iron, zinc, copper, manganese, aluminum salts and the like. Particularly preferred are the potassium and sodium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic nontoxic bases are isopropylamine, diethylamine, ethanolamine, trimethamine, dicyclohexylamine, choline, and caffeine. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19; Bundgaard, H., ed., *Design of Prodrugs* (Elsevier Science Publishers, Amsterdam 1985)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the term "pharmaceutically acceptable derivatives" is meant to include compounds which are in a prodrug form. "Prodrugs" of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent (see Bundgaard, H., ed., *Design of Prodrugs* (Elsevier Science Publishers, Amsterdam 1985)).

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., supra. These esters are typically formed from the corresponding carboxylic acid and an alcohol. Generally, ester formation can be accomplished via conventional synthetic techniques. (See, e.g., March *Advanced Organic Chemistry,* 3rd Ed., p. 1157 (John Wiley & Sons, New York 1985) and references cited therein, and Mark et al., *Encyclopedia of Chemical Technology,* (1980) John Wiley & Sons, New York). The alcohol component of the ester will generally comprise: (i) a $C_2$-$C_{12}$ aliphatic alcohol that can or can not contain one or more double bonds and can or can not contain branched carbons; or (ii) a $C_7$-$C_{12}$ aromatic or heteroaromatic alcohols. The present invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see, Bundgaard, H., ed., supra. These amides are typically formed from the corresponding carboxylic acid and an amine. Generally, amide formation can be accomplished via conventional synthetic techniques. See, e.g., March et al., *Advanced Organic Chemistry,* 3rd Ed., p. 1152 (John Wiley & Sons, New York 1985), and Mark et al., *Encyclopedia of Chemical Technology,* (John Wiley & Sons, New York 1980). The present invention also contemplates the use of those compositions which are both amides as described herein and at the same time are the pharmaceutically acceptable acid addition salts thereof.

The term "pharmaceutically acceptable derivatives" is also meant to include compounds of the present invention which can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

As used herein, the term "treating" refers to providing an appropriate dose of a therapeutic agent to a subject suffering from an ailment.

As used herein, the term "therapeutically effective amount" refers to an amount of a therapeutic agent that is sufficient to affect the treatment of a subject suffering from an ailment.

As used herein, the term "condition" refers to a disease state for which the compounds, compositions and methods of the present invention are being used against.

As used herein, the term "ADP-mediated disease or condition" and the like refers to a disease or condition characterized by less than or greater than normal, ADP activity. A ADP-mediated disease or condition is one in which modulation of ADP results in some effect on the underlying condition or disease (e.g., a ADP inhibitor or antagonist results in some improvement in patient well-being in at least some patients).

As used herein, the term "blood sample" refers to whole blood taken from a subject, or any fractions of blood including plasma or serum.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

II. Compound Embodiments of the Invention

Compounds of formula (I) below represent one embodiment of the invention:

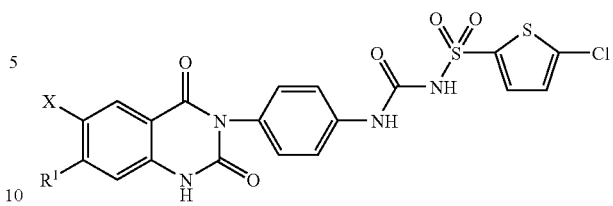

wherein:

X is selected from the group consisting of F and I;

$R^1$ is selected from the group consisting of H, halogen, —OH, —$C_{1-10}$-alkyl and $C_{1-6}$-alkylamino.

The invention also covers all pharmaceutically acceptable derivatives of the compounds of formula I. Pharmaceutically acceptable salts can be prepared using at least one inorganic or organic base including, but not limited to potassium hydride, potassium hydroxide, potassium alkoxides, sodium hydride, sodium hydroxide, sodium alkoxides and the like.

Within the descriptions above are a number of preferred embodiments. In one group of preferred embodiments, $R^1$ is $C_{1-10}$-alkyl or $C_{1-6}$-alkylamino.

In another group of preferred embodiments, $R^1$ is $C_{1-6}$-alkylamino. In yet another group of preferred embodiments, X is F.

A number of specific compounds are among the most preferred embodiments for the compounds of formula I, and are provided in FIG. 1 and also represented below.

In one preferred embodiment of the invention, compounds of formula (I) include the compound having the formula:

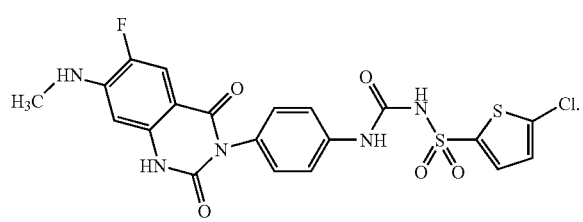

Another group of particularly preferred compounds of the invention have the formula:

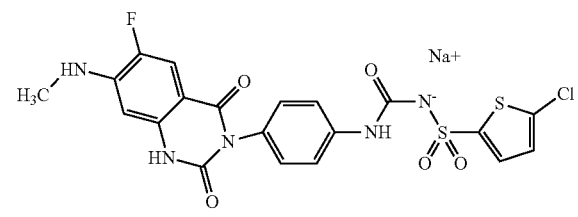

and/or

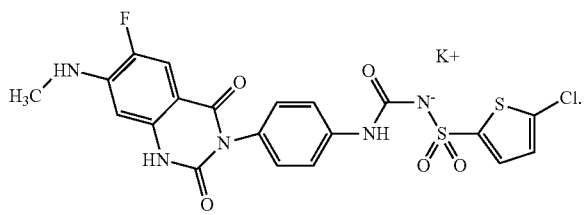

III. Preparation of Compounds of the Invention

Scheme 1 illustrates a method of preparing certain compounds of formula I wherein Ar is phenylene and $R^1$ and $X^1$ are as described above.

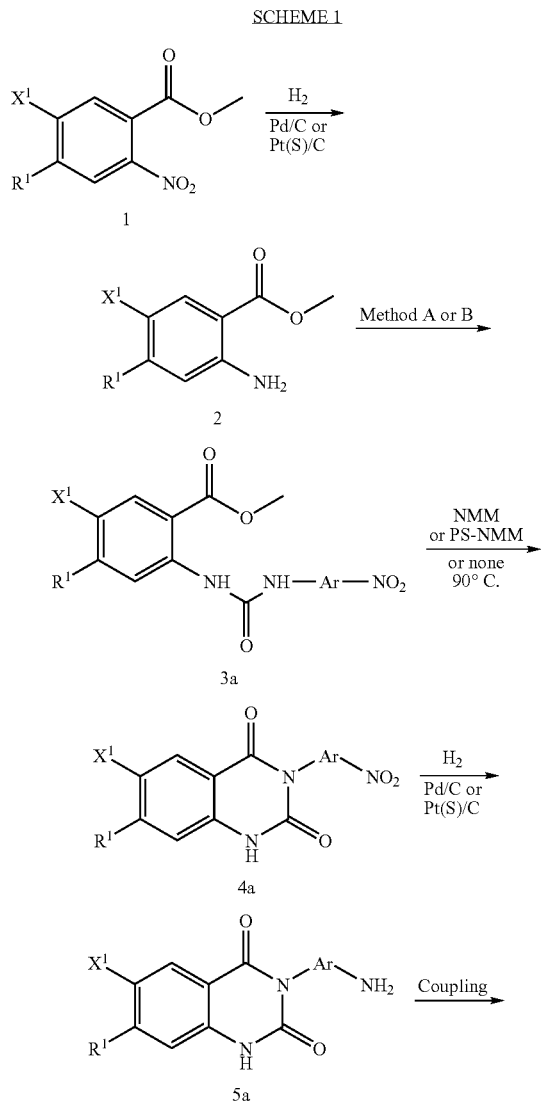

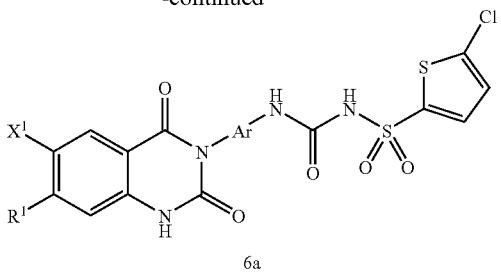

A compound of formula I can be prepared by reducing 2-nitro-benzoic acid methyl ester compound 1 by procedures known to one skilled in the art to yield aniline 2. (See also published patent application U.S. 2002/077486). For example, a method of nitro group reduction can be carried out by hydrogenation. The hydrogenation is carried out with a suitable catalyst (e.g., 10% Pd/C or Pt(s)/C) under hydrogen and in an appropriate solvent, typically in an alcohol, preferably ethanol at room temperature. Treating compound 2 with appropriately substituted aryl isocyanate (Method A) provides intermediate urea 3a. Alternatively, urea 3a can be formed by treating compound 2 with triphosgene in the presence of a base such as triethylamine or diisopropylethylamine in an inert solvent such as THF, dichloromethane and MeCN at appropriate temperature, preferably at 20° C., followed by substituted aniline (Method B). Urea 3a, prepared by Method A or Method B typically without further purification can be subjected to thermal or base (such as N-methyl morpholine (NMM) or polystyrene-NMM (PS-NMM) induced ring closure to provide quinazolinedione 4a. The nitro group of compound 4a can be reduced by procedures known to one skilled in the art to yield free amino group. For example, a method of reduction can be carried out by hydrogenation, with a suitable catalyst (e.g., 10% palladium on carbon) in an appropriate solvent, typically an alcohol. The formation of sulfonylurea linkage can be accomplished by treating the reduced product aniline 5a with a pre-mixed solution of substituted thiophene-2-sulfonamide, N,N'-disuccinimidyl carbonate and tetramethylguanidine in dichloromethane, followed by treatment with TFA in dichloromethane at room temperature to afford the sulfonylurea of formula I. Alternatively, the sulfonylurea linkage can be formed by reacting the aniline 5a and 5-Chloro-thiophene-2-sulfonyl ethylcarbamate in suitable solvents, which include, but are not limited to, toluene, acetonitrile, 1,4-dioxane and DMSO.

Scheme 2 illustrates an alternative method of preparing compounds of Formula I wherein $R^1$ is, for example, alkylamino and $L^1$ is halogen, alkylsulfonate, haloalkylsulfonate and arylsulfonate.

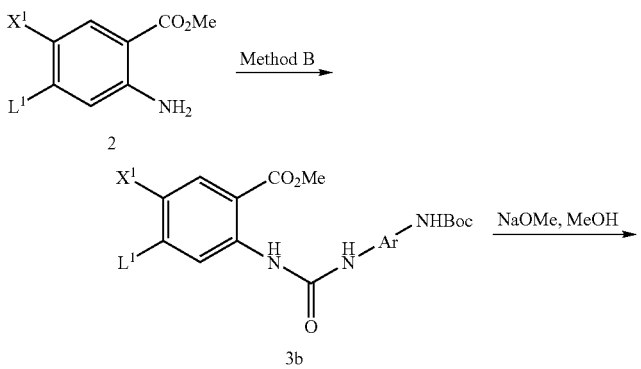

-continued

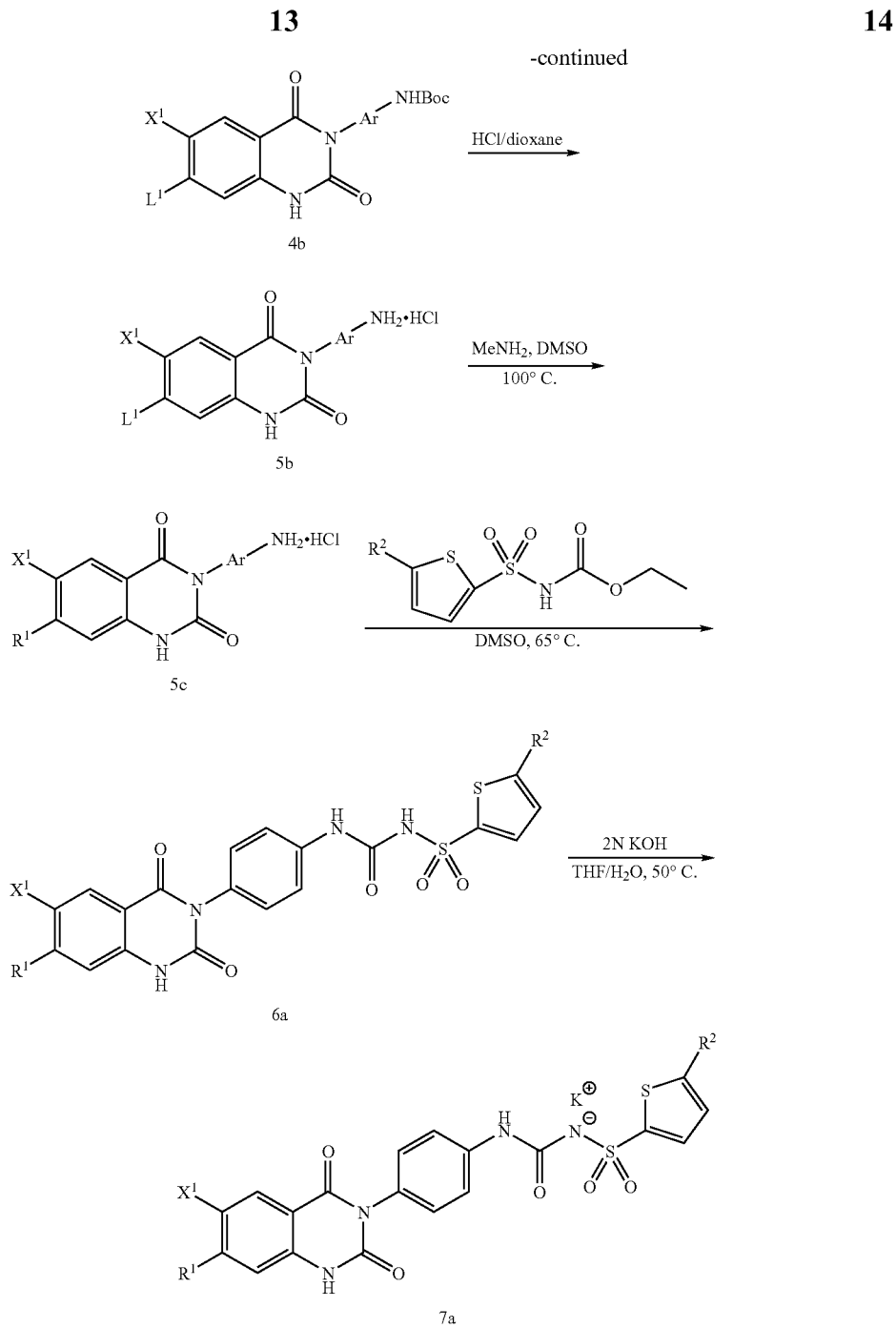

The urea 3b can be prepared by treating compound 2 with triphosgene or p-nitrophenyl chloroformate in the presence of a base, such as triethylamine and/or diisopropylethylamine, in an inert solvent, such as THF, dichloromethane and/or MeCN, at an appropriate temperature, typically at about 20° C., followed by treatment with an appropriately protected aniline (Method B). Urea 3b, typically without further purification, can be subjected to base induced ring closure to provide intermediate quinazolinedione 4b. The protecting group of compound 4b can be removed using standard techniques appropriate for the protecting group used. For example a BOC protecting group can be removed by treating compound 4b with 4N HCl in dioxane. The C-7 fluoro of compound 5b is then displaced by treatment with methylamine in DMSO at about 120° C. to afford aniline 6a. The preparation of target sulfonylurea 7a can be accomplished by treating aniline 6a with 5-chloro-thiophene-2-sulfonyl ethylcarbamate in an appropriate solvent, such as dimethyl sulfoxide, dioxane and/or acetonitrile with heating.

Scheme 3 illustrates an alternative method of preparing compounds of Formula I wherein $R^1$ is, for example, alkylamino and $L^1$ is halogen, alkylsulfonate, haloalkylsulfonate and arylsulfonate and M is K.

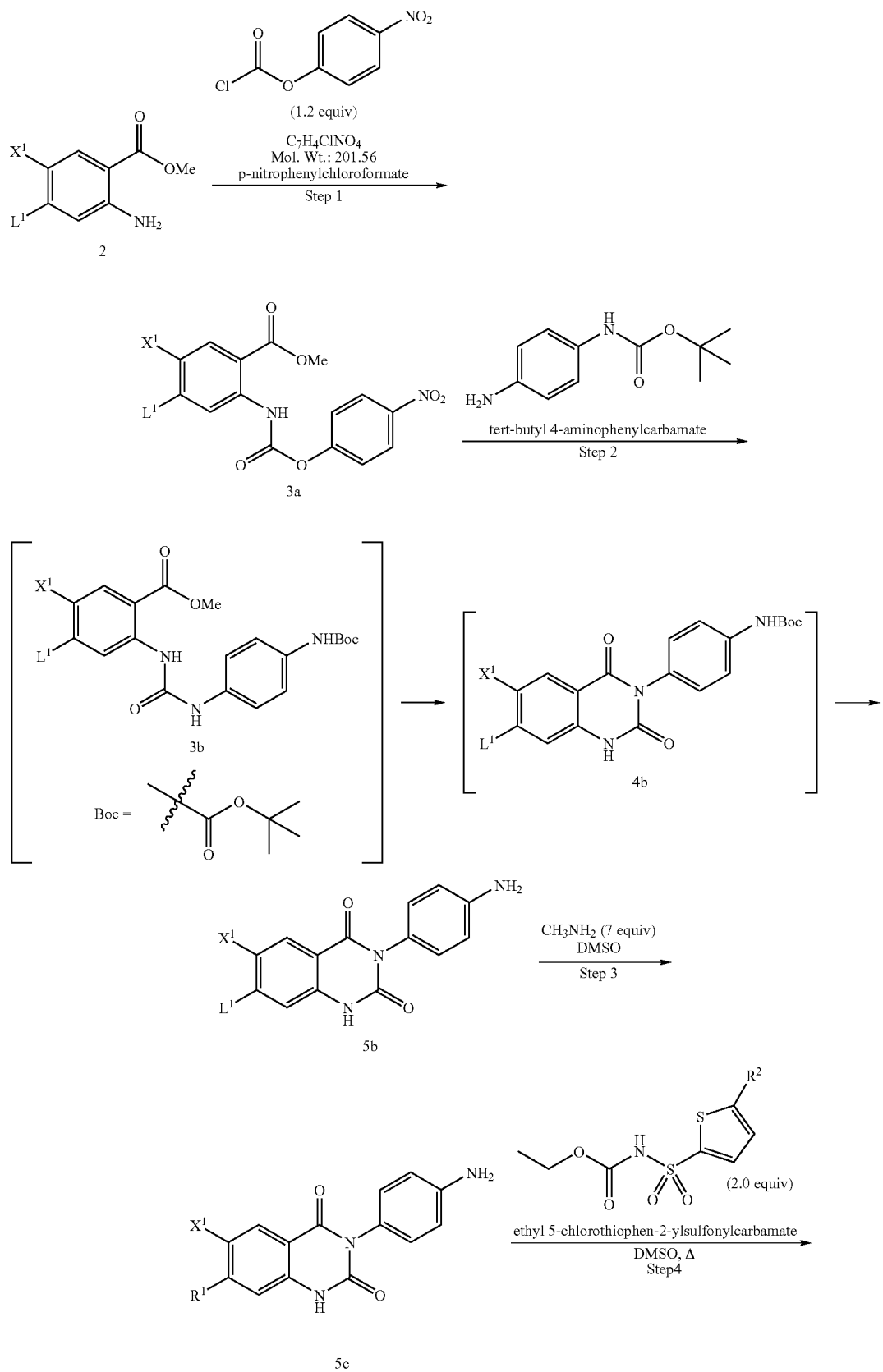
SCHEME 3

-continued

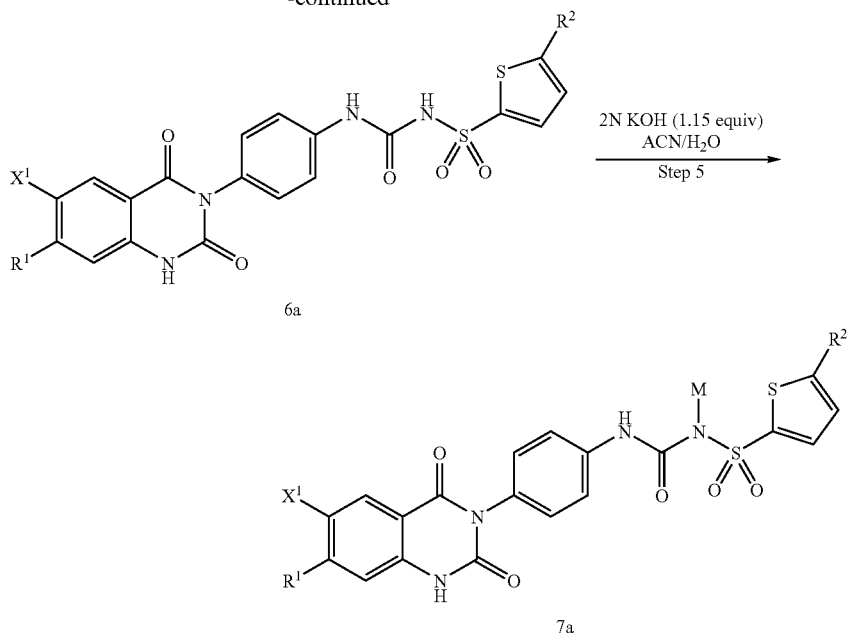

The urea 3a can be prepared by treating compound 2 with p-nitrophenylchloroformate, in an inert solvent, such as THF, dichloromethane and/or MeCN, at an appropriate temperature, typically at about 20° C., followed by treatment with an appropriately protected aniline (Method B). According to the invention, compounds of formula (I) may be further treated to form pharmaceutically acceptable salts e.g. 7a. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

Compounds of formula (I) may be isolated using typical isolation and purification techniques known in the art, including, for example, chromatographic and recrystallization methods.

In compounds of formula (I) of the invention, carbon atoms of $R^1$ to which four non-identical substituents are bonded are asymmetric. Accordingly, a compound of formula (I) may exist as enantiomers, diastereomers or a mixture thereof. The enantiomers and diastereomers may be separated by chromatographic or crystallization methods, or by other methods known in the art. The asymmetric carbon atom when present in a compound of formula (I) of the invention, may be in one of two configurations (R or S) and both are within the scope of the invention. The presence of small amounts of the opposing enantiomer or diastereomer in the final purified product does not affect the therapeutic or diagnostic application of such compounds.

According to the invention, compounds of formula (I) may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

The invention also provides pharmaceutically acceptable isomers, hydrates, and solvates of compounds of formula (I). Compounds of formula (I) may also exist in various isomeric and tautomeric forms including pharmaceutically acceptable salts, hydrates and solvates of such isomers and tautomers. For example, while some compounds are provided herein as dihydrates having two molecules of water per molecule of the compound of formula (I), the present invention also provides compounds that are anhydrous, monohydrates, trihydrates, sesquihydrates, and the like.

This invention also encompasses prodrug derivatives of the compounds of formula (I). The term "prodrug" refers to a pharmacologically inactive derivative of a parent drug molecule that requires biotransformation, either spontaneous or enzymatic, within the organism to release the active drug. Prodrugs are variations or derivatives of the compounds of formula (I) of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple, etc., depending on the number of biotransformation steps required to release the active drug within the organism, and indicating the number of functionalities present in a precursor-type form. Prodrug forms often offer advantages of solubility, tissue compatibility, or delayed release in the mammalian organism (Bundgard, *Design of Prodrugs*, pp. 7-9, 21-24, Elsevier, Amsterdam (1985); Silverman, *The Organic Chemistry of Drug Design and Drug Action*, pp. 352-401, Academic Press, San Diego, Calif. (1992)). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

IV. Crystalline solid and Amorphous Embodiments of the Invention and their Preparation The present invention also provides crystalline solid and/or amorphous forms of [4-(6-fluoro-7-methylamino-2,4-dioxo-1,4-dihydro-2H-quinazolin-3-yl)-phenyl]-5-chloro-thiophen-2-yl-sulfonylurea and processes for their preparation and pharmaceutical compositions comprising these forms. The potassium salt has the following general formula:

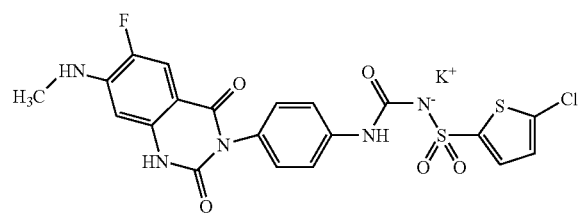

and the sodium salt has the following general formula:

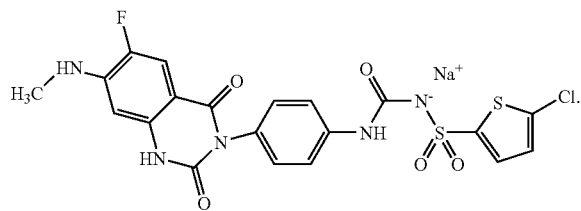

In developing a process for production of an active pharmaceutical ingredient (API), two factors are of great importance: the impurity profile and the crystal morphology of the compound. The results from the initial isolation and crystallization work showed a profile of [4-(6-fluoro-7-methylamino-2,4-dioxo-1,4-dihydro-2H-quinazolin-3-yl)-phenyl]-5-chloro-thiophen-2-yl-sulfonylurea of 99.6%. Preferably the API has levels of impurities below 0.2% and is in the most thermodynamically stable crystalline solid form. The isolation and crystallization work indicated that there was at least two crystalline solid forms of the potassium salt of [4-(6-fluoro-7-methylamino-2,4-dioxo-1,4-dihydro-2H-quinazolin-3-yl)-phenyl]-5-chloro-thiophen-2-yl-sulfonylurea (designated as Form A and B) and an amorphous form of the sodium salt of [4-(6-fluoro-7-methylamino-2,4-dioxo-1,4-dihydro-2H-quinazolin-3-yl)-phenyl]-5-chloro-thiophen-2-yl-sulfonylurea.

The solid forms of the invention may be described by one or more of several techniques including X-ray powder diffraction, Raman spectroscopy, IR spectroscopy, and thermal methods. Further, combinations of such techniques may be used to describe the invention. For example, one or more X-ray powder diffraction peaks combined with one or more Raman peaks may be used to describe one or more solid forms of the invention in a way that differentiates it from the other solid forms.

Although it characterizes a form, it is not necessary to rely only upon an entire diffraction pattern or spectrum to characterize a solid form. Those of ordinary skill in the pharmaceutical arts recognize that a subset of a diffraction pattern or spectrum may be used to characterize a solid form provided that subset distinguishes the solid form from the other forms being characterized. Thus, one or more X-ray powder diffraction peaks alone may be used to characterize a solid form. Likewise, one or more IR peaks alone or Raman peaks alone may be used to characterize a solid form. Such characterizations are done by comparing the X-ray, Raman, and IR data amongst the forms to determine characteristic peaks.

One may also combine data from other techniques in such a characterization. Thus, one may rely upon one or more peaks from an x-ray powder diffraction and for example, Raman or IR data, to characterize a form. For example, if one or more x-ray peaks characterize a form, one could also consider Raman or IR data to characterize the form. It is sometimes helpful to consider Raman data, for example, in pharmaceutical formulations.

The polymorphs were identified from by using two different crystallization conditions. (1) Crystalline form A was isolated after crystallization of the crude wet-cake from methanol and drying the crude wet-cake to effect solvent removal, and (2) crystalline solid form B was formed from crystallization from EtOH/$H_2O$ or by trituration with methanol.

The potassium salt was suspended in methanol and then heated until a clear solution was observed. This was followed by cooling and the resulting crystalline solid was isolated and dried at room temperature under reduced pressure to give the morphologically distinct crystalline solid potassium salt/form A. FIGS. 14 and 2 respectively show the DSC trace and the X-ray powder pattern for the crystalline solid. Differential scanning calorimetry (DSC) of Form A of [4-(6-fluoro-7-methylamino-2,4-dioxo-1,4-dihydro-2H-quinazolin-3-yl)-phenyl]-5-chloro-thiophen-2-yl-sulfonylurea potassium salt defined a melt of desolvate at 238° C. A large decomposition peak was recorded, onset temperature approximately 300° C. In the DSC trace, the sharpness of the completion of melt at about 246° C. is characteristic.

In the X-ray powder diffraction pattern, the peaks at about 9.5 and 25.5 are the main features of the pattern (for a discussion of the theory of X-ray powder diffraction patterns see "X-ray diffraction procedures" by H. P. Klug and L. E. Alexander, J. Wiley, New York (1974)). The peaks at about 9.5° 2θ and 25.5°2θ characterize Form A with respect to Form B because Form B does not have peaks to within 0.2°2θ, twice the approximate precision of X-ray powder diffraction peaks, of the two Form A peaks. Because the typical variation in any given x-ray powder diffraction peak is on the order of 0.20°2θ, when selecting peaks to characterize a polymorph, one selects peaks that are at least twice that value (i.e., 0.4°θ) from a peak from another polymorph. Thus, in a particular polymorph x-ray pattern, a peak that is at least 0.40°θ from a peak in another polymorph is eligible to be considered as a peak that can either alone or together with another peak be used to characterize that polymorph. Tables 1 and 2 identify the main peaks of Forms A and B. From that list, one sees that the peak at about 25.5°2θ (on the table listed as 25.478°2θ), when taken to one decimal point, is greater than 0.2°2θ away from any peak in Forms B. Thus, the peak at about 25.5°2θ can be used to distinguish Form A from Form B. The peak at about 9.5°2θ (9.522°2θ in Table 1) is the most intense peak in the Form A X-ray powder diffraction pattern of FIG. 2 and is more than 0.2°2θ away from any peak in Form B. Thus, the Form A peaks at about 9.5°2θ and 25.5°2θ characterize Form A with respect to Form B. The solid form isolated at this stage in the process contained about 2 molecule of water to one molecule of salt.

TABLE 1

Potassium Salt Form A XRPD Peak (°2θ) and % Intensity Listing Data Tabulated from FIG. 2b.

| Intensity (%) | Angle (°2-Theta) | d value (Å) |
| --- | --- | --- |
| 100.0 | 9.522 | 9.28049 |
| 35.0 | 25.478 | 3.49317 |

TABLE 1-continued

Potassium Salt Form A XRPD Peak (°2θ) and
% Intensity Listing Data Tabulated from FIG. 2b.

| Intensity (%) | Angle (°2-Theta) | d value (Å) |
|---|---|---|
| 24.2 | 28.764 | 3.10110 |
| 22.5 | 27.175 | 3.27877 |
| 20.1 | 19.090 | 4.64529 |
| 15.2 | 22.977 | 3.86744 |
| 14.4 | 24.630 | 3.61155 |
| 13.8 | 23.987 | 3.70680 |
| 12.3 | 15.530 | 5.70104 |
| 12.3 | 18.518 | 4.78751 |
| 12.1 | 18.146 | 4.88482 |
| 9.5 | 16.223 | 5.45912 |
| 8.9 | 13.219 | 6.69229 |
| 8.7 | 21.040 | 4.21883 |
| 6.8 | 16.929 | 5.23304 |
| 5.6 | 4.822 | 18.31110 |

TABLE 2

Potassium Salt Form B XRPD Peak (°2θ) and
% Intensity Listing Data Tabulated from FIG. 3b.

| Intensity (%) | Angle (°2-Theta) | d value (Å) |
|---|---|---|
| 100.0 | 25.087 | 3.54667 |
| 70.4 | 20.328 | 4.36505 |
| 63.9 | 24.442 | 3.63878 |
| 52.9 | 5.339 | 16.53922 |
| 50.9 | 19.594 | 4.52687 |
| 34.7 | 26.155 | 3.40428 |
| 30.6 | 17.37 | 5.10115 |
| 28.6 | 21.373 | 4.15387 |
| 28.1 | 14.526 | 6.09284 |
| 27.6 | 22.53 | 3.94319 |
| 26.5 | 9.921 | 8.90794 |
| 26.5 | 21.729 | 4.08664 |
| 24.9 | 13.569 | 6.52011 |
| 23.6 | 15.346 | 5.76906 |
| 22.9 | 29.478 | 3.02760 |
| 18.9 | 10.655 | 8.29583 |

Preferred orientation can affect peak intensities, but not peak positions, in XRPD patterns. In the case of the potassium salts, preferred orientation has the most effect on the region at lower angles. Preferred orientation causes some peaks in this region to be diminished (or increased). Crystal habit does not clearly differentiate between the solid forms; a variety of habits have been observed for each form, including needles, blades, plates, and irregular-shaped particles.

Thus in one embodiment, the present invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in new crystalline forms designated as Form A and Form B.

Thus in one embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, which provides at least one of:
(i) an infra red spectrum substantially in accordance with FIG. 5;
(ii) an X-ray powder diffraction pattern substantially in accordance with FIG. 2; and
(iii) a DSC scan substantially in accordance with FIG. 14; herein designated as Form A.

In another embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, which provides at least one of:
(i) an infra red spectrum comprising absorption peaks at about 3559, 3389, 3324, 1698, 1623, 1563, 1510, 1448, 1431, 1403, 1383, 1308, 1269, 1206, 1174, 1123, 1091, 1072, 1030, 987, 939, 909, 871, 842, 787, 780, 769, 747, 718, 701, 690 and 667 cm$^{-1}$;
(ii) an X-ray powder diffraction pattern comprising peaks at about 9.5 and about 25.5°2θ; and
(iii) a DSC maximum endotherm at about 246° C.;
herein designated as Form A.

In another embodiment, the invention provides a crystalline polymorph of [4-(6-fluoro-7-methylamino-2,4-dioxo-1,4-dihydro-2H-quinazolin-3-yl)-phenyl]-5-chloro-thiophen-2-yl-sulfonylurea potassium salt which provides an infra red spectrum containing absorption peaks at about 3559, 3389, 3324, 1698, 1623, 1563, 1510, 1448, 1431, 1403, 1383, 1308, 1269, 1206, 1174, 1123, 1091, 1072, 1030, 987, 939, 909, 871, 842, 787, 780, 769, 747, 718, 701, 690 and 667 cm$^{-1}$;
herein designated as Form A.

In another embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, which provides an X-ray powder diffraction pattern comprising peaks at about 9.5 and about 25.5°2θ herein designated as Form A.

In another embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, which provides a DSC endotherm maximum of about 246° C.;
herein designated as Form A.

In another embodiment, the invention provides a crystalline polymorph of [4-(6-fluoro-7-methylamino-2,4-dioxo-1,4-dihydro-2H-quinazolin-3-yl)-phenyl]-5-chloro-thiophen-2-yl-sulfonylurea potassium salt which provides spectrum containing at least one, but fewer than the above peak listings, herein designated as Form A.

FIGS. 16 and 3 respectively show the DSC trace and the X-ray powder pattern for another crystalline solid. These results were observed when the remaining water was removed. In the DSC trace, a transition at about 293° C. is noteworthy, because Form A melts at 246° C. The peaks at about 20.3°2θ and 25.1°2θ in the X-ray powder diffraction pattern also characterize Form B with respect to Form A, because Form A does not have peaks to within 0.2°2θ, the approximate precision of X-ray powder diffraction peaks, of the two characteristic Form B peaks (see Tables 1 and 2). From that list, one sees that the peaks at about 20.3°2θ and 25.1°2θ (in Table 2 listed as 20.328°2θ and 25.087°2θ, respectively), when taken to one decimal point, is greater than 0.2°2θ away from any peak in Form A. Thus, the peaks at about 20.3°2θ and 25.1°2θ can be used to distinguish Form B from Form A.

Thus in one embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, which provides at least one of:
(i) an infra red spectrum substantially in accordance with FIG. 6;
(ii) an X-ray powder diffraction pattern substantially in accordance with FIG. 3; and
(iii) a DSC scan substantially in accordance with FIG. 16; herein designated as Form B.

In another embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, which (i) an infra red spectrum comprising absorption peaks at about 3584, 3327, 3189, 2935, 2257, 2067, 1979, 1903, 1703, 1654, 1630, 1590, 1557, 1512, 1444, 1429, 1406, 1375, 1317, 1346, 1317, 1288, 1276, 1243, 1217, 1182, 1133, 1182, 1133, 1093, 1072, 1033, 987, 943, 907, 883, 845, 831, 805, 776, 727, 694 and 674 cm$^{-1}$; (ii) an X-ray powder diffraction pattern comprising peaks at about 20.3°2θ and about 25.1°2θ; and (iii) a DSC maximum endotherm at about 293° C.; herein designated as Form B.

In another embodiment, the invention provides [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form, including a substantially pure form, wherein the compound provides an X-ray powder diffraction pattern comprising peaks at about 20.3°2θ and 25.1°2θ; herein designated as Form B.

In another embodiment the present invention provides [4-(6-fluoro-7-methylamino-2,4-dioxo-1,4-dihydro-2H-quinazolin-3-yl)-phenyl]-5-chloro-thiophen-2-yl-sulfonylurea sodium salt in an amorphous form.

In one embodiment, the invention provides a form of [4-(6-fluoro-7-methylamino-2,4-dioxo-1,4-dihydro-2H-quinazolin-3-yl)-phenyl]-5-chloro-thiophen-2-yl-sulfonylurea sodium salt which provides at least one of:
(i) an infra red spectrum in a mineral oil dispersion substantially in accordance with FIG. 7;
(ii) an X-ray powder diffraction pattern substantially in accordance with FIG. 4; and
(iii) a DSC scan substantially in accordance with FIG. 18; herein designated as amorphous form.

In another embodiment, the invention provides a form of [4-(6-fluoro-7-methylamino-2,4-dioxo-1,4-dihydro-2H-quinazolin-3-yl)-phenyl]-5-chloro-thiophen-2-yl-sulfonylurea sodium salt which provides an infra red spectrum containing absorption peaks at about 3560, 1711, 1632, 1556, 1512, 1445, 1407, 1375, 1309, 1280, 1227, 1133, 1092, 1032, 987, 905, 781, 770 and 691 cm$^{-1}$; herein designated as amorphous form.

In another embodiment, the invention provides a crystalline polymorph of [4-(6-fluoro-7-methylamino-2,4-dioxo-1,4-dihydro-2H-quinazolin-3-yl)-phenyl]-5-chloro-thiophen-2-yl-sulfonylurea salts which provides spectrum containing at least one, but fewer than the above peak listings for the designated forms.

Crystalline form A of [4-(6-fluoro-7-methylamino-2,4-dioxo-1,4-dihydro-2H-quinazolin-3-yl)-phenyl]-5-chloro-thiophen-2-yl-sulfonylurea potassium salt is a dihydrate which is stable to 15% relative humidity (RH) at 25° C. but which rehydrates at 20% RH at 25° C. Polymorph A of the potassium salt has been found to be equally stable as the amorphous form of the sodium salt. No change in the chemical purity of either salt form was observed after one week when in accelerated stability tests at high temperature (40° C.) and high relative humidity (75% RH). An advantage of the potassium crystalline form A is that it is less hygroscopic than the amorphous form of the sodium salt which picks up >15% w/w water at 40% RH. Both Form A and B are stable. Form B of the potassium salt is anhydrous and non-hygroscopic (difficult to form a dehydrate form) Form B of the potassium salt retains a better physical appearance and handling properties over a longer period of time. An improvement in the physical appearance of a dosage form of a drug enhances both physician and patient acceptance and increases the likelihood of success of the treatment.

Further embodiments of the invention include mixtures of the different crystalline solid forms, and the amorphous form, of [4-(6-fluoro-7-methylamino-2,4-dioxo-1,4-dihydro-2H-quinazolin-3-yl)-phenyl]-5-chloro-thiophen-2-yl-sulfonylurea and its salts. Such mixtures include compositions comprising at least one solid form or at least two solid forms selected from Form A, Form B and the amorphous form. Any of the analytical techniques described herein may be used to detect the presence of the solid forms in such compositions. Detection may be done qualitatitvely, quantitatively, or semi-quantitatively as those terms as used and understood by those of skill in the solid-state analytical arts.

For these analyses, use of standard analytical techniques involving reference standards may be used. Further, such methods may include use of techniques such as partial-lease squares in conjunction with a diffractive or spectroscopic analytical technique. These techniques may also be used in pharmaceutical compositions of the invention.

V. Preparation of Crystalline Solid and Amorphous Forms of the Invention

Furthermore, the present invention is directed to processes for the preparation of crystalline solid and amorphous forms of [4-(6-fluoro-7-methylamino-2,4-dioxo-1,4-dihydro-2H-quinazolin-3-yl)-phenyl]-5-chloro-thiophen-2-yl-sulfonylurea potassium and sodium salts.

Crystalline solid and amorphous forms of the compounds of the invention may be prepared by various methods as outlined below. Other well-known crystallization procedures as well as modification of the procedures outline above may be utilized.

In another embodiment of the present invention there is provided [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form A, which is obtained by at least one of:
(i) crystallizing [4-(6-fluoro-7-methylamino-2,4-dioxo-1,4-dihydro-2H-quinazolin-3-yl)-phenyl]-5-chloro-thiophen-2-yl-sulfonylurea potassium salt from at least one solvent selected from the group consisting of ethanol, methanol, and combinations thereof and drying such that the crystal contained some solvent; and
(ii) heating [4-(6-fluoro-7-methylamino-2,4-dioxo-1,4-dihydro-2H-quinazolin-3-yl)-phenyl]-5-chloro-thiophen-2-yl-sulfonylurea potassium salt in at least one solvent selected from the group consisting of ethanol, methanol, and combinations thereof; crystallizing at a temperature of from about 50° C. to −10° C. and drying until the crystals contained at least about 0.05% solvent.

In another embodiment of the present invention there is provided [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form B, which is obtained by at least one of:
(i) heating [4-(6-fluoro-7-methylamino-2,4-dioxo-1,4-dihydro-2H-quinazolin-3-yl)-phenyl]-5-chloro-thiophen-2-yl-sulfonylurea potassium salt in a solvent combination of ethanol and water; crystallizing at a temperature of from about 50° C. to −10° C. and drying until the crystals contain less than 0.05% solvent; and
(ii) crystallizing [4-(6-fluoro-7-methylamino-2,4-dioxo-1,4-dihydro-2H-quinazolin-3-yl)-phenyl]-5-chloro-thiophen-2-yl-sulfonylurea potassium salt from a solvent combination of ethanol and water and drying such that the crystal contained less than 0.05% solvent.

In another embodiment of the present invention there is provided a amorphous crystalline form of [4-(6-fluoro-7-methylamino-2,4-dioxo-1,4-dihydro-2H-quinazolin-3-yl)-phenyl]-5-chloro-thiophen-2-yl-sulfonylurea potassium salt by triturating in isopropanol and drying.

In another embodiment of the present invention there is provided a amorphous crystalline form of [4-(6-fluoro-7-methylamino-2,4-dioxo-1,4-dihydro-2H-quinazolin-3-yl)-phenyl]-5-chloro-thiophen-2-yl-sulfonylurea sodium salt which is obtained by at least one of:
(i) heating [4-(6-fluoro-7-methylamino-2,4-dioxo-1,4-dihydro-2H-quinazolin-3-yl)-phenyl]-5-chloro-thiophen-2-yl-sulfonylurea sodium salt in at least one solvent selected from the group consisting of isopropanol, acetonitrile, ethanol and combinations thereof; and crystallizing at a temperature of from about 50° C. to −10° C.;
(ii) crystallizing [4-(6-fluoro-7-methylamino-2,4-dioxo-1,4-dihydro-2H-quinazolin-3-yl)-phenyl]-5-chloro-thiophen-2-yl-sulfonylurea sodium salt from at least one solvent selected from the group consisting of isopropanol, acetonitrile, ethanol and combinations thereof; and
(iii) heating [4-(6-fluoro-7-methylamino-2,4-dioxo-1,4-dihydro-2H-quinazolin-3-yl)-phenyl]-5-chloro-thiophen-2-yl-sulfonylurea sodium salt in high humidity.

Furthermore, the present invention is directed to the above described processes for the preparation of crystalline solid and amorphous forms of [4-(6-fluoro-7-methylamino-2,4-dioxo-1,4-dihydro-2H-quinazolin-3-yl)-phenyl]-5-chloro-thiophen-2-yl-sulfonylurea potassium and sodium salts.

[4-(6-fluoro-7-methylamino-2,4-dioxo-1,4-dihydro-2H-quinazolin-3-yl)-phenyl]-5-chloro-thiophen-2-yl-sulfonylurea in a crystalline solid or amorphous form may be prepared by various methods as further described below in the Examples. The examples illustrate, but do not limit the scope of the present invention. [4-(6-fluoro-7-methylamino-2,4-dioxo-1,4-dihydro-2H-quinazolin-3-yl)-phenyl]-5-chloro-thiophen-2-yl-sulfonylurea in crystalline solid or amorphous forms may be isolated using typical isolation and purification techniques known in the art, including, for example, chromatographic, recrystallization and other crystallization procedures as well as modification of the procedures outlined above.

VI. Pharmaceutical Compositions

A compound of formula (I) according to the invention may be formulated into pharmaceutical compositions. Accordingly, the invention also provides a pharmaceutical composition for preventing or treating thrombosis in a mammal, particularly those pathological conditions involving platelet aggregation, containing a therapeutically effective amount of a compound of formula (I) or a pharmaceutically acceptable salt thereof, each as described above, and a pharmaceutically acceptable carrier or agent. Preferably, a pharmaceutical composition of the invention contains a compound of formula (I), or a salt thereof, in an amount effective to inhibit platelet aggregation, more preferably, ADP-dependent aggregation, in a mammal, in particular, a human. Pharmaceutically acceptable carriers or agents include those known in the art and are described below.

Pharmaceutical compositions of the invention may be prepared by mixing the compound of formula (I) with a physiologically acceptable carrier or agent. Pharmaceutical compositions of the invention may further include excipients, stabilizers, diluents and the like and may be provided in sustained release or timed release formulations. Acceptable carriers, agents, excipients, stablilizers, diluents and the like for therapeutic use are well known in the pharmaceutical field, and are described, for example, in *Remington's Pharmaceutical Sciences*, Mack Publishing Co., ed. A. R. Gennaro (1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Further embodiments of the invention include pharmaceutical compositions of [4-(6-fluoro-7-methylamino-2,4-dioxo-1,4-dihydro-2H-quinazolin-3-yl)-phenyl]-5-chloro-thiophen-2-yl-sulfonylurea, its salts and forms, including in therapeutically effective amounts of Form A, Form B, and the amorphous form. Said amounts of the at least one of said forms may or may not be in therapeutically effective amounts. Such pharmaceutical compositions may be in the form of a solid oral composition such as a tablet or a capsule or as a dry powder for inhalation.

VII. Methods of Treatment/Administration

A. Preventing and Treating Disease Conditions Characterized by Undesired Thrombosis Methods for preventing or treating thrombosis in a mammal embraced by the invention administering a therapeutically effective amount of a compound of formula (I) alone or as part of a pharmaceutical composition of the invention as described above to a mammal, in particular, a human. Compounds of formula (I) and pharmaceutical compositions of the invention containing a compound of formula (I) of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and prostheses, and hypercoagulable states related to genetic predisposition or cancers. In other groups of embodiments, the indication is selected from the group consisting of percutaneous coronary intervention (PCI) including angioplasty and/or stent, acute myocardial infarction (AMI), unstable angina (USA), coronary artery disease (CAD), transient ischemic attacks (TIA), stroke, peripheral vascular disease (PVD), Surgeries-coronary bypass, carotid endarterectomy Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin or anti-inflammatories (non-steriodal anti-inflammatories, cyclooxygenase II inhibitors). Coadministration may also allow for application of reduced doses of both the anti-platelet and the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Compounds and pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles. Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formula (I) employed, the specific use for which the compound or pharmaceutical composition is employed, and other factors which those skilled in the medical arts will recognize.

B. Therapeutically Effective Amount

Dosage formulations of compounds of formula (I), or pharmaceutical compositions contain a compound of the invention, to be used for therapeutic administration must be sterile. Sterility is readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formula (I) or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formula (I) and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

Therapeutically effective dosages may be determined by either in vitro or in vivo methods. For each particular compound or pharmaceutical composition of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formula (I) is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

C. Administration

Therapeutic compound liquid formulations generally are placed into a container having a sterile access port, for example, an intravenous solution bag or vial having a stopper pierceable by hypodermic injection needle.

Typical adjuvants which may be incorporated into tablets, capsules, lozenges and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

D. Combination Therapies

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The following preparations and examples are given to enable those skilled in the art to more clearly understand and to practice the present invention. They should not be considered as limiting the scope of the invention, but merely as being illustrative and representative thereof.

VIII. EXAMPLES

General Methods

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates were characterized by high performance liquid chromatography (HPLC) using a Waters Alliance chromatography system with a 2695 Separation Module (Milford, Mass.). The analytical columns were C-18 SpeedROD RP-18E Columns from Merck KGaA (Darmstadt, Germany). Alternately, characterization was performed using a Waters Unity (UPLC) system with Waters Acquity UPLC BEH C-18 2.1 mm×15 mm columns. A gradient elution was used, typically starting with 5% acetonitrile/95% water and progressing to 95% acetonitrile over a period of 5 minutes for the Alliance system and 1 minute for the Acquity system. All solvents contained 0.1% trifluoroacetic acid (TFA). Compounds were detected by ultraviolet light (UV) absorption at either 220 or 254 nm. HPLC solvents were from EMD Chemicals, Inc. (Gibbstown, N.J.). In some instances, purity was assessed by thin layer chromatography (TLC) using glass backed silica gel plates, such as, for example, EMD Silica Gel 60 2.5 cm×7.5 cm plates. TLC results were readily detected visually under ultraviolet light, or by employing well known iodine vapor and other various staining techniques.

Mass spectrometric analysis was performed on one of two Agilent 1100 series LCMS instruments with acetonitrile/water as the mobile phase. One system using TFA as the modifier and measures in positive ion mode [reported as MH+, (M+1) or (M+H)+] and the other uses either formic acid or ammonium acetate and measures in both positive [reported as MH$^+$, (M+1) or (M+H)$^+$] and negative [reported as M−, (M−1) or (M−H)$^−$] ion modes.

Nuclear magnetic resonance (NMR) analysis was performed on some of the compounds with a Varian 400 MHz NMR (Palo Alto, Calif.). The spectral reference was either TMS or the known chemical shift of the solvent.

The purity of some of the invention compounds is assessed by elemental analysis (Robertson Microlit, Madison N.J.).

Melting points are determined on a Laboratory Devices Mel-Temp apparatus (Holliston, Mass.).

Preparative separations were carried out using either an Sq16x or an Sg100c chromatography system and prepackaged silica gel columns all purchased from Teledyne Isco, (Lincoln, Nebr.). Alternately, compounds and intermediates were purified by flash column chromatography using silica gel (230-400 mesh) packing material, or by HPLC using a C-18 reversed phase column. Typical solvents employed for the Isco systems and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Instrumental for Solid Forms

1. FT Infrared Spectroscopy (FTIR)

Samples were studied on a Perkin-Elmer Spectrum One fitted with a Universal ATR sampling accessory and running Spectrum V5.0.1 software. The resolution was set to 4 cm−1 and 16 scans were collected over the range 4000 cm$^{-1}$ to 400 cm$^{-1}$. Control and Analysis software: Spectrum v 5.0.1.

2. Differential Scanning Calorimetry (DSC)

DSC data (thermograms) were collected on a TA instruments Q1000 equipped with a 50 position auto-sampler. The energy and temperature calibration standard was indium. Samples were heated at a rate of 10° C./min from 10° C. to 250° C. A nitrogen purge at 30 ml/min was maintained over the sample.

Between 1 and 3 mg of sample was used, unless otherwise stated, and all samples were sealed in an aluminum pan with a pinhole in the lid. Control software: Advantage for Q series v 2.2.0.248, Thermal Advantage Release 4.2.1. Analysis software: Universal Analysis 2000 v 4.1D Build 4.1.0.16

3. Thermogravimetric Analysis (TGA)

TGA data (thermograms) were collected on a TA Instrument Q500 TGA with a 16 position auto-sampler. Samples were heated at a rate of 10° C./minute. A nitrogen purge of 100 ml/min was maintained over the sample.

Typically 5-20 mg of sample was loaded onto a tared open aluminum open pan. Control software: Advantage for Q series v 2.2.0.248, Thermal Advantage Release 4.2.1. Analysis software: Universal Analysis 2000 v 4.1D Build 4.1.0.16

4. XRPD (X-Ray Powder Diffraction)
Bruker AXS C2 GADDS Diffractometer

X-ray powder diffraction patterns for the samples were acquired on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm.

Beam divergence, i.e. the effective size of the X-ray beam on the sample, was approximately 4 mm. A θ-θ continuous scan mode was employed with a sample to detector distance of 20 cm which gives an effective 2θ range of 3.2°-29.8°. A typical exposure time of a sample was 120 s.

Samples run under ambient conditions were prepared as flat plate specimens using powder as received without grinding. Approximately 1-2 mg of the sample was lightly pressed on a glass slide to obtain a flat surface. Control software: GADDS for WNT v 4.1.16. Analysis software: Diffrac Plus Release 3 EVA v 9.0.0.2

5. Gravimetric Vapor Sorption (GVS) Studies

Isotherms were collected on a Hiden IGASorp moisture sorption analyzer running CFRSorp software. Sample sizes were typically ca. 10 mg. A moisture adsorption/desorption isotherm was performed as outlined below. The samples were loaded and unloaded at room humidity and temperature (ca. 40% RH, 25° C.). The standard isotherm run was a single cycle starting at 40% RH. The humidity was stepped as follows: 40, 50, 60, 70, 80, 90, 85, 75, 65, 55, 45, 35, 25, 15, 5, 0, 10, 20, 30, 40. Control and Analysis software: IGASorp Controller v 1.10, IGASorp Systems Software v 3.00.23.

6. $^1$H NMR

Spectra were collected on a Bruker 400 MHz equipped with auto sampler. Samples were prepared in $d_6$-DMSO.

7. Purity Analysis

Purity analysis was performed on an Agilent HP1100 system equipped with a diode array detector.
Method: Gradient
Column details: Betabasic C18, 5 μm, 150×4.6 mm
Column Temperature: 25° C.
Injection volume: 5 μl
Flow Rate ml/min: 0.8 ml/min
Detection wavelength: 325 nm
Phase A: 0.1% v/v aqueous formic acid
Phase B: Acetonitrile: water 90:10 with 0.1% v/v formic acid

TABLE 3

Mobile phase timetable.

| Time/Min | % A | % B |
|---|---|---|
| 0 | 90 | 10 |
| 2 | 90 | 10 |
| 17 | 10 | 90 |
| 21 | 10 | 90 |
| 21.3 | 90 | 10 |
| 25 | 90 | 10 |

TABLE 4

|  | potassium salt | sodium salt |
|---|---|---|
| Purity | 99.4% (a/a) | 99.4% (a/a) |
| Impurities |  |  |
| Individual peaks ≧ 0.1% (a/a) | % (a/a) | % (a/a) |
| RRT = 0.57 | 0.14 | 0.11 |
| RRT = 1.08 | 0.15 | 0.18 |
| Total of peaks < 0.1% (a/a) | 0.3 | 0.3 |

Example 1

Synthesis of the Intermediate Sulfonylurea Carbamate (8)

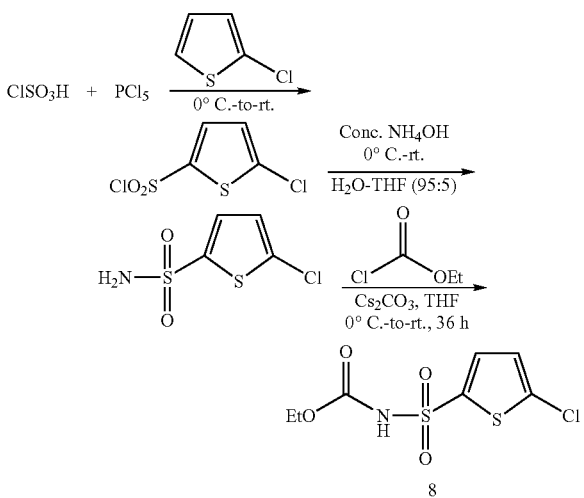

Step 1—Preparation 5-chlorothiophene-2-sulfonyl chloride

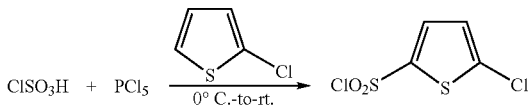

The following procedure was adapted from C. A. Hunt, et al. *J. Med. Chem.* 1994, 37, 240-247. In a three-necked R. B. flask, equipped with a mechanical stirrer, an air condenser, a dropping funnel, and a moisture-guard tube, was placed chlorosulfonic acid (240 mL, 3.594 mol). Under stirring, PCl$_5$ (300 g, 1.44 mol, 0.40 equiv) was added in portions, over ca. 45 mins. During the addition, a large volume of HCl gas evolved vigorously, but the temperature of the mixture did not rise significantly (<40° C.). By the time all the PCl$_5$ had been added, an almost clear, pale yellow solution resulted, with only a few solid pieces of PCl$_5$ floating in the suspension. It was stirred until gas evolution ceased (0.5 h).

Then the reaction vessel was cooled in ice, and 2-chlorothiophene (66.0 mL, 0.715 mol) was added via the dropping funnel, over 1.0 h. With the addition of the very first few drops of 2-Cl-thiophene, the mixture turned dark purple, and by the time all of the thiophene had been added, a dark purple solution resulted. During the addition, HCl gas evolved continuously, at a slow rate. The reaction mixture was then stirred at room temperature overnight.

Then the mixture, dark-purple clear solution, was added dropwise to crushed ice (3 L), over 0.5 h. On addition to ice, the purple color disappeared instantaneously; the colorless thin emulsion was stirred mechanically at room temperature for ca. 15 h. Then the mixture was extracted with CH$_2$Cl$_2$ (3×300 mL). The combined CH$_2$Cl$_2$-extract was washed with water (1×200 mL), saturated NaHCO$_3$ (1×250 mL), brine (1×100 mL), dried (Na$_2$SO$_4$), and concentrated on a rotary evaporator to yield the crude product as a pale yellow glue, which showed a tendency to solidify, yielding a semi-solid mass. This was then purified by high-vacuum distillation (bp 110-112°/12 mm) to yield 135.20 g (88%) of the title compound as a colorless/pale-yellow semi solid.

Step 2—5-chlorothiophene-2-sulfonamide

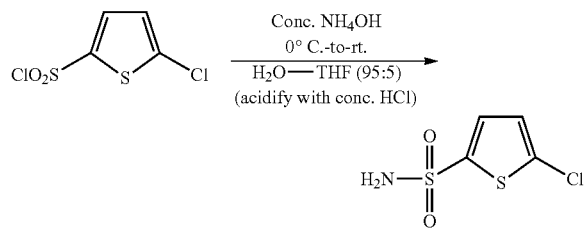

The following procedure was adapted from C. A. Hunt, et al. *J. Med. Chem.* 1994, 37, 240-247. In a three-necked R. B. flask, equipped with a mechanical stirrer, conc. NH$_4$OH (500 mL, 148.50 g NH$_3$, 8.735 mol NH$_3$, 13.07 equiv NH$_3$) was placed. The flask was cooled in ice and 5-chlorothiophene-2-sulfonyl chloride (145.0 g, 0.668 mol) was added, in portions over 0.5 h (it is a low-melting solid, and it was melted by warming, which was then conveniently added via a wide-bored polyethylene pipette). The sulfonyl chloride immediately solidifies in the reaction flask. After all the sulfonyl chloride had been added, the flask containing it was rinsed with THF (25 mL), and this also was transferred to the reaction vessel. Then the heavy suspension was stirred at room temperature for ca. 20 h. At the end of this time the reaction mixture was still a suspension but of a different texture.

Then the mixture was cooled in ice, diluted with H$_2$O (1.5 l), and acidified with conc. HCl to pH ca. 3. The solid product was collected by filtration using a Buchner funnel, rinsed with cold water, and air-dried to afford the title compound as a colorless solid, 103.0 g (78%). MS (M−H): 196.0; 198.0

Step 3—Ethyl 5-chlorothiophen-2-ylsulfonylcarbamate

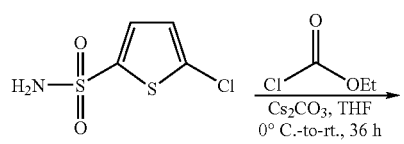

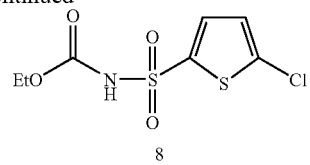

A 2-L 3-necked R. B. flask, equipped with a mechanical stirrer and a dropping funnel, was charged with sulfonamide (60.0 g, 303.79 mmol), and Cs$_2$CO$_3$ (200 g, 613.83 mmol, 2.02 equiv) in THF (900 mL). The clear solution was cooled in ice, and ethyl chloroformate (70.0 mL, 734.70 mmol, 2.418 equiv) was added over ca. 30 mins. The heavy suspension was then stirred at room temperature for ca. 36 h.

Then the mixture was diluted with water (200 mL) to yield a clear colorless solution, which was concentrated on rotary evaporator to one-third its volume. This was then diluted with EtOAc (250 mL), cooled in ice, and acidified with 6N HCl to pH ca. 1. The biphasic mixture was transferred to a separatory funnel, layers were separated, and the aqueous layer was again extracted with 2×75 µL EtOAc. The combined organic extract was washed with water/brine (2×50 mL), brine (1×50 mL), dried over Na$_2$SO$_4$, and concentrated to yield the title compound as lightly colored oil. This was purified by filtration through a silica-gel plug. The crude product was applied to the silica-gel plug on a sintered funnel in EtOAc, and then was eluted with EtOAc (1 liter). Concentration of the EtOAc filtrate provided the title compound 8 as a colorless solid, 71.28 g (87%). MS (M−H): 268.0; 270.0. $^1$H NMR (DMSO): δ 7.62 (d, 1H), 7.25 (d, 1H), 4.10 (q, 2H), 1.16 (t, 3H).

Example 2

Synthesis of [4-(6-fluoro-7-methylamino-2,4-dioxo-1,4-dihydro-2H-quinazolin-3-yl)-phenyl]-5-chloro-thiophen-2-yl-sulfonylurea (7a)

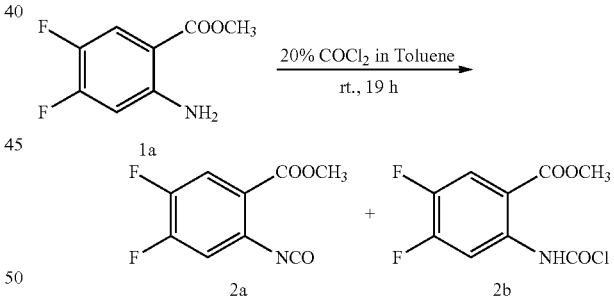

Step 1

Aniline 1 ($^1$H NMR (DMSO): δ 7.58 (dd, 1H), 6.72 (dd, 1H), 3.77 (s, 3H); 6.0 g, 32.085 mmol) was placed in a 500 mL round bottomed flask and 20% phosgene in toluene (175 mL, 332.50 mmol, 10.36 equiv) was added. The resulting somewhat sticky suspension was then magnetically stirred overnight at room temperature resulting in a clear, colorless solution. An aliquot removed, blown dry with argon, quenched with MeOH, and analyzed by RP-HPLC/MS to show no unreacted aniline 1 and clean formation of the isocyanate 2a and/or carbamoyl chloride 2b as analyzed as its methyl-carbamate. The mixture was concentrated first by rotary evaporation and then under high vacuum to yield 6.76 g (99% yield) of the isocyanate 2a and/or carbamoyl chloride 2b as a free-flowing colorless solid.

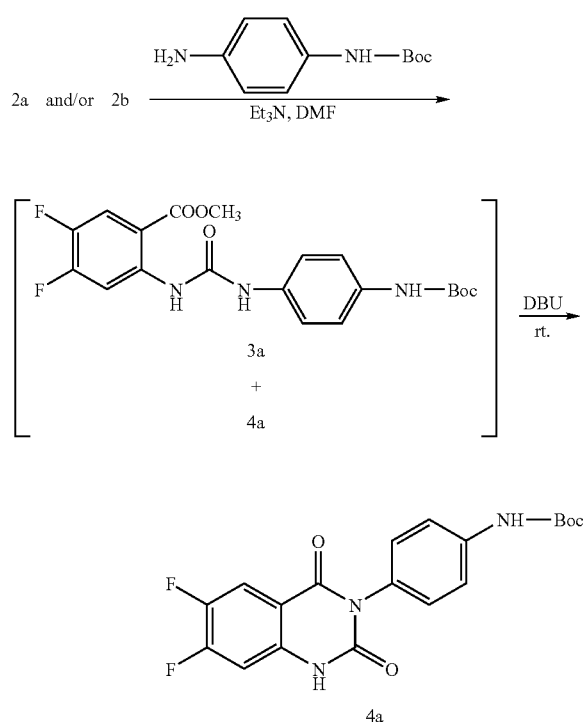

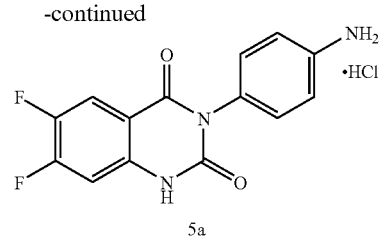

Step 3

The N-Boc-aniline 4a (4.0 g, 10.28 mmol) was placed in a round-bottomed. flask and 4N HCl in dioxane (50.0 mL, 200 mmol, 19.40 equiv) was added. The heavy, negligibly solvated suspension was stirred at room temperature for 5.0 h. HPLC showed no starting material and clean formation of the aniline 5a. The mixture was then concentrated on a rotary evaporator to yield the crude product. The solid thus obtained was triturated with $CH_2Cl_2$ to yield 3.22 g of pure 5a as an almost colorless solid (96% yield). MS (M–H): 290.3. $^1H$ NMR (DMSO): δ 11.75 (s, 1H), 7.88 (dd, 1H), 7.32 (m, 4H), 7.21 (dd, 1H).

Step 4

Step 2

In a 500 mL R. B. flask was placed N-Boc-1,4-phenylenediamine (6.22 g, 29.866 mmol, 1.20 equiv) in DMF (100 mL). Triethylamine (5.30 mL, 38.025 mmol, 1.52 equiv) was syringed in. Then the clear, dark-brown solution was treated with a solution of the isocyanate 2a (5.30 g, 24.88 mmol) and/or carbamoyl chloride 2b in DMF (50 mL), dropwise, over 15 minutes. After the addition was over, a slightly turbid mixture resulted, which was stirred overnight at room-temperature. An aliquot was analyzed, after quenching with MeOH, to show no unreacted isocyanate, and clean formation of the urea, 3a, and quinazoline-1,3-dione, 4a, in a ratio of ca. 2.5:1. MS (M–H): 388.0.

DBU (3.75 mL, 25.07 mmol, ca. 1.0 equiv) was then syringed in, dropwise, over 5 minutes, resulting in a clear dark-brown solution. This was stirred at room temperature for 3.0 h resulting in a turbid mixture. HPLC analysis showed no urea 3a and clean formation of the quinazoline-1,3-dione 4a. The reaction mixture was concentrated on a rotary evaporator to yield the crude product as a solid. This was dried under high vacuum, and then triturated with $CH_2Cl_2/H_2O$ (5:1) to yield 8.40 g of 4a as an almost colorless solid (87% yield). $^1H$ NMR (DMSO): δ 9.39 (s, 1H), 7.68 (dd, 1H), 7.45 (d, 2H), 7.03 (m, 2H), 6.98 (dd, 1H), 1.48 (s, 9H).

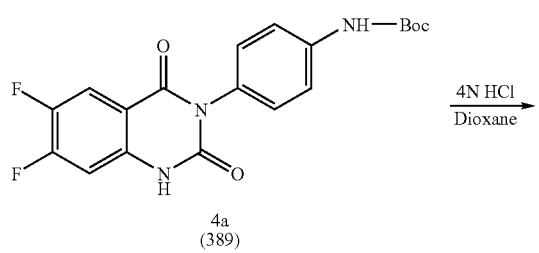

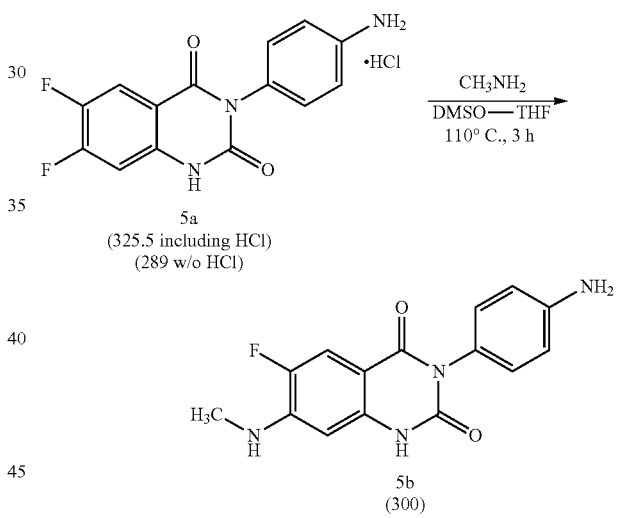

The difluoro-compound, 5a (1.0 g, 3.072 mmol) was placed in a screw-cap sealed tube. DMSO (20 mL) was added, followed by methylamine (2.0M in THF) (15.0 mL, 30 mmol, 9.76 equiv), resulting in a clear solution. This was then heated in an oil bath to 110° C. for 3 h. HPLC showed no unreacted 5a and clean formation of 5b. The mixture was then cooled to room temperature, all the $MeNH_2$ and THF were evaporated, and the residue was diluted with 100 mL water to precipitate 5b. After stirring for ca. 2 h at room temperature, the colorless solid was collected by filtration through a Buchner funnel and rinsed with $H_2O$ (100 mL), and air-dried. HPLC analysis of this solid showed it to be pure and devoid of any DBU. This solid was further purified by triturating with $Et_2O$, and then $CH_2Cl_2$ as in the previous route to this aniline to give 875 mg of the title compound (95% yield). MS (M+1) 301.2. $^1H$ NMR (DMSO): δ 11.10 (s, 1H), 7.36 (d, 1H), 6.78 (d, 2H), 6.75 (m, 1H), 6.56 (d, 2H), 6.20 (d, 1H), 5.18 (d, 2H), 2.76 (d, 3H).

Step 5—Synthesis of 1-(5-chlorothiophen-2-ylsulfonyl)-3-(4-(6-fluoro-7-(methylamino)-2,4-dioxo-1,2-dihydroquinazolin-3(4H)-yl)phenyl) urea (7a)

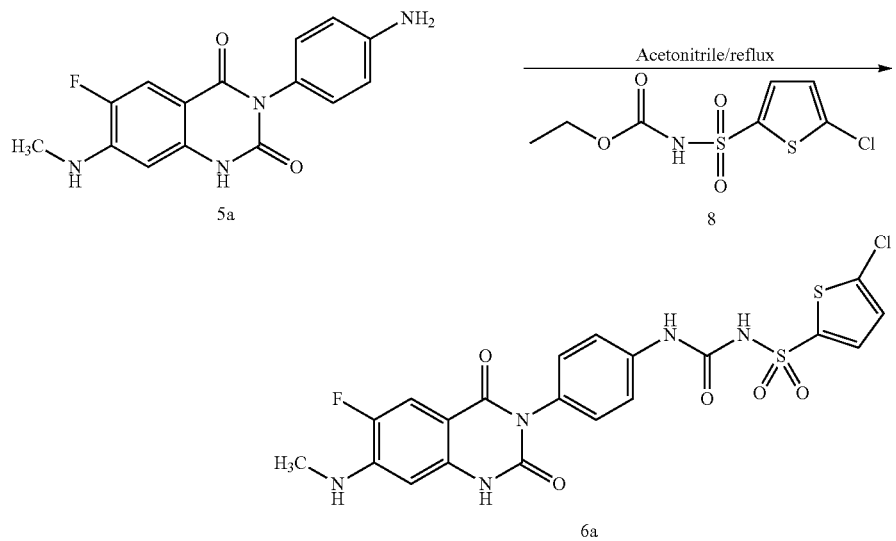

The reaction mixture comprising of the aniline (16.0 g, 53.33 mmol) and ethyl-sulfonyl-carbamate (28.77 g, 106.66 mmol, 2.0 equiv) in $CH_3CN$ (1300 mL) was heated to reflux for 36 h. During this time, the reaction mixture remained as a heavy suspension. HPLC analysis showed a clean reaction, and <1% unreacted anilne. The heavy suspension was cooled to room temperature and filtered through a Buchner funnel. The colorless solid product was further rinsed with $CH_3CN$ (3×40 mL). HPLC of the filtrate showed the presence of only a trace amount of the desired product, most of it being the excess carbamate. The crude product was then triturated with $CH_2Cl_2$ (400 mL), and the almost colorless solid product was collected by filtration through a Buchner funnel: Yield, 25.69 g (92%). MS (M+1): 524.0; 526.0. $^1$H NMR (DMSO):

δ 11.20 (s, 1H), 9.15 (s, 1H), 7.68 (d, 1H), 7.42 (d, 2H), 7.36 (d, 1H), 7.26 (m, 1H), 7.16 (d, 2H), 6.78 (m, 1H), 6.24 (d, 1H), 2.78 (d, 3H).

Example 3

[4-(6-chloro-7-methylamino-2,4-dioxo-1,4-dihydro-2H-quinazolin-3-yl)-phenyl]-5-chloro-thiophen-2-yl-sulfonylurea (6b)

The compound in Example 3 is synthesized as described for Example 2 (Step 1-5) except starting with methyl-2-amino-5-chloro-4-fluorobenzoate which was synthesized by reduction of methyl-2-nitro-5-chloro-4-fluorobenzoate with Pt(S)C.

Example 4

Synthesis of [4-(6-fluoro-7-methylamino-2,4-dioxo-1,4-dihydro-2H-quinazolin-3-yl)-phenyl]-5-chloro-thiophen-2-yl-sulfonylurea (6a) and salt (7a)

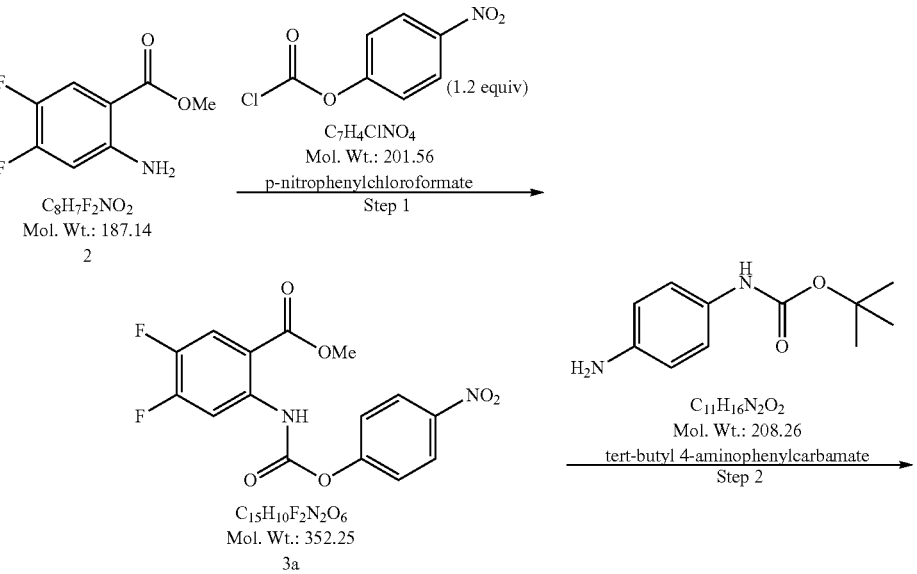

-continued
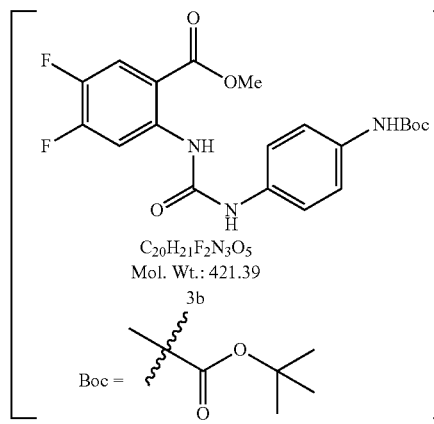
C20H21F2N3O5
Mol. Wt.: 421.39
3b
Boc =
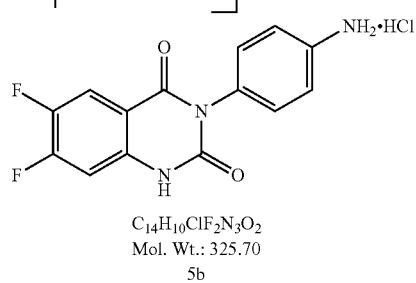
C19H17F2N3O4
Mol. Wt.: 389.35
4b
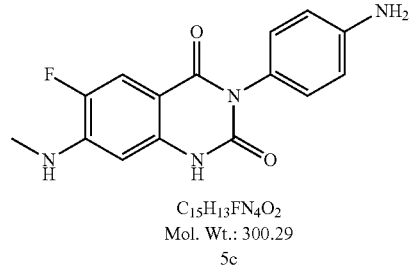
C14H10ClF2N3O2
Mol. Wt.: 325.70
5b
CH3NH2 (7 equiv)
DMSO
Step 3
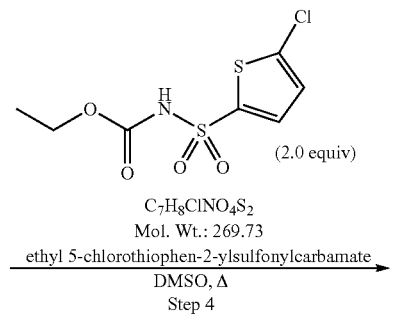
C7H8ClNO4S2
Mol. Wt.: 269.73
ethyl 5-chlorothiophen-2-ylsulfonylcarbamate
DMSO, Δ
Step 4
C15H13FN4O2
Mol. Wt.: 300.29
5c
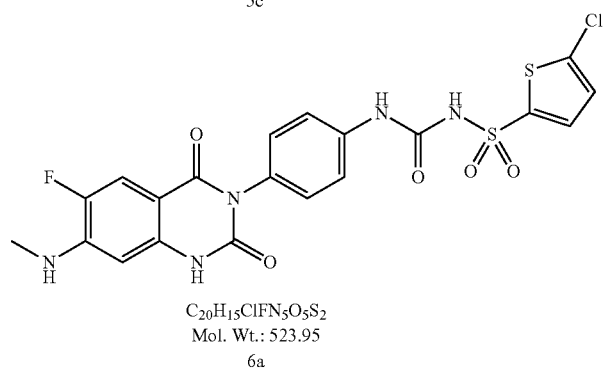
C20H15ClFN5O5S2
Mol. Wt.: 523.95
6a
2N KOH (1.15 equiv)
ACN/H2O,
50° C., 1 h
Step 5
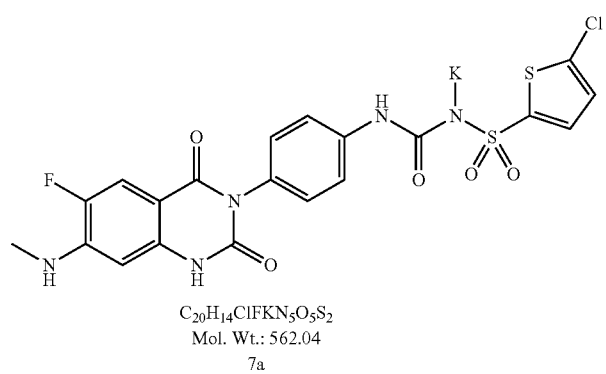
C20H14ClFKN5O5S2
Mol. Wt.: 562.04
7a Step 1.

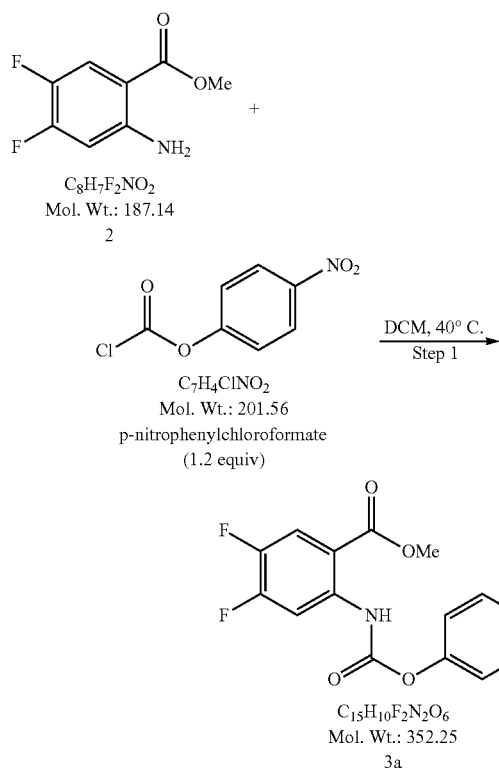

Methyl 2-amino-4,5-difluorobenzoate [2] (38 Kg, 1.0 eq) and dichloromethane (560 Kg, 8x, ACS>99.5%) were charged to a PP1-R1000 reactor (2000 L GL reactor). The reaction mixture was agitated for 5 mins. 4-Nitrophenylchloroformate (49.1 Kg, 1.2 equiv) was charged into PP1-R2000 reactor (200 L) followed by dichloromethane (185 Kg) and agitated the contents for 5 mins. After pressurizing the 200 L reactor the 4-nitrophenylchloroformate solution was transferred into the 2000 L reactor containing dichloromethane solution of [2]. The reaction mixture was heated to 40±5° C. (reflux) under nitrogen gas purge for 3 hrs. The representative TLC analysis confirmed reaction completion (in-process TLC, no compound 2 remaining; 99:1 $CHCl_3$—MeOH). The solution was cooled to 30° C. and distilled off 460 Kg of dichloromethane under vacuum. The 2000 L reactor was charged with 520 Kg of hexanes and cooled the contents of the reactor to 0±5° C. and agitated for 4 hrs. The solid obtained was filtered through GF Nutsche filter lined with a sheet of T-515 LF Typar filter and a sheet of Mel-Tuf 1149-12 filter paper. The filter cake was washed with 20 Kg of hexanes and vacuum dried at 35° C. until constant weight attained. The dry product was discharged (70.15 Kg) with 98% yield. The product confirmed by $^1H$ NMR and TLC analysis.

Step 2. Synthesis of 3-(4-aminophenyl)-6,7-difluoroquinazoline-2,4(1H,3H)-dione hydrochloride, compound 5b

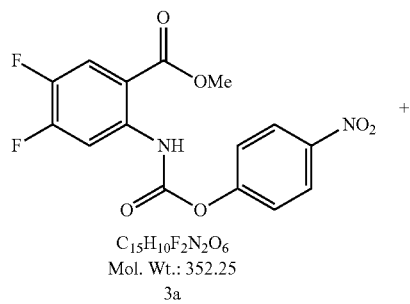

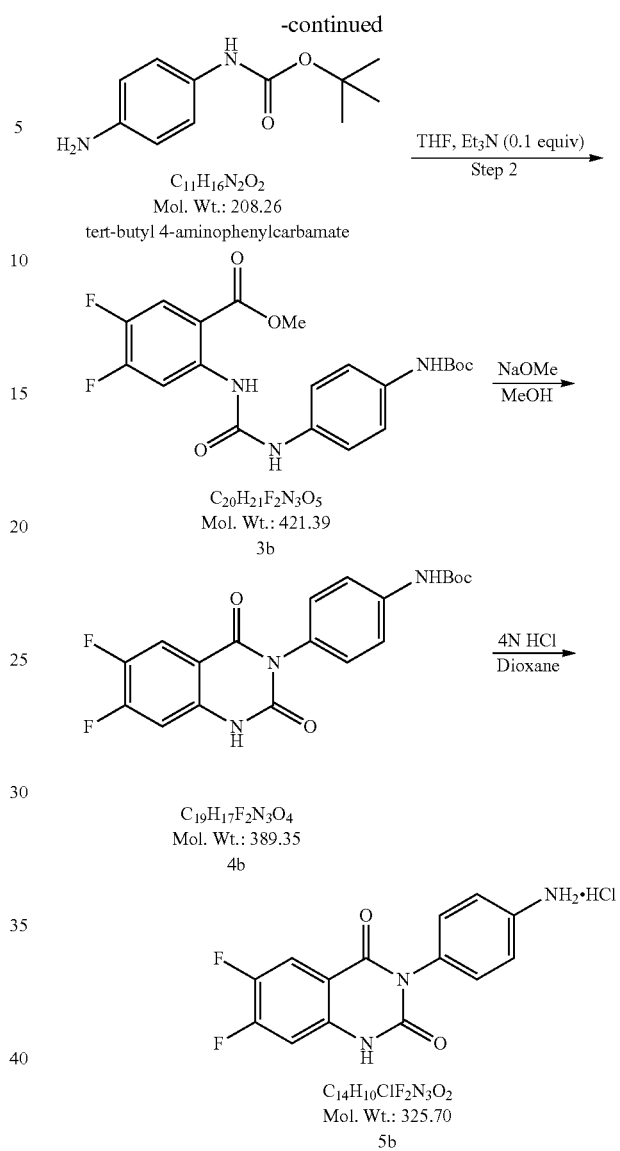

The PP1-R1000 (2000 L GL reactor) reactor was charged with 3a (64.4 Kg, 1.0 eq), anhydrous tetrahydrofuran (557 Kg) and triethylamine (2.2 Kg, 0.1 equiv). The charging line of 2000 L GL reactor was rinsed with tetrahydrofuran (10 Kg). The contents of the reactor were agitated for 25 mins. during that period complete solution was obtained. The PP1-R2000 (200 L HP reactor) reactor was charged with N-Boc-p-phenylenediamine (38 Kg, 1.0 equiv), tetrahydrofuran (89 Kg) and agitated for 30 mins. until complete solution obtained. The contents of the 200 L HP reactor were transferred to the 2000 L GL reactor containing the compound 3a and then heated at 65±5° C. for 2 hrs. The reaction was deemed complete monitored by HPLC after confirming the disappearance of starting material 3a (in-process specification <1%). The contents of 2000 L GL reactor were cooled to 20±5° C. and then charged with sodium methoxide (25% solution in methanol, 41.5 Kg, 1.05 equiv.) over 20 mins. maintaining the temperature below 30° C. The charging lines were rinsed with tetrahydrofuran (10 Kg). The contents were agitated at 25±5° C. for 4 hrs. In-process HPLC analysis confirmed the completion of the reaction when the amount of compound 3b remaining in the reaction mixture is <1%. To this reaction mixture added filtered process water (500 Kg) and distilled under vacuum the 2000 L GL reactor contents into clean 200 L GL receiver until 300 Kg of solvent is distilled. The solids obtained were filtered using GL Nutsche filter and washed with process filtered water until the color of the solid the compound 4b is white to grayish. The 2000 L GL reactor is charged with wet compound 4b filter cake, dioxane (340 Kg) and agitated the contents for 1 hr. The filterable solid obtained were filtered through GL Nutsche filter with a sheet of T-515 LF Typar filter paper. The solid cake was blow dried for 2 hrs and then charged with dioxane (200 Kg) into the 2000 L GL reactor. The contents were agitated for 10 min. and then charged with 4 N HCl in dioxane (914 Kg) over 3 hrs and maintaining the internal temperature below 30° C. The charging line was rinsed with additional dioxane (10 Kg) and the contents of the reactor were agitated for 6 hrs at 25±5° C. The completion of the reaction is monitored by HPLC (in process control compound 4 is <1% in the reaction mixture) for the conversion of compound 4b to compound 5b. The contents of the reactor were cooled to 5±5° C. for 2 hr and the solid obtained was filtered through GL Nutsche filter followed by washing with dioxane (50 Kg). The filter cake was blow dried with 8±7 psig of nitrogen for 30 mins. and purity analyzed by HPLC. The filtered solid was dried to constant weight in vacuum oven at 45° C. for 48 hr. The compound 5b (65.8 Kg, actual yield 110.6%) was discharged and analyzed by $^1$HNMR and HPLC analysis. $^1$H NMR (DMSO): δ 11.75 (s, 1H), 7.88 (dd, 1H), 7.32 (m, 4H), 7.21 (dd, 1H).

Step 3. Synthesis of 3-(4-aminophenyl)-6-fluoro-7-(methylamino)quinazoline-2,4(1H,3H)-dione, Compound 5c

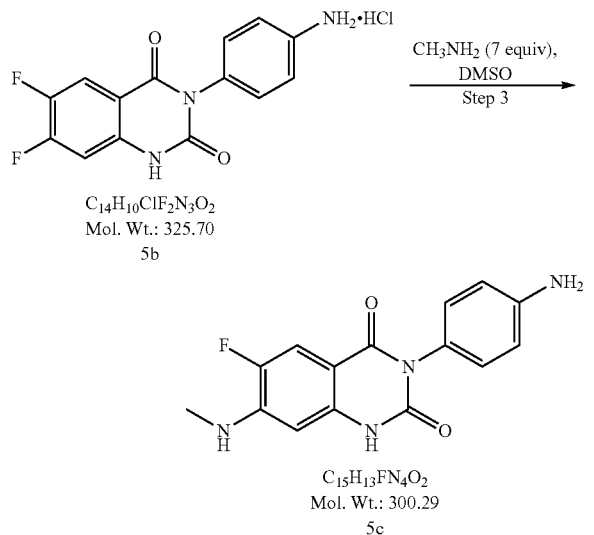

The PP1-R2000 (200 L HP reactor) was charged with compound 5b (18 Kg, 1.0 eq.) and pressurized with 100±5 psig of nitrogen. Vent the nitrogen from the reactor through the atmospheric vent line then open the condenser valve and then charged dimethyl sulfoxide into the reactor (>99.7%, 105 Kg) under blanket of argon. The reactor contents were agitated at 22° C. (19-25° C.) for 15 mins. and then pulled maximum achievable vacuum on the 200 L HP reactor and close all the valves. Using the established vacuum charged to the 200 L HP reactor methylamine (33% wt % in absolute ethanol, 37.2 Kg) at a rate that maintains the internal temperature at 25±5° C. and kept a nitrogen blanket on the reagent solution during charging. After rinsing the charging line with dimethyl sulfoxide (5 Kg) closed the 200 L HP reactor condenser valve and heated the reactor contents to 110±5° C. The contents of the reactor were agitated for at least 5 hrs. at 110±5° C. In-process HPLC taken after 5 hr mins. showed compound 5b content of 0.09%, indicating completion of the reaction (in-process specification ≦1%). The contents of 200 L HP reactor were cooled to 25±5° C. While the 200 L reactor is cooling, closed all the valves of the PP1-R1000 reactor (2000 L GL reactor) and charged with process filtered water (550 Kg). The contents of the 200 L HP reactor were transferred to the 2000 L GL reactor over 15 minutes followed by rinsing the charging line with process filtered water (50 Kg). The contents of the 2000 L GL reactor were agitated for 2 hrs at 5±5° C. The filterable solids obtained were filtered onto PPF200 (GL nutsche filter) fitted with Mel-Tuf 1149-12 filter paper under vacuum. The wet filter cake was discharged and transferred into pre-lined vacuum trays with Dupont's fluorocarbon film (Kind 100 A). Clamped down the special oven paper (KAVON 992) over the vacuum trays containing the wet compound 6 and transferred to the vacuum oven tray dryer. The oven temperature was set to 55° C. and compound 6 dried to a constant weight for 12 hrs. The product 5c was discharged (12.70 Kg) in 76.5% yield (expected 85-95%). HPLC shows 98.96% purity and $^1$H NMR confirmed the structure for compound 5c. $^1$H NMR (DMSO): δ 11.10 (s, 1H), 7.36 (d, 1H), 6.78 (d, 2H), 6.75 (m, 1H), 6.56 (d, 2H), 6.20 (d, 1H), 5.18 (d, 2H), 2.76 (d, 3H).

Step 4. 5-Chloro-N-(4-(6-fluoro-7-(methylamino)-2,4-dioxo-1,2-dihydroquinazolin-3(4H)-yl)phenylcarbamoyl)thiophene-2-sulfonamide

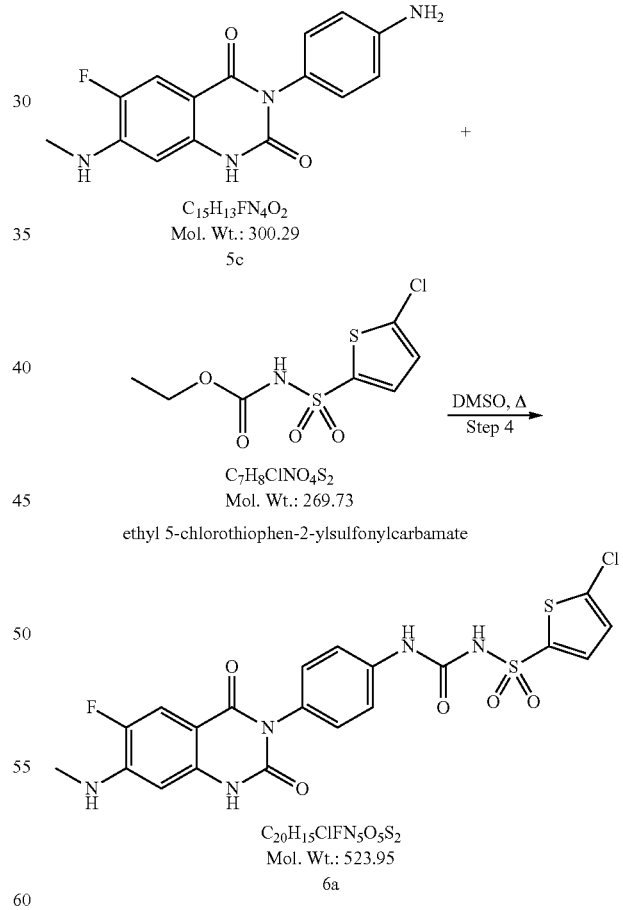

The PP1-R2000 (200 L HP reactor) reactor was charged with 6 (20.7 Kg, 1.0 equiv), Ethyl 5-chlorothiophene-2-ylsulfonylcarbamate (37.5 Kg, 2.0 equiv, >95%), dimethyl sulfoxide (>99%, 75 Kg) and agitated for 15 mins. While pulling maximum achievable vacuum, heated the 200 L HP reactor Number PP1-R2000 at 65±5° C. for 15 hrs. Took the representative sample from the reactor for HPLC analysis, in-process HPLC indicated <0.9% compound 5c remaining in the reaction mixture (in-process criteria for reaction completion compound 6<1%). Charged the 800 L reactor number PP5-R1000 with process filtered water (650 Kg) and then transferred the 200 L HP contents to the 800 L while maintaining the internal temperature below 25° C. The Rinsed the 200 L HP reactor with dimethyl sulfoxide (15 Kg) and transfer to the 800 L reactor which was then agitated for 2 hrs at 5±5° C. The solid formed was filtered through filter PP-F2000 to a 200 L GL receiver under vacuum and rinsed the filter cake with process filtered water (60 Kg). Took a representative sample of the wet cake and did HPLC analysis, if the purity of compound 6a is <95% (in-process control <95% the dichloromethane trituration need). The 800 L GL reactor was charged with all the wet compound 6a, dichloromethane (315 Kg) and agitated the contents for 3 hrs. The solid was filtered through GL nutsche filter lined with 1 sheet of T515 LF TYPAR filter under vacuum. The filter cake was washed with dichloromethane (50 Kg) and blow dried the cake with 8±7 psig of nitrogen for 15 mins. Transferred the filter cake into pre-lined vacuum trays with Dupont fluorocarbon film (Kind 100A) and then into the vacuum oven tray dryer set at 60° C. for 12 hrs. The dried compound 6a was isolated (33.6 Kg, 93% yield) with HPLC purity of 93.5% and 4.3% of sulfonamide. $^1$H NMR confirmed the structure for compound 7. $^1$H NMR (DMSO): δ 11.20 (s, 1H), 9.15 (s, 1H), 7.68 (d, 1H), 7.42 (d, 2H), 7.36 (d, 1H), 7.26 (m, 1H), 7.16 (d, 2H), 6.78 (m, 1H), 6.24 (d, 1H), 2.78 (d, 3H).

Step 5. Potassium (5-chlorothiophen-2-ylsulfonyl)(4-(6-fluoro-7-(methylamino)-2,4-dioxo-1,2-dihydroquinazolin-3(4H)-yl)phenylcarbamoyl)amide, 7a

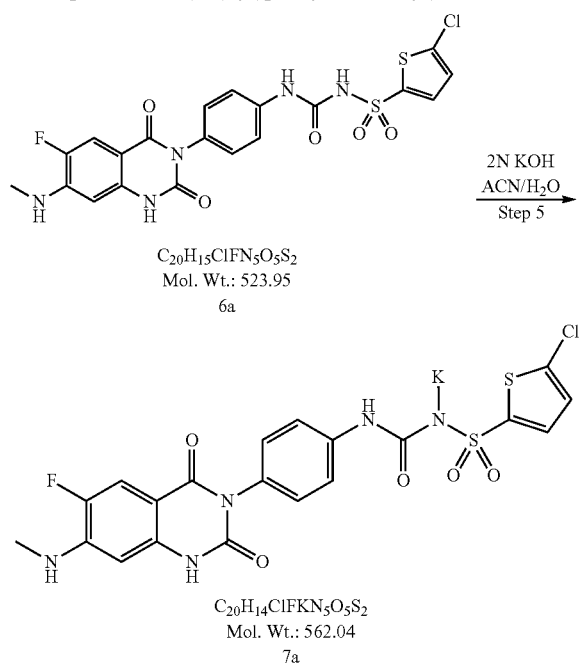

The 800 L GL reactor number PP5-R1000 was charged with acetonitrile (134 Kg), WFI quality water (156 Kg) and agitated the contents for 5 mins. To this then charged compound 6a (33.6 Kg, 1.0 equiv) and the reaction mixture was a suspension at this point. The suspension was charged with aqueous solution (WFI water, 35 Kg) of potassium hydroxide (4.14 Kg, 1.15 equiv, >85%) at a rate that maintains the internal temperature below 30° C. The charging lines were rinsed with WFI quality water (2 Kg) followed by heating the 800 L GL reactor contents to 50±5° C. for 1 hr. The contents were then filtered hot through a bag filter, then a seven cartridge 0.2μ polish filter to clean HDPE drums. The hot filtration system was maintained through out the filtration process so no material crashes out of the solution. Cool the 800 L GL reactor jacket to 25±5° C. before proceeding to the reactor rinse. Rinsed the 800 L GL reactor with pre-mixed solution of acetonitrile (8.5 Kg) and WFI quality water (10 Kg) through the filter system into the drums labeled as 7a hot filtration. Using the pressure vessel the 800 L GL reactor was rinsed with WFI quality water (20 Kg) followed by acetone (20 Kg) then blow it dry with nitrogen (3+2 psig). The 800 GL reactor bottom valve was closed and pulled 20+10 inches Hg of vacuum, then break the vacuum and charge the reactor with the contents of the drums labeled as 7a hot filtration. Cooled the 800 L GL reactor number PP5-R1000 contents to 20±5° C. and then using a polish filter (PP-PF09), charged the reactor with methanol (373 kg, >99%) maintaining the internal temperature below 30oC. The contents of the 800 GL reactor number PP5-R1000 were cooled to 15±5° C. followed by agitation of the contents for 12 hrs at this temperature. During this time the filterable solids were filtered through a clean filter apparatus (PP-F1000) into clean 200 L GL receiver (PPR-04) followed by pressurizing the reactor, pulled 20+10 inches Hg of vacuum on the filter/receiver and filtered the contents. The filter cake was washed with methanol (30 Kg) and blow dried with 8+7 psig of nitrogen for 10 mins. The vacuum oven tray dryer temperature was set to 80° C. prior to loading the wet cake of 7a. Transferred the wet filter cake into the pre-lined vacuum trays with Dupont's fluorocarbon film —Kind 100 A and clamped down the special oven paper (Kavon Mel Tuf paper) over the vacuum trays containing the product wet 7a and transferred to the vacuum oven tray dryer. Set the oven temperature to 80° C. and dry the wet 7a to a constant weight (constant weight is defined as tray reading at least 1 hr apart having the same weight within +50 g. The representative sample was analyzed for residual solvents (residual solvent specifications for API) and it met the specifications. The final API was subjected to equilibration with water (5-6%) for 12 hrs with a tray of WFI quality water present, then thoroughly turned and allowed to stand for an additional 12 hrs and finally subjected to KF analysis (5.5% water content). Transferred the 7-potassium (21.80 Kg, 60.6% yield) to double heavy-duty poly bags and stored in secondary containment. HPLC taken showed purity of 99.7% for 7a and $^1$H NMR confirmed the structure for 7a. $^1$H NMR (DMSO): δ 11.14 (s, 1H), 8.60 (s, 1H), 7.48 (m, 2H), 7.35 (d, 1H), 7.22 (d, 1H), 6.95 (m, 3H), 6.75 (m, 1H), 6.22 (d, 1H), 2.78 (d, 3H).

Example 5

Pharmacological Assays

The pharmacological activity of each of the compounds according to the invention is determined by the following in vitro assays:
I. Inhibition of ADP-Mediated Platelet Aggregation In Vitro 1.

The effect of testing the compound according to the invention on ADP-induced human platelet aggregation was assessed in a 96-well microtiter assay (see generally the procedures in Jantzen, H. M. et al. (1999) *Thromb. Hemost.* 81:111-117) or standard cuvette light transmittance aggregometry using either human platelet-rich plasma (PRP) or human washed platelets.

For preparation of human platelet-rich plasma for aggregation assays, human venous blood was collected from healthy, drug-free volunteers into 0.38% sodium citrate (0.013 M, pH 7.0 final). Platelet-rich plasma (PRP) is prepared by centrifugation of whole blood at 160×g for 20 minutes at room temperature. The PRP layer is removed, transferred to a new tube, and the platelet count is adjusted, if necessary, to achieve a platelet concentration of ~3×10$^8$ platelets/ml using platelet-poor plasma (PPP). PPP is prepared by centrifugation of the remaining blood sample (after removal of PRP) for 20 minutes at 800×g. This preparation of PRP can subsequently be used for aggregation assays in either a 96-well plate or standard cuvette aggregometry.

For preparation of washed platelets, human venous blood is collected from healthy, drug-free volunteers into ACD (85 mM sodium citrate, 111 mM glucose, 71.4 mM citric acid) containing $PGI_2$ (1.25 ml ACD containing 0.2 µM $PGI_2$ final; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730 g and resuspending the platelet pellet in CGS (13 mM sodium citrate, 30 mM glucose, 120 mM NaCl; 2 ml CGS/10 ml original blood volume) containing 1 U/ml apyrase (grade V, Sigma, St. Louis, Mo.). After incubation at 37° C. for 15 minutes, the platelets are collected by centrifugation at 730 g for 10 minutes and resuspended at a concentration of $3 \times 10^8$, platelets/ml in Hepes-Tyrode's buffer (10 mM Hepes, 138 mM NaCl, 5.5 mM glucose, 2.9 mM KCl, 12 mM $NaHCO_3$, pH 7.4) containing 0.1% bovine serum albumin, 1 mM $CaCl_2$ and 1 mM $MgCl_2$. This platelet suspension is kept >45 minutes at 37° C. before use in aggregation assays.

2.

For cuvette light transmittance aggregation assays, serial dilutions (1:3) of test compounds were prepared in 100% DMSO in a 96 well V-bottom plate (final DMSO concentration in the cuvette was 0.6%). The test compound (3 µl of serial dilutions in DMSO) was preincubated with PRP for 30-45 seconds prior to initiation of aggregation reactions, which were performed in a ChronoLog aggregometer by addition of agonist (5 or 10 µM ADP) to 490 µL of PRP at 37° C. In some cases, light transmittance aggregometry was performed using 490 µL of washed platelets (prepared as described above) at 37° C., and aggregation was initiated by addition of 5 µM ADP and 0.5 mg/ml human fibrinogen (American Diagnostics, Inc., Greenwich, Conn.). The aggregation reaction is recorded for ~5 min, and maximum extent of aggregation is determined by the difference in extent of aggregation at baseline, compared to the maximum aggregation that occurs during the five minute period of the assay. Inhibition of aggregation was calculated as the maximum aggregation observed in the presence of inhibitor, compared to that in the absence of inhibitor. $IC_{50}$s were derived by non-linear regression analysis using the Prism software (GraphPad, San Diego, Calif.).

3.

Inhibition of ADP-dependent aggregation was also determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. For 96-well plate aggregation using platelet-rich plasma (PRP), the total reaction volume of 0.2 ml/well includes 180 µl of PRP (~3×108 platelets/ml, see above), 6 µl of either serial dilution of test compounds in 20% DMSO or buffer (for control wells), and 10 µl of 20×ADP agonist solution (100 µM). The OD of the samples is then determined at 450 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 450 nm at t=5 minutes compared to t=0 minutes and is expressed as % of the decrease in the ADP control samples after correcting for changes in the unaggregated control samples. $IC_{50}$s were derived by non-linear regression analysis.

For 96-well plate aggregation using washed platelets, the total reaction volume of 0.2 ml/well includes in Hepes-Tyrodes buffer/0.1% BSA: $4.5 \times 10^7$ apyrase-washed platelets, 0.5 mg/ml human fibrinogen (American Diagnostica, Inc., Greenwich, Conn.), serial dilutions of test compounds (buffer for control wells) in 0.6% DMSO. After ~5 minutes preincubation at room temperature, ADP is added to a final concentration of 2 µM which induces submaximal aggregation. Buffer is added instead of ADP to one set of control wells (ADP-control). The OD of the samples is then determined at 450 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 450 nm at t=5 minutes compared to t=0 minutes and is expressed as % of the decrease in the ADP control samples after correcting for changes in the unaggregated control samples. $IC_{50}$s were derived by non-linear regression analysis.

II. Inhibition of [3H]2-MeS-ADP Binding to Platelets

1. The Ability of Candidate Molecules to Inhibit the Binding of [3H]2-MeS-ADP to the P2Y12 Receptor on Platelets was Determined Using a Radioligand Binding Assay.

Utilizing this assay the potency of inhibition of such compounds with respect to [$^3$H]2-MeS-ADP binding to whole platelets is determined. Under the conditions described in II (3) below, the binding of [$^3$H]2-MeS-ADP is solely due to the interaction of this ligand with the $P2Y_{12}$ receptor, in that all the specific binding measured in this assay is compatible with a $P2Y_{12}$ antagonist (i.e., the specific binding is reduced to background levels by competition with an excess of $P2Y_{12}$ antagonist, with no competition of binding when a $P2Y_1$ antagonist is pre-incubated with the platelet preparation). [$^3$H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at 3-6×10$^9$ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of 6.66×10$^8$ platelets/ml. Binding experiments are performed after >45 minutes resting of the platelets.

2.

Alternatively, binding experiments are performed with fresh human platelets prepared as described in section I (Inhibition of ADP-Mediated Platelet Aggregation in vitro), except that platelets are resuspended in Hepes-Tyrode's buffer containing 0.1% BSA (Sigma, St. Louis, Mo.) at a concentration of 6.66×10$^8$ platelets/mil. Very similar results are obtained with fresh and outdated platelets.

3.

A platelet ADP receptor binding assay (ARB) using the tritiated potent agonist ligand [$^3$H]2-MeS-ADP (Jantzen, H. M. et al. (1999) *Thromb. Hemost.* 81:111-117) has been adapted to the 96-well microtiter format. In an assay volume of 0.2 ml Hepes-Tyrode's buffer with 0.1% BSA and 0.6% DMSO, 1×10$^8$ apyrase-washed platelets are preincubated in 96-well flat bottom microtiter plates for 5 minutes with serial dilutions of test compounds before addition of 1 nM [$^3$H]2-MeS-ADP ([$^3$H]2-methylthioadenosine-5'-diphosphate, ammonium salt; specific activity 20-50 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain 10 □M unlabelled 2-MeS-ADP (RBI, Natick, Mass.). After incubation for 15 minutes at room temperature, unbound radioligand is separated by rapid filtration and two washes with cold (4-8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glass-fiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compound dilutions. $IC_{50}$s were derived by non-linear regression analysis.

In the table below, activity in the PRP assay is provided as follows: +++, $IC_{50}$<10 μM; ++, 10 μM<$IC_{50}$<30 μM. Activity in the ARB assay is provided as follows: +++, $IC_{50}$ <0.05 μM; ++, 0.05 μM<$IC_{50}$<0.5 μM.

TABLE 5

| Example No. | ARB Binding | PRP Activity |
| --- | --- | --- |
| Example 2 | +++ | +++ |
| Example 3 | ++ | ++ |

Example 6

Synthesis of [4-(6-fluoro-7-methylamino-2,4-dioxo-1,4-dihydro-2H-quinazolin-3-yl)-phenyl]-5-chloro-thiophen-2-yl-sulfonylurea potassium salt (9a) (amorphous form)

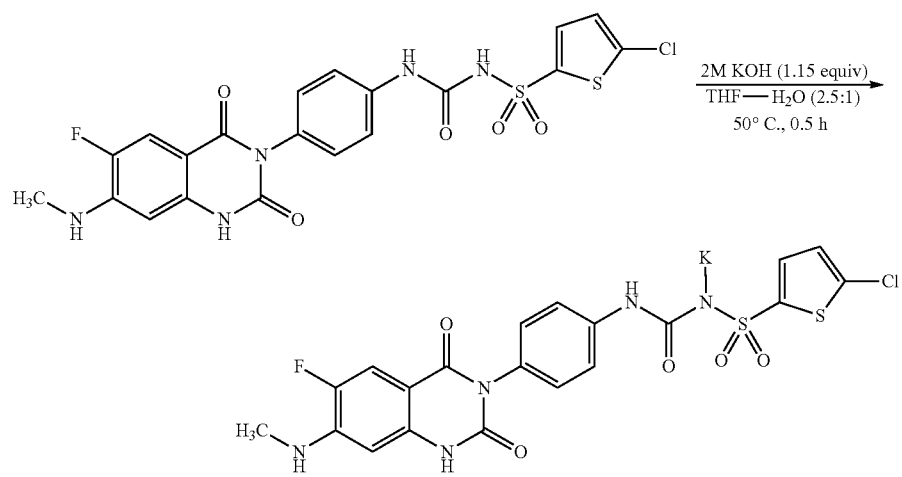

The free-acid, sulfonylurea, (7.0 g, 13.365 mmol) was suspended in THF/H$_2$O (55: 22 mL, ca. 2.5:1), and treated with 2M KOH (7.70 mL, 15.40 mmol, 1.15 equiv) drop wise, over ca. 5 min. By the time the addition was over, a clear solution resulted. But, then soon after (<5 mins), a solid precipitated out and reaction mixture became a heavy suspension. This was heated in an oil-bath to 50° C., and the resulting clear viscous light brown solution was held there for 0.5 h. On cooling to rt., the title compound precipitated out. The mixture was diluted with i-PrOH (250 mL, 3× the original reaction volume), stirred at rt. for 3 h, and then filtered through a Buchner funnel to yield the title compound as a colorless solid. This was dried in a vacuum oven at 80° C. to yield 7.20 g (96%) of an amorphous solid. MS (negative scan): 521.7; 523.7.

Example 7

Conversion of the Sulfonylurea (7a) to its Sodium Salt (10a)

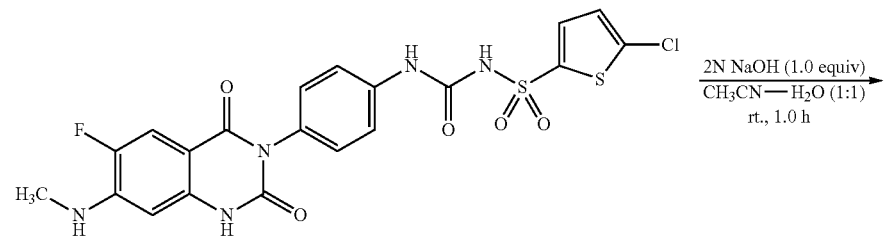

-continued

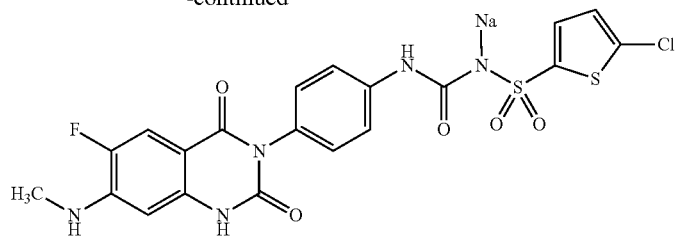

10a 1-(5-chlorothiophen-2-ylsulfonyl)-3-(4-(6-fluoro-7-(methylamino)-2,4-dioxo-1,2-dihydroquinazolin-3(4H)-yl) phenyl) urea (3.0 g, 5.728 mmol) 7a was suspended in $CH_3CN/H_2O$ (1:1; 70 mL) and was treated with 2N NaOH (2.90 mL, 5.80 mmol), dropwise. Within ca. 15 minutes, a clear solution resulted. After stirring for 1.0 h, the now light brown solution was lyophilized to afford the crude product as an amorphous solid 10a. MS (negative scan): 522.0; 524.0.

Example 8

Preparation of Amorphous Form of the Sodium Salt

Sodium salt 10b was suspended in isopropanol (100 mL) and refluxed for ca. 45 min, then hot filtered to yield a tan solid, which is mostly the title compound by HPLC. The tan solid was suspended in $CH_3CN$:EtOH (1:2) (100 mL) and refluxed for 45 mins., then hot filtered to afford 2.54 g of the title compound as a tan solid (99.6887% pure by analytical HPLC, long column). The filtrate was diluted with EtOH until the ratio of ACN:EtOH became (1:3) and then let stand at room temperature overnight when the title compound precipitated out to afford 210 mg of the title compound (purity: 99.6685% by analytical HPLC, long column).

Example 9

Preparation of Polymorph form A of Potassium Salt by Recrystallization

Recrystallization: The crude product can be recrystallized either from MeOH or MeOH/EtOH (3:1) by first heating to reflux to dissolve, and then cooling to room temperature to precipitate.

Recrystallization From MeOH: 1.0 g of the potassium salt was suspended in MeOH (150 mL) and heated to reflux for 0.5 h, resulting in an almost clear solution. This was then hot filtered through a Buchner funnel. The clear filtrate on standing at room temperature deposited a colorless solid. This was stirred overnight and then collected by filtration through a Buchner funnel. The solid product was rinsed with EtOH (2×4.0 mL) and dried in a vacuum oven at 80° C. for 20 h to yield 740 mg of a colorless solid. The mother liquor yielded more title compound on concentration to ca. one-third of the original volume.

Recrystallization from EtOH/MeOH: 1.0 g of the potassium salt was suspended in the solvent mixture EtOH/MeOH (1:3) (200 mL), and heated to reflux for 0.5 h resulting in an almost clear solution. This was then hot filtered through a Buchner funnel. The clear filtrate on standing at room temperature deposited a colorless solid. This was collected by filtration through a Buchner funnel. The solid product was rinsed with EtOH and dried in vacuum oven at 80° C. for 20 h to give a colorless solid. The mother liquor yielded more title compound upon concentration to ca. one-third of the original volume.

Example 10

Preparation of Polymorph Form B of Potassium Salt by Recrystallization

Recrystallization: The crude product can be recrystallized from $EtOH/H_2O$ (91:9) or a small volume of MeOH by first heating to reflux to dissolve, and then cooling to room temperature to precipitate.

Recrystallization from $EtOH/H_2O$: 1.0 g of the potassium salt was suspended in EtOH (190 mL) and heated to reflux. To the heavy suspension was added $H_2O$ (18.0 mL) dropwise, resulting in a clear colorless solution. On cooling to room temperature, the title compound precipitated out as a colorless solid. It was collected by filtration through a Buchner funnel, and rinsed with EtOH (2×4.0 mL). This was dried in vacuum oven at 80° C. for 20 h, to give 650 mg of a colorless solid. The mother liquor yielded more title compound upon concentration to ca. one-third of the original volume.

Large Scale Recrystallization from small volume of MeOH: 6.6 g of the potassium salt was suspended in MeOH (30 mL) and heated to reflux for 5 hr, the solid did not completely dissolve in less volume of methanol. After cooling the solid was filtered and rinsed with iPrOH. This was dried in vacuum oven at 80° C. for 20 h, to give 6.2 g of colorless solid, characterized to be Form B.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:
1. A compound [4-(6-fluoro-7-methylamino-2,4-dioxo-1,4-dihydro-2H-quinazolin-3-yl)-phenyl]-5-chloro-thiophen-2-yl-sulfonylurea having the following formula:

(I)

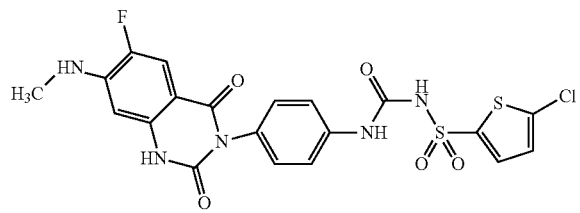

or a pharmaceutically acceptable salt or hydrate thereof.

2. The compound of claim 1, having the formula:

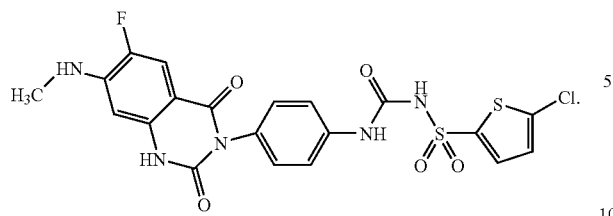

3. The compound of claim 1, wherein the pharmaceutically acceptable salt is selected from the group consisting of:

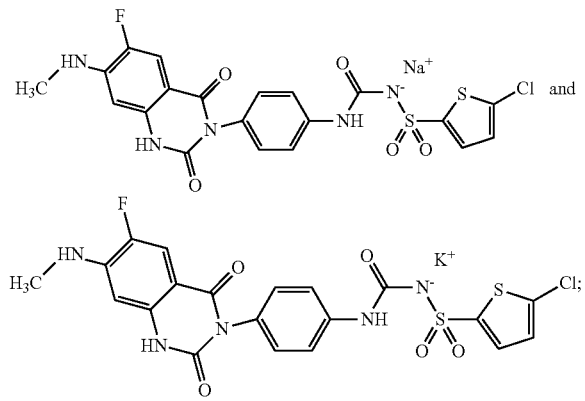

or hydrates thereof.

4. The compound of claim 1, wherein the compound is [4-(6-fluoro-7-methylamino-2,4-dioxo-1,4-dihydro-2H-quinazolin-3-yl)-phenyl]-5-chloro-thiophen-2-yl-sulfonylurea sodium salt having the formula:

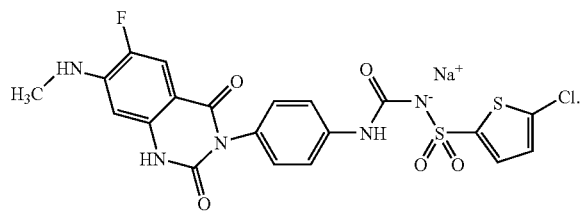

5. The compound of claim 1, wherein the compound is [4-(6-fluoro-7-methylamino-2,4-dioxo-1,4-dihydro-2H-quinazolin-3-yl)-phenyl]-5-chloro-thiophen-2-yl-sulfonylurea potassium salt having the formula:

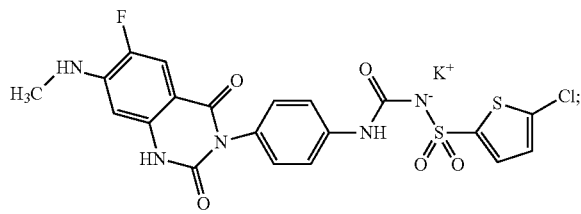

or hydrates thereof.

6. The compound of claim 1, that is in an isolated form.

7. The compound of claim 5 in a crystalline solid form A characterized by at least one of:
(i) an infra red spectrum substantially in accordance with FIG. 5;
(ii) an X-ray powder diffraction pattern substantially in accordance with FIG. 2; and
(iii) a DSC scan substantially in accordance with FIG. 14.

8. The compound of claim 5 in a crystalline solid form A characterized by an infra red spectrum substantially in accordance with FIG. 5.

9. The compound of claim 5 in a crystalline solid form A characterized by at least one of:
(i) an infra red spectrum comprising absorption peaks at about 3559, 3389, 3324, 1698, 1623, 1563, 1510, 1448, 1431, 1403, 1383, 1308, 1269, 1206, 1174, 1123, 1091, 1072, 1030, 987, 939, 909, 871, 842, 787, 780, 769, 747, 718, 701, 690 and 667 $cm^{-1}$;
(ii) an X-ray powder diffraction pattern comprising peaks at about 9.5 and about 25.5°2θ; and
(iii) a DSC maximum endotherm at about 246° C.

10. The compound of claim 5 in a crystalline solid form A characterized by an infra red spectrum comprising absorption peaks at about 3559, 3389, 3324, 1698, 1623, 1563, 1510, 1448, 1431, 1403, 1383, 1308, 1269, 1206, 1174, 1123, 1091, 1072, 1030, 987, 939, 909, 871, 842, 787, 780, 769, 747, 718, 701, 690 and 667 $cm^{-1}$.

11. The compound of claim 5 in a crystalline solid form A characterized by an infrared spectrum comprising peaks at about 3389 $cm^{-1}$ and about 1698 $cm^{-1}$.

12. The compound of claim 5 in a crystalline solid form A characterized by an X-ray powder diffraction pattern comprising peaks at about 9.5 and about 25.5°2θ.

13. The compound of claim 5 in a crystalline solid Form A characterized by
an X-ray Powder diffraction pattern comprising a peak at about 9.5 and about 25.5°2θ and an infrared spectrum comprising at least one peak selected from about 3389 $cm^{-1}$ and about 1698 $cm^{-1}$.

14. The compound of claim 5 in a crystalline solid form A characterized by a DSC maximum endotherm at about 246° C.

15. The compound of claim 5 in a crystalline solid form B characterized by at least one of:
(i) an infra red spectrum substantially in accordance with FIG. 6;
(ii) an X-ray powder diffraction pattern substantially in accordance with FIG. 3; and
(iii) a DSC scan substantially in accordance with FIG. 16.

16. The compound of claim 5 in a crystalline solid form B characterized by an infra red spectrum substantially in accordance with FIG. 6.

17. The compound of claim 5 in a crystalline solid form B characterized by at least one of:
(i) an infra red spectrum comprising absorption peaks at about 3584, 3327, 3189, 2935, 2257, 2067, 1979, 1903, 1703, 1654, 1630, 1590, 1557, 1512, 1444, 1429, 1406, 1375, 1317, 1346, 1317, 1288, 1276, 1243, 1217, 1182, 1133, 1182, 1133, 1093, 1072, 1033, 987, 943, 907, 883, 845, 831, 805, 776, 727, 694 and 674 $cm^{-1}$;
(ii) an X-ray powder diffraction pattern comprising peaks at about 20.3°2θ and about 25.1°2θ; and
(iii) a DSC maximum endotherm at about 293° C.

18. The compound of claim 5 in a crystalline solid form B characterized by an infra red spectrum comprising absorption peaks at about 3584, 3327, 3189, 2935, 2257, 2067, 1979, 1903, 1703, 1654, 1630, 1590, 1557, 1512, 1444, 1429, 1406, 1375, 1317, 1346, 1317, 1288, 1276, 1243, 1217, 1182, 1133, 1182, 1133, 1093, 1072, 1033, 987, 943, 907, 883, 845, 831, 805, 776, 727, 694 and 674 $cm^{-1}$.

19. The compound of claim 5 in a crystalline solid form B characterized by an infrared spectrum comprising peaks at about 3327 $cm^{-1}$ and about 1630 $cm^{-1}$.

20. The compound of claim 5 in a crystalline solid form B characterized by an X-ray powder diffraction pattern comprising peaks at about 20.3°2θ and about 25.1°2θ.

21. The compound of claim 5 in a crystalline solid Form B characterized by an X-ray Powder diffraction pattern comprising a peak at about 20.3°2θ and about 25.1°2θ and an infrared spectrum comprising at least one peak selected from about 3327 cm$^{-1}$ and about 1630 cm$^{-1}$.

22. The compound of claim 5 in a crystalline solid form B characterized by a DSC maximum endotherm at about 293° C.

23. The compound of claim 4 having an amorphous form which provides at least one of:
  (i) an infra red spectrum substantially in accordance with FIG. 7;
  (ii) an X-ray powder diffraction pattern substantially in accordance with FIG. 4; and
  (iii) a DSC scan substantially in accordance with FIG. 18.

24. The compound of claim 4 having an amorphous form characterized by an infra red spectrum comprising absorption peaks at about 3560, 1711, 1632, 1556, 1512, 1445, 1407, 1375, 1309, 1280, 1227, 1133, 1092, 1032, 987, 905, 781, 770 and 691 cm$^{-1}$.

25. The compound of claim 4 having an amorphous form which provides an X-ray powder diffraction pattern substantially in accordance with FIG. 4.

26. The compound of claim 4 having an amorphous form characterized by an X-ray powder diffraction pattern comprising a broad peak substantially between about 15 and about 30°2θ.

27. The compound of claim 5 in a crystalline solid form A obtained by at least one of:
  (i) crystallizing [4-(6-fluoro-7-methylamino-2,4-dioxo-1,4-dihydro-2H-quinazolin-3-yl)-phenyl]-5-chloro-thiophen-2-yl-sulfonylurea potassium salt in at least one solvent selected from the group consisting of ethanol, methanol and combinations thereof and drying such that the crystal contained some solvent; and
  (ii) heating [4-(6-fluoro-7-methylamino-2,4-dioxo-1,4-dihydro-2H-quinazolin-3-yl)-phenyl]-5-chloro-thiophen-2-yl-sulfonylurea potassium salt in at least one solvent selected from the group consisting of ethanol, methanol and combinations thereof; crystallizing at a temperature of from about 50° C. to −10° C. and drying until the crystals contained at least about 0.05% solvent.

28. The compound of claim 5 in a crystalline solid form B obtained by at least one of:
  (i) heating [4-(6-fluoro-7-methylamino-2,4-dioxo-1,4-dihydro-2H-quinazolin-3-yl)-phenyl]-5-chloro-thiophen-2-yl-sulfonylurea potassium salt from a solvent combination of ethanol and water; crystallizing at a temperature of from about 50° C. to −10° C. and drying until the crystals contain less than 0.05% solvent; and
  (ii) crystallizing [4-(6-fluoro-7-methylamino-2,4-dioxo-1,4-dihydro-2H-quinazolin-3-yl)-phenyl]-5-chloro-thiophen-2-yl-sulfonylurea potassium salt from a solvent combination of ethanol and water and drying such that the crystal contained less than 0.05% solvent.

29. The compound of claim 4 having an amorphous form obtained by at least one of:
  (i) heating [4-(6-fluoro-7-methylamino-2,4-dioxo-1,4-dihydro-2H-quinazolin-3-yl)-phenyl]-5-chloro-thiophen-2-yl-sulfonylurea sodium salt in at least one solvent selected from the group consisting of isopropanol, acetonitrile, ethanol and combinations thereof; and crystallizing at a temperature of from about 50° C. to −10° C.;
  (ii) crystallizing [4-(6-fluoro-7-methylamino-2,4-dioxo-1,4-dihydro-2H-quinazolin-3-yl)-phenyl]-5-chloro-thiophen-2-yl-sulfonylurea sodium salt from at least one solvent selected from the group consisting of isopropanol, acetonitrile, ethanol and combinations thereof; and
  (iii) heating [4-(6-fluoro-7-methylamino-2,4-dioxo-1,4-dihydro-2H-quinazolin-3-yl)-phenyl]-5-chloro-thiophen-2-yl-sulfonylurea sodium salt in about 75% relative humidity.

30. The compound of claim 7 or 15, that is in an isolated form.

31. The compound of claim 23, that is in an isolated form.

32. A pharmaceutical composition comprising a therapeutically effective amount of a compound according to claim 1 or a pharmaceutically acceptable salt or hydrate thereof and a pharmaceutically acceptable vehicle or carrier.

33. The pharmaceutical composition of claim 32, wherein the compound or a pharmaceutically acceptable salt or hydrate thereof in the composition is in at least one solid form.

34. The pharmaceutical composition of claim 32 wherein said solid form is selected from the group consisting of [4-(6-fluoro-7-methylamino-2,4-dioxo-1,4-dihydro-2H-quinazolin-3-yl)-phenyl]-5-chloro-thiophen-2-yl-sulfonylurea potassium salt Form A, [4-(6-fluoro-7-methylamino-2,4-dioxo-1,4-dihydro-2H-quinazolin-3-yl)-phenyl]-5-chloro-thiophen-2-yl-sulfonylurea potassium salt Form B, and [4-(6-fluoro-7-methylamino-2,4-dioxo-1,4-dihydro-2H-quinazolin-3-yl)-phenyl]-5-chloro-thiophen-2-yl-sulfonylurea sodium salt amorphous form.

35. The pharmaceutical composition of claim 32 wherein at least one of [4-(6-fluoro-7-methylamino-2,4-dioxo-1,4-dihydro-2H-quinazolin-3-yl)-phenyl]-5-chloro-thiophen-2-yl-sulfonylurea potassium salt Form A, [4-(6-fluoro-7-methylamino-2,4-dioxo-1,4-dihydro-2H-quinazolin-3-yl)-phenyl]-5-chloro-thiophen-2-yl-sulfonylurea potassium salt Form B, and [4-(6-fluoro-7-methylamino-2,4-dioxo-1,4-dihydro-2H-quinazolin-3-yl)-phenyl]-5-chloro-thiophen-2-yl-sulfonylurea sodium salt amorphous form are present in a therapeutically effective amount.

36. The pharmaceutical composition of claims 34 or 35 wherein the composition is selected from the group consisting of a solid oral composition, a tablet, a capsule, and a dry powder for inhalation.

37. The pharmaceutical composition of claim 36 wherein the solid oral composition is a tablet or a capsule.

38. The pharmaceutical composition of claim 32, wherein said therapeutically effective amount is an amount effective to inhibit platelet aggregation in the mammal.

39. The pharmaceutical composition of claim 38, wherein said platelet aggregation is platelet ADP-dependent aggregation.

40. The pharmaceutical composition of claim 39, wherein said mammal is a human.

41. The pharmaceutical composition of claim 32, wherein said compound is an effective inhibitor of [$^3$H]2-MeS-ADP binding to platelet ADP receptors.

42. The pharmaceutical composition of claim 32, wherein the composition is a solid oral composition.

43. The pharmaceutical composition of claim 32, wherein the composition is a tablet or capsule.

44. The pharmaceutical composition of claim 32, wherein the composition is an aerosol or dry powder for inhalation.

45. A pharmaceutical composition comprising a therapeutically effective amount of a compound according to claim 1 or a pharmaceutically acceptable salt or hydrate thereof and an additional therapeutic agent useful for treating a condition or disorder selected from the group consisting of thrombosis, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (coronary artery bypass graft) surgery, vascular gram surgery, stent placements and insertion of endovascular devices, prostheses, and hypercoagulable states related to genetic predisposition or cancers.

46. A method of producing [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form A, comprising at least one of:
  (i) crystallizing [4-(6-fluoro-7-methylamino-2,4-dioxo-1,4-dihydro-2H-quinazolin-3-yl)-phenyl]-5-chloro-thiophen-2-yl-sulfonylurea potassium salt from at least one solvent selected from the group consisting of ethanol, methanol, and combinations thereof and drying such that the crystal contained some solvent; and
  (ii) heating [4-(6-fluoro-7-methylamino-2,4-dioxo-1,4-dihydro-2H-quinazolin-3-yl)-phenyl]-5-chloro-thiophen-2-yl-sulfonylurea potassium salt in at least one solvent selected from the group consisting of ethanol, methanol, and combinations thereof; crystallizing at a temperature of from about 50° C. to −10° C. and drying until the crystals contained at least about 0.05% solvent.

47. A method of producing [4-(6-fluoro-7-methylamino-2,4-dioxo-1,4-dihydro-2H-quinazolin-3-yl)-phenyl]-5-chloro-thiophen-2-yl-sulfonylurea potassium salt in a crystalline solid form B, comprising at least one of:
  (i) heating [4-(6-fluoro-7-methylamino-2,4-dioxo-1,4-dihydro-2H-quinazolin-3-yl)-phenyl]-5-chloro-thiophen-2-yl-sulfonylurea potassium salt in a solvent combination of ethanol and water; crystallizing at a temperature of from about 50° C. to −10° C. and drying until the crystals contain less than 0.05% solvent; and
  (ii) crystallizing [4-(6-fluoro-7-methylamino-2,4-dioxo-1,4-dihydro-2H-quinazolin-3-yl)-phenyl]-5-chloro-thiophen-2-yl-sulfonylurea potassium salt from a solvent combination of ethanol and water and drying such that the crystal contained less than 0.05% solvent.

48. A method of producing [4-(6-fluoro-7-methylamino-2,4-dioxo-1,4-dihydro-2H-quinazolin-3-yl)-phenyl]-5-chloro-thiophen-2-yl-sulfonylurea sodium salt in an amorphous form, comprising at least one of:
  (i) heating [4-(6-fluoro-7-methylamino-2,4-dioxo-1,4-dihydro-2H-quinazolin-3-yl)-phenyl]-5-chloro-thiophen-2-yl-sulfonylurea sodium salt in at least one solvent selected from the group consisting of isopropanol, acetonitrile, ethanol and combinations thereof; and crystallizing at a temperature of from about 50° C. to −10° C.;
  (ii) crystallizing [4-(6-fluoro-7-methylamino-2,4-dioxo-1,4-dihydro-2H-quinazolin-3-yl)-phenyl]-5-chloro-thiophen-2-yl-sulfonylurea sodium salt from at least one solvent selected from the group consisting of isopropanol, acetonitrile, ethanol and combinations thereof; and
  (iii) heating [4-(6-fluoro-7-methylamino-2,4-dioxo-1,4-dihydro-2H-quinazolin-3-yl)-phenyl]-5-chloro-thiophen-2-yl-sulfonylurea sodium salt in about 75% relative humidity.

49. A method for the preparation of a pharmaceutical composition comprising admixing a therapeutically effective amount of the compound of claim 1 or a pharmaceutically acceptable salt or hydrate thereof with a pharmaceutically acceptable vehicle or carrier.

\* \* \* \* \*

UNITED STATES PATENT AND TRADEMARK OFFICE
CERTIFICATE OF CORRECTION

PATENT NO. : 8,058,284 B2  
APPLICATION NO. : 11/556490  
DATED : November 15, 2011  
INVENTOR(S) : Scarborough et al.

Page 1 of 1

It is certified that error appears in the above-identified patent and that said Letters Patent is hereby corrected as shown below:

Title Page,

(75) Inventors should read: Robert Scarborough, Half Moon Bay, CA (US); Carroll Anna Scarborough, legal representative, Half Moon Bay, CA (US); Wolin Huang, Foster City, CA (US); Mukund Mehrotra, South San Francisco, CA (US); Xiaoming Zhang, Sunnyvale, CA (US); Hilary Cannon, Hertfordshire (GB); Craig M. Grant, Burwell (GB); Anjali Pandey, Fremont, CA (US); Pamela B. Conley, Palo Alto, CA (US); Patrick Andre, San Mateo, CA (US); David R. Phillips, San Mateo, CA (US); Uma Sinha, San Francisco, CA (US)

Signed and Sealed this  
Twenty-sixth Day of April, 2016

Michelle K. Lee  
*Director of the United States Patent and Trademark Office*